United States Patent
Beaudoin

(10) Patent No.: US 12,150,989 B2
(45) Date of Patent: *Nov. 26, 2024

(54) COVALENTLY MODIFIED ANTIGENS FOR IMPROVED IMMUNE RESPONSE AND/OR STABILITY

(71) Applicant: DEFENCE THERAPEUTICS INC., Vancouver (CA)

(72) Inventor: Simon Beaudoin, Sherbrooke (CA)

(73) Assignee: DEFENCE THERAPEUTICS INC., Vancouver (CA)

( * ) Notice: Subject to any disclaimer, the term of this patent is extended or adjusted under 35 U.S.C. 154(b) by 83 days.

This patent is subject to a terminal disclaimer.

(21) Appl. No.: 17/709,599

(22) Filed: Mar. 31, 2022

(65) Prior Publication Data

US 2022/0218820 A1 Jul. 14, 2022

Related U.S. Application Data

(63) Continuation of application No. 17/516,161, filed on Nov. 1, 2021, now Pat. No. 11,291,717.

(60) Provisional application No. 63/202,047, filed on May 25, 2021, provisional application No. 63/127,731, filed on Dec. 18, 2020.

(51) Int. Cl.
| | | |
|---|---|---|
| *A61K 39/385* | (2006.01) | |
| *A61K 39/215* | (2006.01) | |
| *A61P 31/14* | (2006.01) | |
| *A61K 39/00* | (2006.01) | |

(52) U.S. Cl.
CPC .......... *A61K 39/385* (2013.01); *A61K 39/215* (2013.01); *A61P 31/14* (2018.01); *A61K 2039/6006* (2013.01); *A61K 2039/6018* (2013.01); *A61K 2039/6031* (2013.01); *A61K 2039/627* (2013.01)

(58) Field of Classification Search
None
See application file for complete search history.

(56) References Cited

U.S. PATENT DOCUMENTS

| 5,955,365 A | 9/1999 | Szoka, Jr. et al. |
| 7,732,177 B2 | 6/2010 | Iadonato et al. |
| 11,291,717 B1 | 4/2022 | Beaudoin |
| 2022/0218820 A1 | 7/2022 | Beaudoin |

FOREIGN PATENT DOCUMENTS

| EP | 1046394 A2 | 10/2000 |
| WO | WO/2017/156630 | 9/2017 |
| WO | WO/2018/165752 | 9/2018 |
| WO | WO/2020/252298 A1 | 12/2020 |
| WO | WO2022/126239 | 6/2022 |
| WO | WO/2022/232945 | 11/2022 |

OTHER PUBLICATIONS

Anding et al., (2017). Cleaning House: Selective Autophagy of Organelles. *Devopmental Cell*, 41(1):10-22.
Anguille et al., (2014). Clinical use of dendritic cells for cancer therapy. *Lancet Oncology*, 15(7):e257-67.
Azuar et al., (2019). Cholic Acid-based Delivery System for Vaccine Candidates against Group A *Streptococcus*. *ACS Medicinal Chemistry Letters*, 10: 1253-1529.
Beaudoin et al., (2016). ChAcNLS, a novel modification to antibody-conjugates permitting target cell-specific endosomal escape, localization to the nucleus and enhanced total intracellular accumulation. *Molecular Pharmaceutics*, 13(6): 1915-26.
Beaudoin et al., (2018). Initial Evaluation of Antibody-conjugates Modified with Viral-derived Peptides for Increasing Cellular Accumulation and Improving Tumor Targeting. *Journal of Visualized Experiments*, 133: 55440. doi: 10.3791/55440.
Hanafi et al., (2018). Overview of Bile Acids Signaling and Perspective on the Signal of Ursodeoxycholic Acid, the Most Hydrophilic Bile Acid, in the Heart. *Biomolecules*, 8(4): 159.
Lacasse et al., (2020). A Novel Proteomic Method Reveals NLS Tagging of T-DM1 Contravenes Classical Nuclear Transport in a Model of HER2-Positive Breast Cancer. *Molecular Therapy: Method & Clinical Development*, 19:99-119. doi: 10.1016/j.omtm.2020.08.016.
Linke et al, (2001). Stimulation of acid sphingomyelinase activity by lysosomal lipids and sphingolipid activator proteins. *Biological Chemistry*. 382(2):283-90. doi: 10.1515/BC.2001.035.
Murakami et al., (2020). Bile acids and ceramide overcome the entry restriction for GII.3 human norovirus replication in human intestinal enteroids. *Proceedings of the National Academy of Sciences USA*. 117(3):1700-1710.
Paquette et al., (2018). NLS-Cholic Acid Conjugation to IL-5Rα-Specific Antibody Improves Cellular Accumulation and In Vivo Tumor-Targeting Properties in a Bladder Cancer Model. *Bioconjugate Chemistry*. 29:1352-1363.
Patel et al., (2017). Next generation approaches for tumor vaccination. *Chinese Clinical Oncology*. 6(2):19.

(Continued)

*Primary Examiner* — Stacy B Chen
(74) *Attorney, Agent, or Firm* — Medlen & Carroll, LLP

(57) ABSTRACT

Covalently modified polypeptide antigens having improved immunogenicity and/or stability, as well as compositions, cells, and methods relating thereto, are described herein. Polypeptide antigens are covalently conjugated to a one or more of steroid acid moieties to improve their stability and/or to trigger improved cellular immunity, or improved cellular and humoral immunity, against the antigen upon administration to a subject. The steroid acids include bile acids and bile acid analogs that enhance endocytosis and/or endosomal escape of endosomally trapped cargoes by potentiating enzymatic cleavage of sphingomyelin to ceramide within endosomal membranes. The steroid acid moieties may be pre-conjugated to a peptide, and the steroid acid-peptide moiety subsequently conjugated to the polypeptide antigen. The peptide may comprise one or more domains that impart an additional functionality to the modified polypeptide antigen.

15 Claims, 37 Drawing Sheets

Specification includes a Sequence Listing.

(56) References Cited

OTHER PUBLICATIONS

Shivanna et al., (2014) The crucial role of bile acids in the entry of porcine enteric calicivirus. *Virology* 456-457, 268-278.

Shivanna et al., (2015). Ceramide formation mediated by acid sphingomyelinase facilitates endosomal escape of caliciviruses. *Virology*, 483, 218-228.

Smith et al., (2019). Alternative tumour-specific antigens. *Nature Review Cancer.* 19(8): 465-478.

Sun et al., (2016). Factors influencing the nuclear targeting ability of nuclear localization signals. *Journal of Drug Targeting*, 24(10): 927-933.

Swaan et al., (1997). Enhanced Transepithelial Transport of Peptides by Conjugation to Cholic Acid. 8: 520-525.

Tagliamonte et al., (2014). Antigen-specific vaccines for cancer treatment. *Human Vaccines & Immunotherapeutics*, 10(11): 3332-3346.

Al-Hilal et al., "Functional transformations of bile acid transporters induced by high-affinity macromolecules," Scientific Reports 4:4163, 9 pages (2014).

Beaudoin et al., (2016). Antibodies with integrated endosome escape and multi directional intracellular trafficking control capabilities for molecular transport and accumulation of a BODIPY based dye. *J Nucl Med*,vol. 57 No. supplement 2 1215.

Beck et al., (2017). Strategies and challenges for the next generation of antibody-drug conjugates. *Nature Reviews Drug Discovery*, 16: 315-337.

Chang et al. (2004) "Bile acids are essential for porcine enteric calicivirus replication in association with down-regulation of signal transducer and activator of transcription 1", PNAS, vol. 101, No. 23.

Chugh et al. (2010) "Cell-Penetrating Peptides: Nanocarrier for Macro molecule Delivery in Living Cells", IUBMB Life, 62 (3): 183-193.

De Loos, M. et al.1 (2005). Design and Application of Self-Assembled Low Molecular Weight Hydrogels. *Eur. J. Org. Chem.*, 3615-3631.

El-Kadiry et al., (2022), Accum™ Technology: A Novel Conjugable Primer for Onco-Immunotherapy. *Molecules*, 27(12): 3807, doi: 10.3390/molecules27123807.

Kenney and Meng (2015). "Identification and Fine Mapping of Nuclear and Nucleolar Localization Signals within the Human Ribosomal Protein S17", PLoS One Apr. 8, 2015;10(4):e0124396.

Kim et al. (2012) "Homodimeric SV40 NLS peptide formed by disulfide bond as enhancer for gene delivery", Bioorganic & Medicinal chemistry letters, vol. 22, pp. 5415-5418.

Kim et al. (2017) "The molecular mechanism for nuclear transport and its application", Anat Cell Biol; 50: 77-85.

Kosugi et al. (2009) "Six Classes of Nuclear Localization Signals Specific to Different Binding Grooves of Importin", J. Biol. Chem. 2009, 284: 478-485.

Liu et al., (2020), The Renpenning syndrome-associated protein PQBP1 facilitates the nuclear import of splicing factor TXNL4A through the karyopherin 2 receptor. Journal of Biological Chemistry, 295(13): 4093-4100.

Lam and Dean, (2010) "Progress and prospects: nuclear import of nonviral vectors", Gene Therapy, 2010, 17, 439-447.

Leyton et al. (2011) "Auger Electron Radioimmunotherapeutic Agent Specific for the CD123+/CD131—Phenotype of the Leukemia Stem Cell Population." The Journal of Nuclear Medicine, vol. 52, No. 9, 1465-1473.

Lu, J. et al., (2021). Types of nuclear localization signals and mechanisms of protein import into the nucleus. *Cell Commun Signal* 19:60.

Manoharan et al. (1994) "Cholic Acid—Oligonucleotide Conjugates for Antisense Applications", Bioorganic and Medicinal Chemistry Letter, vol. 4, No. 8, 1053-1060.

Ogris et al., (2001). Melittin enables efficient vesicular escape and enhanced nuclear access of nonviral gene delivery vectors. Journal of Biological Chemistry, 276(50): 47550-5.

Paquette et al., (2016). ChAcNLSA14, a novel antibody conjugate PET tracer for targeting human IL 5Rα-positive muscle invasive bladder cancer. *J Nucl Med*, vol. 57 No. supplement 2 52.

Raouane et al. (2012) "Lipid Conjugated Oligonucleotides: A Useful Strategy for Delivery", Bioconjugate Chemisrty, vol. 23, pp. 1091-1104.

Ray et al. (2015) "Quantitative tracking of protein trafficking to the nucleus using cytosolic protein delivery by nanoparticle-stabilized nanocapsules" Bioconjug Chem. Jun. 17, 2015; 26 (6): 1004-1007. doi : 10.1021/acs.bioconjchem.5b00141.

Sangeetha, N. M. et al., (2004). Properties of Hydrogels Derived from Cationic Analogues of Bile Acid: Remarkably Distinct Flowing Characteristics. *J. Phys. Chem. B*, 108, 16056-16063.

Tomatsidou (2013) "Evaluation of peptide-mediated nucleic acid delivery", Department of Pharmaceutics, Utrecht Institute of Pharmaceutical Sciences (UIPS), Utrecht University, 2013, pp. 1-33.

Wang et al., (2020). HMGB 1 in inflammation and cancer. Journal of Hematology & Oncology, 13:116.

Pavlovic, N. et al. (2018) "Bile Acids and Their Derivatives as Potential Modifiers of Drug Release and Pharmacokinetic Profiles" Frontiers in Pharmacology, Nov. 2018, vol. 9, Article 1283.

Raucher, D. et al. (2015) "Cell-penetrating peptides: strategies for anticancer treatment", Trends Mol Med. Sep. 2015;21(9):560-70.

Pavlović, N. et al. (2018) "Bile Acids and Their Derivatives as Potential Modifiers of Drug Release and Pharmacokinetic Profiles," *Frontiers in Pharmacology 9* published Nov. 8, 2018.

Martinez, J. D. et al. (1998) "Different bile acids exhibit distinct biological effects: The tumor promoter deoxycholic acid induces apoptosis and the chemopreventive agent ursodeoxycholic acid inhibits cell proliferation," *Nutrition and Cancer* 31(2), 111-118 published Jan. 1, 1998.

Raucher, D. et al. (2015) "Cell-penetrating peptides: strategies for anticancer treatment," *Trends in Molecular Medicine* 21(9), 560-570.

Fig. 1C

```
GSIGAASMEFCFDVFKELKVHHANENIFYCPIAIMSALAMVYLGAK
DSTRTQINKVVRFDKLPGFGDSIEAQCGTSVNVHSSLRDILNQITK
PNDVYSFSLASRLYAEERYPILPEYLQCVKELYRGGLEPINFQTAA
DQARELINSWVESQTNGIIRNVLQPSSVDSQTAMVLVNAIVFKGLW
EKAFKDEDTQAMPFRVTEQESKPVQMMYQIGLFRVASMASEKMKIL
ELPFASGTMSMLVLLPDEVSGLEQLESIINFEKLTEWTSSNVMEER
KIKVYLPRMKMEEKYNLTSVLMAMGITDVFSSSANLSGISSAESLK
ISQAVHAAHAEINEAGREVVGSAEAGVDAASVSEEFRADHPFLFCI
KHIATNAVLFFGRCVSP
```

(SEQ ID NO: 2)

Fig. 1D

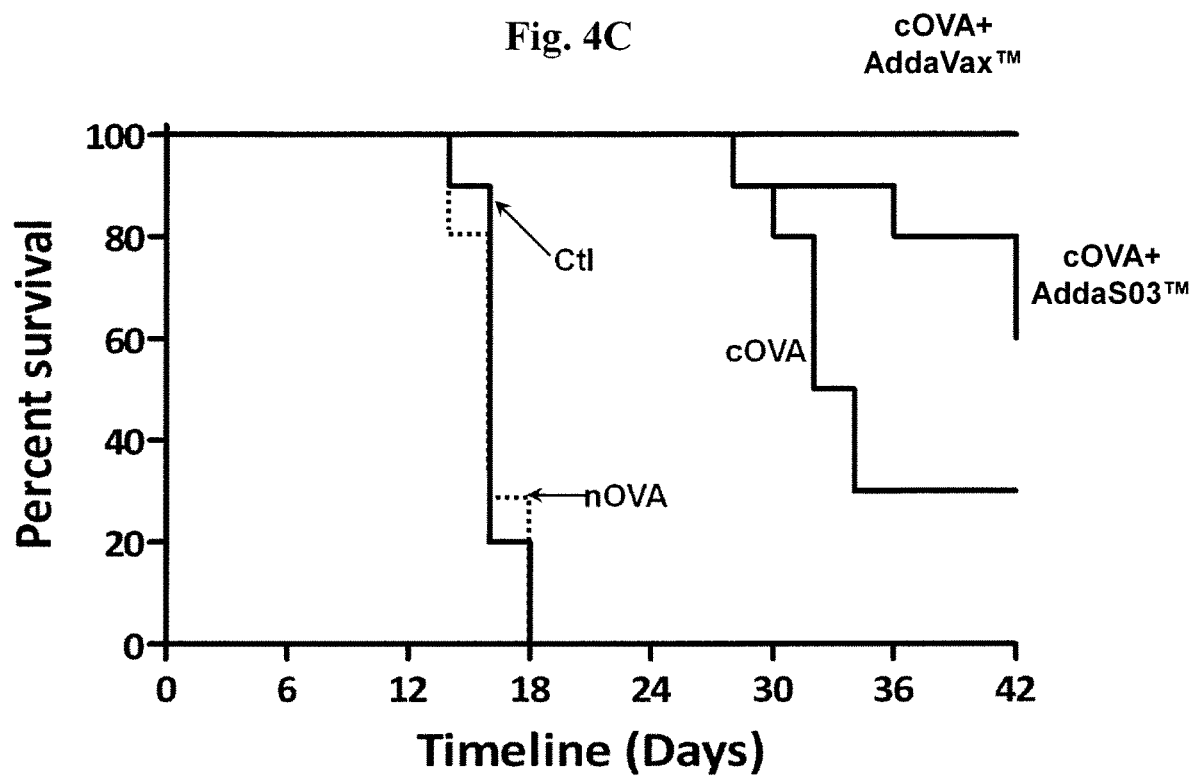
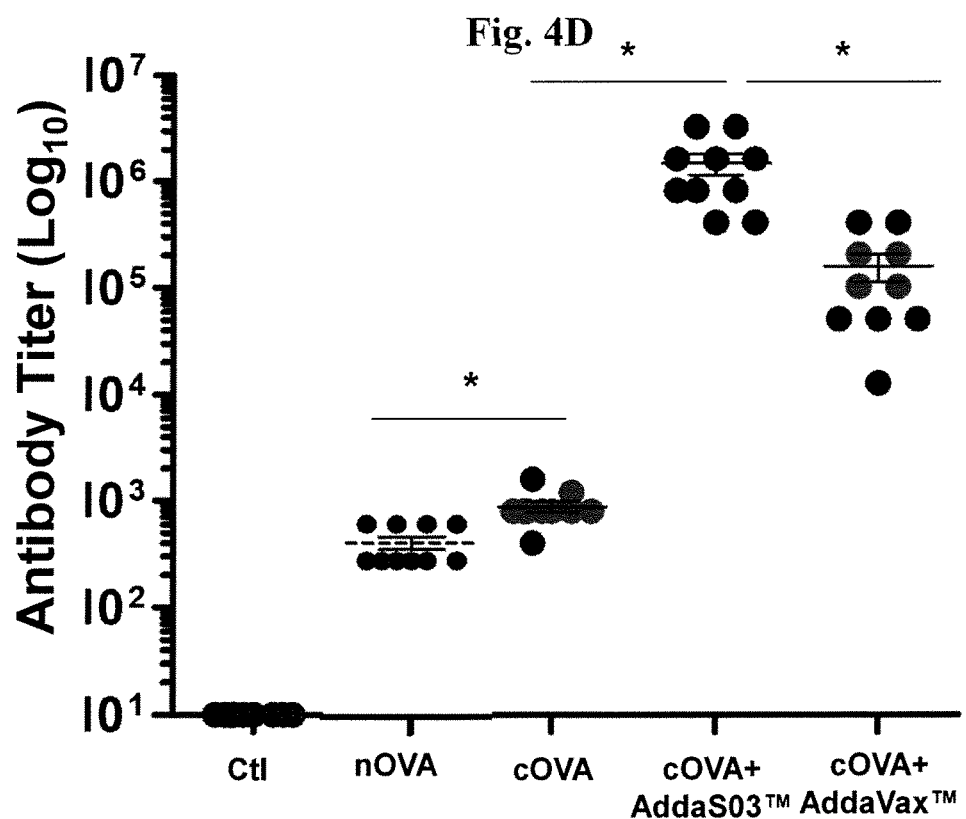

Fig. 7A

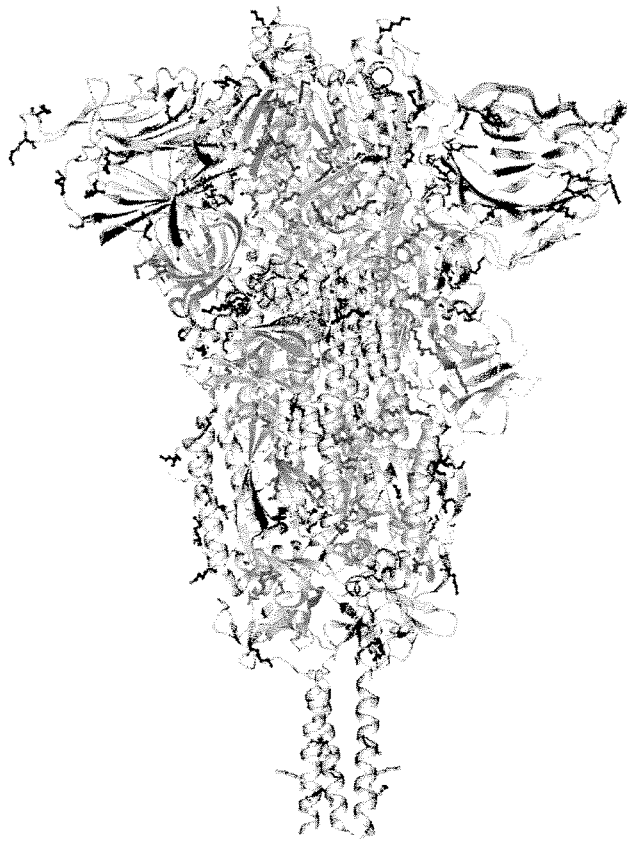

Fig. 7B (SEQ ID NO: 3)

MFVFLVLLPLVSSQCVNLTTRTQLPPAYTNSFTRGVYYPDKVFRSSVLHSTQDLFLPFFSNVTWFHAIHVS
GTNGTKRFDNPVLPFNDGVYFASTEKSNIIRGWIFGTTLDSKTQSLLIVNNATNVVIKVCEFQFCNDPFLG
VYYHKNNKSWMESEFRVYSSANNCTFEYVSQPFLMDLEGKQGNFKNLREFVFKNIDGYFKIYSKHTPINLV
RDLPQGFSALEPLVDLPIGINITRFQTLLALHRSYLTPGDSSSGWTAGAAAYYVGYLQPRTFLLKYNENGT
ITDAVDCALDPLSETKCTLKSFTVEKGIYQTSNFRVQPTESIVRFPNITNLCPFGEVFNATRFASVYAWNR
KRISNCVADYSVLYNSASFSTFKCYGVSPTKLNDLCFTNVYADSFVIRGDEVRQIAPGQTGKIADYNYKLP
DDFTGCVIAWNSNNLDSKVGGNYNYLYRLFRKSNLKPFERDISTEIYQAGSTPCNGVEGFNCYFPLQSYGF
QPTNGVGYQPYRVVVLSFELLHAPATVCGPKKSTNLVKNKCVNFNFNGLTGTGVLTESNKKFLPFQQFGRD
IADTTDAVRDPQTLEILDITPCSFGGVSVITPGTNTSNQVAVLYQGVNCTEVPVAIHADQLTPTWRVYSTG
SNVFQTRAGCLIGAEHVNNSYECDIPIGAGICASYQTQTNSPRRARSVASQSIIAYTMSLGAENSVAYSNN
SIAIPTNFTISVTTEILPVSMTKTSVDCTMYICGDSTECSNLLLQYGSFCTQLNRALTGIAVEQDKNTQEV
FAQVKQIYKTPPIKDFGGFNFSQILPDPSKPSKRSFIEDLLFNKVTLADAGFIKQYGDCLGDIAARDLICA
QKFNGLTVLPPLLTDEMIAQYTSALLAGTITSGWTFGAGAALQIPFAMQMAYRFNGIGVTQNVLYENQKLI
ANQFNSAIGKIQDSLSSTASALGKLQDVVNQNAQALNTLVKQLSSNFGAISSVLNDILSRLDKVEAEVQID
RLITGRLQSLQTYVTQQLIRAAEIRASANLAATKMSECVLGQSKRVDFCGKGYHLMSFPQSAPHGVVFLHV
TYVPAQEKNFTTAPAICHDGKAHFPREGVFVSNGTHWFVTQRNFYEPQIITTDNTFVSGNCDVVIGIVNNT
VYDPLQPELDSFKEELDKYFKNHTSPDVDLGDISGINASVVNIQKEIDRLNEVAKNLNESLIDLQELGKYE
QYIKWPWYIWLGFIAGLIAIVMVTIMLCCMTSCCSCLKGCCSCGSCCKFDEDDSEPVLKGVKLHYTLESGG
GSAWSHPQFEKGGGSGGGSGGSSAWSHPQFEK

Fig. 8E nSpike-CoV-2 cSpike-CoV-2

☐ cSpike-CoV-2 Alone
■ cSpike-CoV-2 + AddaSO3™
▨ cSpike-CoV-2 + AddaVAX™

- ☐ cSpike-CoV-2 Alone
- ■ cSpike-CoV-2 + AddaSO3™
- ▨ cSpike-CoV-2 + AddaVAX™

COVALENTLY MODIFIED ANTIGENS FOR IMPROVED IMMUNE RESPONSE AND/OR STABILITY

CROSS-REFERENCE TO RELATED APPLICATIONS

The present application claims the benefit of U.S. Provisional Patent Application Nos. 63/202,047, filed May 25, 2021 and 63/127,731 filed Dec. 18, 2020, respectively, which are incorporated herein by reference.

FIELD OF THE INVENTION

The present description relates to covalently modified antigens to enhance or modify their immunogenicity and/or stability. More specifically, the present description relates to polypeptide antigens covalently conjugated to one or more steroid acid moieties for improved cellular immunity and/or improved thermal stability.

BACKGROUND

While subunit vaccines based on polypeptide antigens are generally considered amongst the safest vaccines, such antigens may not elicit sufficiently strong immune responses to provide protective and long-lasting immunity. Furthermore, while the use of mRNA-based vaccines in response to the COVID-19 pandemic has garnered much attention, their relatively poor stability and strict refrigeration requirements is a hurdle to their deployment on a global scale. Thus, methods of improving the immunogenicity, efficacy, and stability of polypeptide antigen-based vaccines would be highly desirable.

SUMMARY

In a first aspect, described herein is a method of improving polypeptide antigen immunogenicity and/or stability, the method comprising providing a polypeptide antigen to be modified, and covalently conjugating the polypeptide antigen to one or more steroid acid moieties to produce a modified polypeptide antigen. In some embodiments, the modified polypeptide antigen is conjugated to a sufficient number of steroid acid moieties to increase endosomal escape of the modified polypeptide antigen upon intracellular delivery relative to a polypeptide antigen lacking said modification, wherein the modified polypeptide antigen triggers an improved adaptive immune response to said polypeptide antigen upon administration to a subject as compared to a corresponding unmodified polypeptide antigen. In some embodiments, the modified polypeptide antigen is conjugated to a sufficient number of steroid acid moieties such that the modified polypeptide antigen exhibits greater stability than that of the polypeptide antigen prior to conjugation.

In further aspects, described herein is a population of cells (e.g., in vitro or ex vivo) comprising a modified polypeptide antigen as described herein, or an immunogenic composition comprising: a modified polypeptide antigen and/or population of cells as described herein; and a pharmaceutically acceptable excipient and/or adjuvant.

In a further aspect, described herein is a method for triggering an enhanced adaptive immune response in a subject against an unmodified polypeptide antigen of interest, the method comprising administering an immunogenic composition as described herein to the subject.

In a further aspect, described herein is a method for treating or preventing a disease or disorder amenable to treatment by vaccination and/or immunotherapy, the method comprising administering an immunogenic composition as described herein to the subject.

In a further aspect, described herein is a method for vaccinating a subject against an infectious disease, the method comprising administering an immunogenic composition described herein to the subject, wherein the polypeptide antigen comprises an antigenic fragment of a pathogen (e.g., virus, bacteria, fungus) causing the infectious disease.

In a further aspect, described herein is a method for treating or preventing a disease or disorder amenable to treatment by vaccination and/or immunotherapy, the method comprising administering an immunogenic composition as described herein to the subject.

In a further aspect, described herein is a method for treating cancer in a subject, the method comprising administering an immunogenic composition as described herein to the subject.

In a further aspect, described herein is a modified polypeptide antigen as described herein for use in generating an immune response in a subject or for the manufacture of an immunogenic composition for generating an immune response in a subject.

In a further aspect, described herein is a method for preparing a polypeptide antigen, the method comprising conjugating an unmodified polypeptide antigen to a sufficient number of steroid acid moieties to produce a modified polypeptide antigen that exhibits greater stability (e.g., thermal stability) than that of the polypeptide antigen prior to conjugation.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one," but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the expression "consisting essentially of" or "consists essentially of" refers to those elements required for a given embodiment. The expression permits the presence of additional elements that do not materially affect the basic and novel or functional characteristic(s) of that embodiment of the invention. In the context of modified polypeptide antigens described herein, the expressions "consisting essentially of" or "consists essentially of" refer to the elements required to improve polypeptide antigen immunogenicity as compared to an unmodified antigen (e.g., by improving antigen presentation by professional antigen-presenting cells). For greater clarity, the expressions do not exclude the possibility that other additional non-essential ingredients (e.g., excipients, fillers, stabilizers, or inert components) that do not materially change the function or ability of the steroid acid-peptide moieties to improve polypeptide antigen immunogenicity.

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1A-H shows the biochemical characterization of the ChAcNLS-antigen formulation. FIG. 1A is a schematic diagram representing covalent binding of a given antigen to a ChAcNLS moiety. FIG. 1B shows a representative Coomassie blue staining displaying unmodified OVA (line 1), or ChAcNLS conjugated to OVA at a molar ratio of 25× (line 2) or 50× (line 3). FIG. 1C shows the amino acid sequence of chicken OVA. Lysine residues that are predicted to be accessible for ChAcNLS conjugation (>50%) are highlighted in black. The three lysine residues predicted to be weakly accessible are underlined. FIG. 1D shows a ribbon structure of the OVA protein with lysine residues that are predicted to be highly (dark), moderate or poorly (light) accessible lysine residues. FIG. 1E shows a representative Western blot displaying unmodified OVA (line 1), ChAcNLS-OVA at a ratio of 25× (line 2), and ChAcNLS-OVA at a ratio of 50× (line 3). FIG. 1F shows an intrinsic tryptophan fluorescence (ITF) analysis of nOVA or ChAcNLS-OVA (cOVA) at various ChAcNLS to OVA ratios in response to thermal stress. FIGS. 1G and 1H shows the effect of various cOVA variants on the efficacy of antigen presentation by DCs. FIG. 1G shows a representative schematic diagram of the different variants tested in FIG. 1H. FIG. 1H shows the response quantification using the SIIN-FEKL-specific B3Z cell line co-cultured with DCs treated with the different variants. For this panel, n=5/group with *** p<0.001 when compared to the nOVA group.

FIG. 2A shows schematically the antigen classical (MHC-II) and cross-presentation (MHC-I) assays used to assess OVA-responding OT-I (CD8) and OT-II (CD4) T cells. FIG. 2B shows the IFN-gamma produced by OT-I-derived CD8 T cells incubated with DCs and either naked OVA (nOVA) or ChAcNLS-OVA (cOVA). FIG. 2C shows the IL-2 levels produced by OT-II-derived CD4 T cells incubated with DCs and either naked OVA (nOVA) or ChAcNLS-OVA (cOVA). FIG. 2D shows the IFN-gamma production for the experiment of FIG. 2C. FIG. 2E shows the results of a representative flow-cytometry experiment investigating OVA-DQ™ (dark grey peak) versus ChAcNLS-OVA-DQ (light gray peak) processing by DCs at different time points. FIG. 2F shows the quantification of the mean fluorescent intensity (MFI) of the OVA-DQ/ChAcNLS-OVA-DQ signals shown in FIG. 2E. For this experiment, n=5/group with ***p<0.001. FIG. 2G shows a representative experiment of Gal3-GFP-expressing DC2.4 cells treated with nOVA (upper pictogram) versus cOVA (lower pictogram). White arrows point to some of the damaged endosomes.

FIG. 3A is a schematic representation of the timeline used for prophylactic vaccination using the OVA protein. FIG. 3B-3C shows assessment of tumor growth volume (FIG. 3B) and survival (FIG. 3C) of animals challenged with the EG.7 tumor following prophylactic vaccination using naked OVA (nOVA)- or ChAcNLS-OVA (cOVA)-pulsed DCs. Non-immunized mice injected with EG.7 are shown as "Ctl". FIG. 3D shows the antibody titers of vaccinated animals quantified by ELISA. FIG. 3E shows the quantification of central memory ($T_{cm}$) and effector memtory ($T_{eff}$) CD4 T cells derived from mice immunized with nOVA-/cOVA-pulsed DCs from vaccinated animals of this study. FIG. 3F shows the quantification of central memory ($T_{cm}$) and effector memtory ($T_{eff}$) CD8 T cells derived from mice immunized with nOVA-/cOVA-pulsed DCs from vaccinated animals of this study. FIG. 3G shows the Luminex™ analysis of cytokine/chemokine production in response to in vitro re-stimulation of T cells isolated from vaccinated animals of this study. Cytokines/chemokines with the highest fold change were boxed. For panels FIGS. 3B, 3C, 3D and 3E, n=10/group with ***P<0.001.

FIG. 4A-D shows the immunity assessment following direct injection of the OVA protein. FIG. 4A is a schematic representation of the timeline used for prophylactic vaccination using the OVA protein with or without vaccine adjuvants. FIG. 4B shows average tumor measurements in animals immunized using naked OVA (nOVA) (1 µg), ChAcNLS-OVA (cOVA) cOVA (1 µg) with AddaS03™ adjuvant, and cOVA (1 µg) with AddaVax™ adjuvant. Non-immunized mice injected with EG.7 are shown as "Ctl". FIG. 4C shows the survival results from the experiment shown in FIG. 4A. FIG. 4D shows quantification of antibody titers from the experiment shown in FIG. 4A. For this experiment, n=10/group with *P<0.05.

FIG. 5A is a schematic representation of the timeline used for therapeutic vaccination. FIG. 5B-5C shows tumor growth volume (FIG. 5B) and survival (FIG. 5C) of animals challenged with the EG.7 tumor following syngeneic therapeutic vaccination using anti-PD-1 alone ("αPD-1"), naked OVA ("nOVA")- or ChAcNLS-OVA ("cOVA")-pulsed DCs, with ("αPD-1") or without anti-PD-1. Non-immunized mice injected with EG.7 are shown as "Ctl". FIG. 5D-5E show assessments of tumor growth volume (FIG. 5D) and survival (FIG. 5E) of animals challenged with the EG.7 tumor following allogeneic therapeutic vaccination anti-PD-1 (dashed), ChAcNLS-OVA ("cOVA")-pulsed DCs with anti-PD-1 at varying cell numbers (3K; 30K, 100K; 300K) or without anti-PD-1(300K). For all panels, n=10/group.

FIG. 6A is schematic representation of the timeline used for allogeneic therapeutic vaccination. FIG. 6B-6C shows assessments of tumor growth volume (FIG. 6B) and survival (FIG. 6C) of animals challenged with the EL4 tumor following immunization with anti-PD-1 (dashed; "αPD-1"), BALB/c-derived allogeneic DCs pulsed with EL4 lysate or EL4-ChAcNLS lysate ("cLysate"), with (EL4 lysate; EL4-ChAcNLS lysate) or without (EL4 lysate; EL4-ChAcNLS lysate) anti-PD-1 treatment (n=10/group). Non-immunized mice injected with EG.7 are shown as "Ctl". FIG. 6D shows a schematic representation of the experimental design of the tumor-infiltrating lymphocytes (TILs) study. FIG. 6E shows an analysis of various immune cells in tumors derived from all groups shown in FIGS. 6B and 6C. FIG. 6F shows the assessment of the CD8/Treg ratio in the tumors depicted in FIGS. 6B and 6C. For FIGS. 6B and 6C, n=10/group. For FIGS. 6E-6F, n=5/group with 772 *P<0.05, P<0.01, and *P<0.001.

FIG. 7A-B shows the SARS-CoV-2 Spike protein used for the formulation of ChAcNLS-Spike-CoV-2. FIG. 7A shows a schematic diagram of the ribbon structure of SARS-CoV-2 Spike protein (Wuhan strain with D614G mutation) with lysine residues that are predicted to be highly (dark), moderate or poorly (light) accessible lysine residues. FIG. 7B shows the amino acid sequence of SARS-CoV-2 Spike protein. Lysine residues that are predicted to be accessible for ChAcNLS conjugation (>50%) are highlighted in black. The lysine residues predicted to be weakly accessible are underlined.

FIG. 8A-E shows the evaluation of immunogenicity of the ChAcNLS-Spike-CoV-2 vaccine using different CoV-2 Spike protein domains. FIG. 8A shows the antibody titers from mice vaccinated with the full-length "naked" Spike-CoV-2 (unconjugated; nSpike-CoV-2; black acid-NLS moieties (0.1 mg/mL). For this experiment, isolated B cells were used as antigen presenting cells in a B3Z reporter system. Controls tested included no antigen ("PBS") and antigen alone (i.e., unconjugated) ("OVA alone"; 5 mg/mL). $OD_{570}$ levels represent the level of OVA presentation, and the dashed line represents the signal obtained with the original ChAcNLS conjugated to OVA ("CA-SV40"). Bile acids: cholic acid (CA); glycodeoxycholic acid (GDCA); glycochenodeoxycholic acid (GCDCA); chenodeoxycholic acid (CDCA); ursodeoxycholic acid (UDCA); glycoursodeoxycholic acid (GUDCA); deoxycholic acid (DCA); glycocholic acid (GCA); and lithocholic acid (LCA).

SEQUENCE LISTING

Figure 1A:
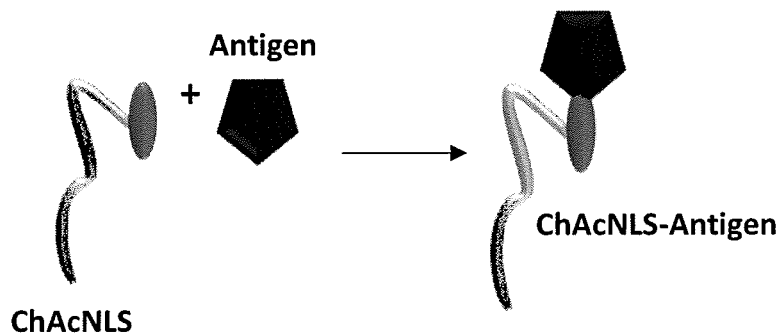

This application contains a Sequence Listing in computer readable form created Nov. 1, 2021. The computer readable form is incorporated herein by reference.

| SEQ ID NO: | Description |
| --- | --- |
| 1 | ChAcNLS |
| 2 | Chicken egg white ovalbumin (OVA) |
| 3 | SARS-CoV-2 Spike glycoprotein (Wuhan strain D614G) (NCBI Ref: 6XR8 A) |
| 4 | SARS-CoV Spike glycoprotein (Uniprot P59594) |
| 5 | OVA OT-I (CD8) peptide |
| 6 | OVA OT-II (CD4) peptide |
| 7 | NLS from SV-40 large T-antigen |
| 8 | GWG-SV40NLS |
| 9 | hnRNPA1 M9 NLS |
| 10 | hnRNP D NLS |
| 11 | hnRNP M NLS |
| 12 | PQBP-1 NLS |
| 13 | NLS2-RG Domain RPS17 |
| 14 | NLS1 RPS17 |
| 15 | NLS2 RPS17 |
| 16 | NLS3 RPS17 |
| 17 | cMyc NLS |
| 18 | HuR NLS |
| 19 | Tus NLS |
| 20 | Nucleoplasmin NLS |

DETAILED DESCRIPTION

Described herein are compositions, cells, and methods relating to improving or modifying the adaptive immune response to polypeptide antigens and/or to improving the stability of polypeptide antigens. In some aspects, the present invention stems from the demonstration herein that conjugating a polypeptide antigen to steroid acid moieties triggers improved cellular immunity, or improved cellular and humoral immunity, against the antigen. In some aspects, the present invention stems from the demonstration herein that conjugating a polypeptide antigen to steroid acid moieties improves the stability (e.g., against thermal stress) of the polypeptide antigen. In some embodiments, the polypeptide antigens described herein may be covalently conjugated via functionalized linkers to the steroid acid moieties or to steroid acid-peptide moieties. Advantageously, when the polypeptide antigens are conjugated to steroid acid-peptide moieties, the peptide may be designed to comprise one or more domains imparting a desired functionality to the modified polypeptide antigen (e.g., protein transduction and/or subcellular targeting), which may further enhance immunogenicity.

In a first aspect, described herein is a method for improving the immunogenicity of a polypeptide antigen. The method generally comprises selecting/providing a suitable polypeptide antigen to be modified, and covalently conjugating the polypeptide antigen to steroid acid moieties to produce a modified polypeptide antigen. In some embodiments, the modified polypeptide antigen is conjugated to a number of steroid acid moieties sufficient to increase the cellular and/or humoral immune response against the polypeptide antigen upon administration to a subject (e.g., as compared to a corresponding unmodified polypeptide antigen). In some embodiments, the modified polypeptide antigen is conjugated to a number of steroid acid moieties that is sufficient to increase endocytosis and/or endosomal escape of the modified polypeptide antigen (e.g., as compared to a corresponding unmodified polypeptide antigen) upon intracellular delivery. In some embodiments, the modified polypeptide antigen triggers an improved adaptive immune response (e.g., improved cellular and/or Immoral immune response) against the polypeptide antigen upon administration to a subject as compared to a corresponding unmodified polypeptide antigen.

Polypeptide antigens are normally captured by antigen-presenting cells (e.g., dendritic cells) but are initially entrapped in endosomes. Endosomal maturation towards lysosomes results in a decrease in pH and an activation of proteolytic enzymes that mediate non-specific antigen degradation. As a result, some of the antigen fragments generated may then pass through endosomal pores to reach the cytosol where further antigen degradation takes place by the proteasomal machinery prior to MHC class I presentation. Although this process occurs naturally, the generated antigen fragments that ultimately leave the endosomes may be small and/or damaged, rendering them unsuitable for proteasomal degradation, thereby precluding their MHC class I presentation and thus cellular immunity based thereon. Without being bound by theory, the increased endosomal escape of the modified polypeptide antigens described herein may enable antigens (or larger antigen fragments) to reach the cytosol in a more native conformation. As a result, proteasomal degradation of these more native antigens may result in a higher number of immunogenic and/or stable peptides presented via MHC class I at the surface of antigen-presenting cells, thereby eliciting potent T-cell activation.

As used herein, "polypeptide antigen" refers to an immunogenic peptide-linked chain of amino acids of any length, but generally at least 8, 9, 10, 11, or 12 amino acids long. For greater clarity, polypeptide antigens referred to herein exclude antigen-binding antibodies or fragments thereof. As used herein, a "protein antigen" refers to a polypeptide antigen having a length of at least 50 amino acid residues, while a "peptide antigen" refers to a polypeptide antigen having a length of less than 50 amino acid residues. For greater clarity, polypeptides, proteins, and peptides described herein may or may not comprise any type of modification (e.g., chemical or post-translational modifications such as acetylation, phosphorylation, glycosylation, sulfatation, sumoylation, prenylation, ubiquitination, etc.) or incorporate one or more synthetic or non-natural amino acids, to the extent that the modification or synthetic or non-natural amino acids does not destroy the antigenicity of the polypeptide antigen or the desired functionality of the peptide (or domain comprised therein).

Figure 1B:
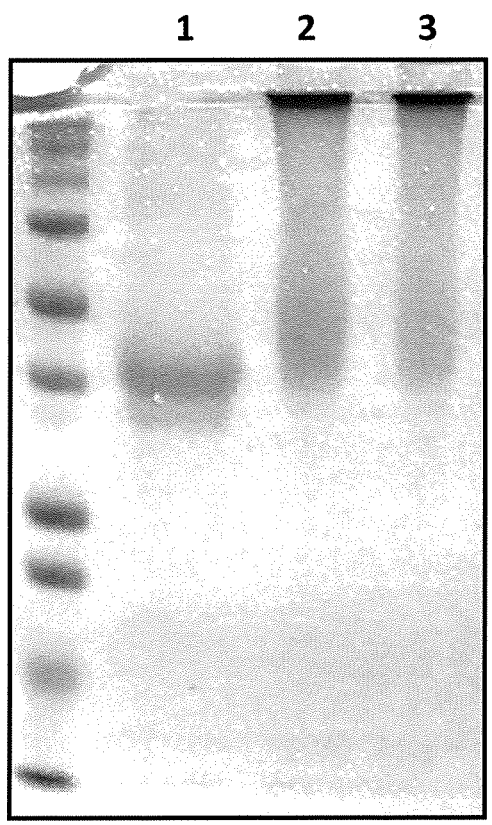
Figure 1E:
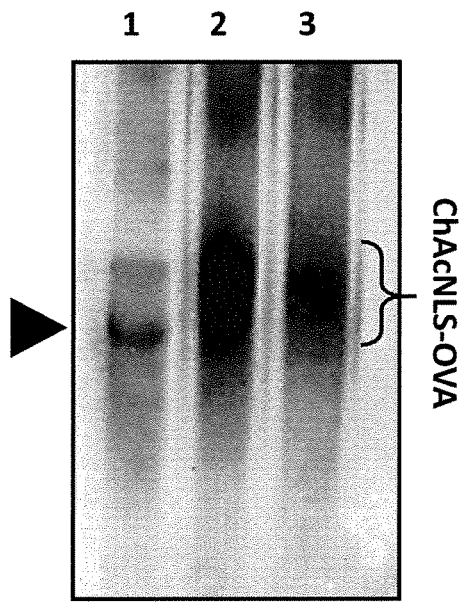
Figure 1F:
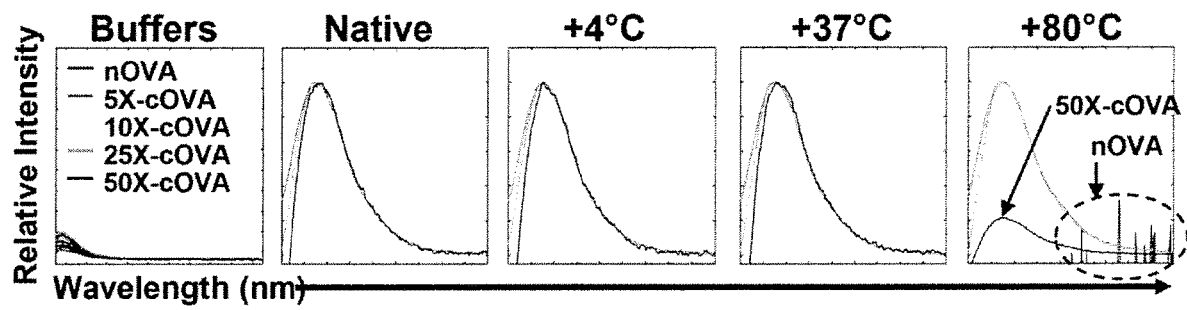
Figure 1G:
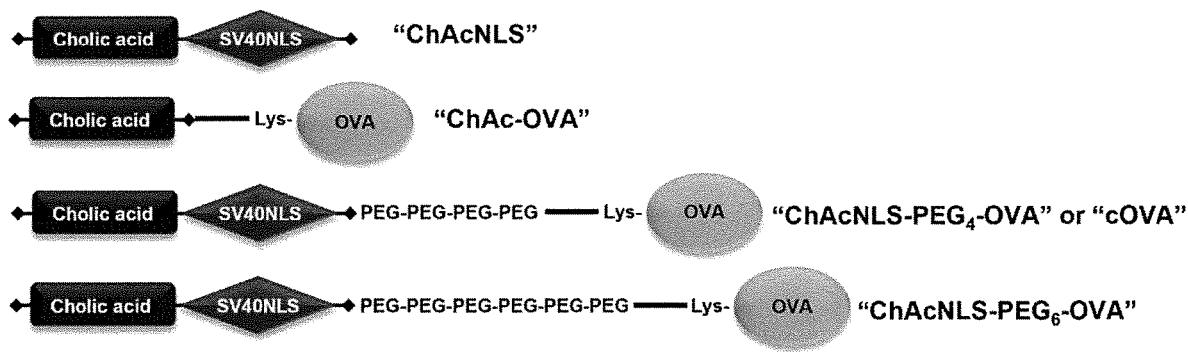
Figure 1H:
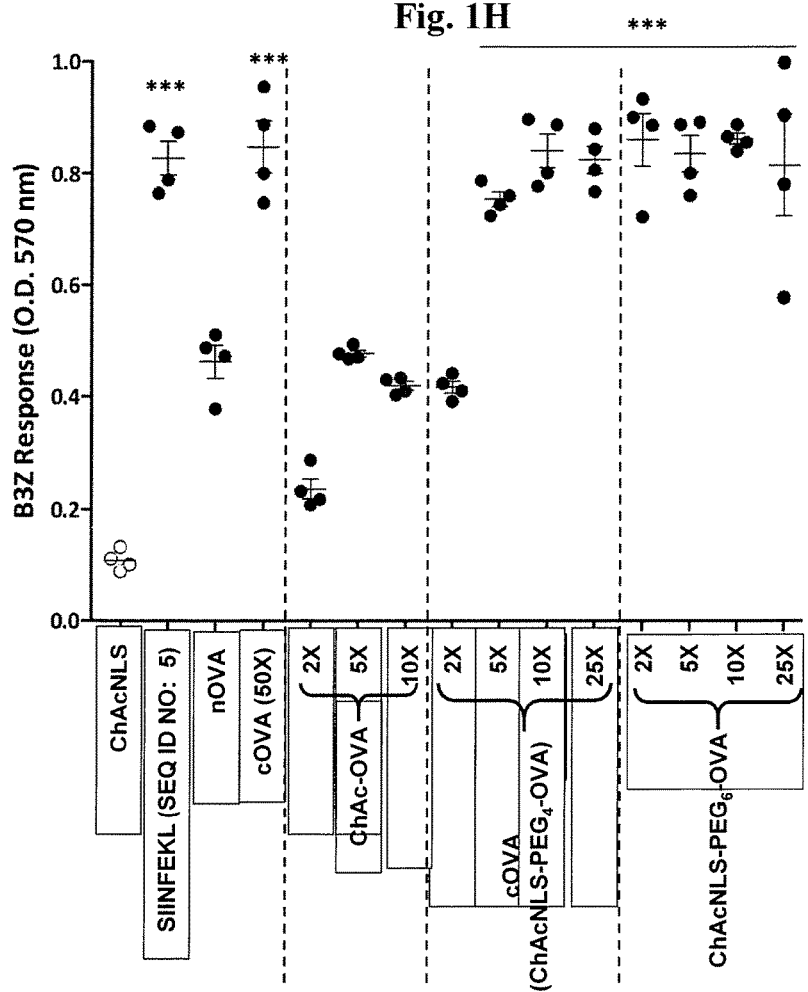

In some embodiments, modified polypeptide antigens described herein may be conjugated to a sufficient number of steroid acid moieties such that the modified polypeptide antigen exhibits greater stability (e.g., thermal stability) than that of the polypeptide antigen prior to conjugation (Example 2 and FIGS. 1G and 1H).

In some embodiments, polypeptide antigens described herein may be a protein antigen. In some embodiments, protein antigens may advantageously comprise a plurality of available functional groups to which the steroid acid or steroid acid-peptide moieties may be conjugated. In contrast, peptide antigens may not comprise a sufficient number of functional groups for steroid acid conjugation. Furthermore, steroid acid-peptide antigen conjugates may undesirably self-assemble into rod-like nanoparticles, as reported in Azuar et al., 2019, in which the hydrophobic steroid acid groups from different modified peptide antigens aggregate and are sequestered internally, thereby preventing their ability to interact with the membrane and mediate endosomal escape. Insufficient endosomal escape may not negatively affect MHC class II presentation and thus may benefit humoral immunity, but is unlikely to benefit cellular immunity (Azuar et al., 2019).

In some embodiments, the protein antigens described herein may comprise (or may be engineered to comprise) between 1 to 50, 2 to 50, 5 to 50, or 10 to 50 functional groups (e.g., lysine and/or cysteine residues: or any other group) available for conjugation to the steroid acid or steroid-peptide moieties described herein. In some embodiments, the polypeptide antigen may be a protein antigen at least 50, 55, 60, 65, 70, 75, 80, 85, 90, 95, 100, 105, 110, 115, 120, 125, 130, 135, 140, 145, or 150 amino acids in length. In some embodiments, the polypeptide antigen may be a protein antigen having a molecular weight of at least 10, 15, 20, 25, 30, 35, 40, 45, 50, 55, 60, 65, 70, 75, 80, 85, 90, 95, 100, 105, 110, 115, 120, 125, 130, 135, 140, 145, or 150 kDa. In some embodiments, the polypeptide antigens described herein may comprise one or more MHC class I epitopes and/or MHC class II epitopes.

In some embodiments, polypeptide antigens described herein may be or may comprise a tumor-associated antigen (TAA), tumor-specific antigen (TSA), a neoantigen, a viral antigen, a bacterial antigen, a fungal antigen, an antigen associated with a disease or disorder amenable to treatment by vaccination and/or immunotherapy; or any antigenic fragment thereof. In some embodiments, polypeptide antigens described herein may be or may comprise the Spike protein from SARS-CoV-2 (SEQ ID NO: 3) or SARS-CoV (SEQ ID NO: 4), or an antigenic variant or antigenic fragment thereof. In some embodiments, the TAA, TSA, and/or neoantigen may be a single-nucleotide variant antigen, a mutational frameshift antigen, splice variant antigen, a gene fusion antigen, an endogenous retroelement antigen, or another class of antigen, such as a human leukocyte antigen (HLA)-somatic mutation-derived antigen or a post-translational TSA (Smith et al., 2019). In some embodiments, the TSA may be a viral-derived cancer antigen, such as from human papillomavirus (HPV), cytomegalovirus, or Epstein-Barr virus (EBV). In some embodiments, the TAA may be or may comprise a cancer-testis antigen, HER2, PSA, TRP-1, TRP-2, EpCAM, GPC3, CEA, MUC1, MAGE-A1, NY-ESO-1, SSX-2, mesothelin (MSLN), or EGFR (Patel et al., 2017; Tagliamonte et al., 2014). In some embodiments, polypeptide antigens described herein may be or may comprise cell lysates or other material derived from a tumor such as tumor-derived exosomes.

In some embodiments, the polypeptide antigens may be conjugated to a steroid acid moiety that enhances endocytosis and/or endosomal escape of internalized cargoes. Without being bound by theory, steroid acids (e.g., bile acids and bile acid analogs) have been shown to be utilized/exploited by viruses to facilitate their infection of host cells, such as by increasing their endocytic uptake and/or endosomal escape to gain access to the cytosol (Shivanna et al., 2014; Shivanna et al., 2015; Murakami et al., 2020). For example, bile acids have been shown to trigger the enzyme acid sphingomyelinase (ASM) to cleave sphingomyelin to ceramide on the inner leaflet of endosomes. Increased amounts of ceramide destabilize membranes and facilitate endosomal escape. In some embodiments, steroid acids suitable for conjugation to the polypeptide antigens described herein comprise those that trigger ceramide accumulation on the inner leaflet of endosomes, thereby destabilizing endosomal membranes and facilitating endosomal escape of the modified polypeptide antigen upon intracellular delivery. In some embodiments, steroid acids suitable for conjugation to the polypeptide antigens described herein comprise those that trigger increased acid sphingomyelinase (ASM)-mediated cleavage of sphingomyelin to form ceramide.

In some embodiments, a steroid acid suitable for conjugation to a polypeptide antigen described herein comprises or consists of a bile acid (e.g., a primary bile acid or a secondary bile acid). In some embodiments, the steroid acid may be or comprise: cholic acid (CA), chenodeoxycholic acid (CDCA), deoxycholic acid (DCA), lithocholic acid (LCA), glycodeoxycholic acid (GDCA), glycocholic acid (GCA), taurochofic acid (TCA), glycodeoxycholic acid (CDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), glycoursodeoxycholic acid (GCDCA), or any analog thereof that: induces endocytosis; triggers ceramide accumulation on the inner leaflet of endosomes; triggers increased acid sphingomyelinase (ASM)-mediated cleavage of sphingomyelin to form ceramide; and/or has a hydrophobicity greater than that of cholic acid.

Hydrophobic bile acids such as GCDCA, TCA, GCA, and CA (but not hydrophilic bile acids such as UDCA) were shown to increase GII.3 human norovirus infection and replication in host intestinal cells by enhancing endosomal uptake and endosomal escape via ASM-mediated ceramide accumulation on the apical membrane (Murakami et al., 2020). In some embodiments, a steroid acid suitable for conjugation to a polypeptide antigen described herein comprises or consists of a bile acid or bile acid analog that is more hydrophobic than cholic acid. In some embodiments, a steroid acid suitable for conjugation to a polypeptide antigen described herein comprises or consists of a bile acid or bile acid analog that is more hydrophobic than cholic acid (e.g., CDCA, DCA, LCA, TCA, TDCA, TCDCA, GCA, GDCA, or GCDCA; Hanafi et al., 2018).

In some embodiments, the average number of steroid acid moieties per modified polypeptide antigen may be modified, for example, based on the type of steroid acid and/or type of polypeptide antigen selected (e.g., amino acid length, structure, number of available functional groups). In some embodiments, the polypeptide antigen may be reacted with a molar excess of steroid acid or steroid acid-peptide moieties to maximize the number of steroid acid moieties conjugated. In some embodiments, the polypeptide antigen may be reacted with a limiting amount of steroid acid or steroid acid-peptide moieties to control or limit the number of steroid acid moieties conjugated. In some embodiments, each modified polypeptide antigen molecule may be conjugated to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 steroid acid moieties. In some embodiments, the modified polypeptide antigen molecule may be conjugated to the steroid acid (or steroid acid-peptide) moiety at solvent-accessible amine (e.g., primary amine) and/or sulfhydryl group of the polypeptide antigen. In some embodiments, the modified polypeptide antigen molecule may be conjugated to the steroid acid (or steroid acid-peptide) moiety at any other chemical or functional group present on or engineered into the polypeptide antigen. It is understood that the maximum number of steroid acid moieties comprised in a modified polypeptide antigen described herein is less than or equal to the number of available functional groups on the polypeptide antigen (or functionalized polypeptide antigen) available for conjugation. In some embodiments, the polypeptide antigen (and/or the steroid acid or steroid acid-peptide moiety) may be pre-functionalized for example with a bifunctional, trifunctional, or multi-functional linker group, prior to the reaction conjugating the polypeptide antigen to the steroid acid or steroid acid-peptide moiety.

In some embodiments, the steroid acids described herein may be comprised in a steroid acid-peptide moiety. In some embodiments, the steroid acid may be pre-conjugated to the peptide, for example at a free N-terminal amino group of the peptide or at some other functional group within the peptide. In some embodiments, the polypeptide antigen may then be conjugated to the steroid acid-peptide moiety via the peptide, such as at an N- or C-terminal residue of the peptide.

In some embodiments, the peptide may be a non-immunogenic peptide. In some embodiments, the peptide may be a water-soluble peptide, wherein conjugation of the peptide to the steroid acid increases the water solubility of the steroid acid-peptide moiety as compared to the steroid acid moiety alone. In some embodiments, the peptide may be a cationic peptide (e.g., that promotes interaction the plasma and/or endosomal membrane).

In some embodiments, the peptide may comprise one or more domains that impart an additional functionality to the modified polypeptide antigen. As used herein, a "domain" generally refers to a part of a protein having a particular functionality. Some domains conserve their function when separated from the rest of the protein, and thus can be used in a modular fashion. The modular characteristic of many protein domains can provide flexibility in terms of their placement within the peptides described herein. However, some domains may perform better when engineered at certain positions of the peptide (e.g., at the N- or C-terminal region, or therebetween). The position of the domain within its endogenous protein may be an indicator of where the domain should be engineered within the peptide.

In some embodiments, the peptide may comprise a protein transduction domain (PTD) that stimulates endocytosis, endosomal formation, or intracellular delivery in a non-cell-specific manner. In some embodiments, the peptide may comprise a subcellular targeting signal promoting targeting of the modified polypeptide antigen to a specific subcellular compartment. In some embodiments, the peptide may comprise a nuclear localization signal (NLS) that targets the modified polypeptide antigen to the nucleus. Interestingly, while targeting to the cytosolic compartment may be expected to be advantageous given that proteosome-mediated MHC class I peptide epitope processing occurs in the cytosol, results shown herein surprisingly demonstrate that modified polypeptide antigens comprising a nuclear localization signal triggered a striking increase in antigen immunogenicity. In some embodiments, the nuclear localization signals described herein may comprise or be derived from the NLS from SV-40 large T-antigen (e.g., PKKKRKV; SEQ ID NO: 7) or from other classical NLSs. In some embodiments, the nuclear localization signals described herein may comprise or be derived from non-classical NLS (e.g., acidic M9 domain in the hnRNP A1 protein; the sequence KIPIK in yeast transcription repressor Matα2; PY-NLS; ribosomal NLS; or the complex signals of U snRNPs). In some embodiments, the nuclear localization signal described herein comprises or consists essentially of the amino acid sequence of any one of SEQ ID NOs: 1 or 7-20, or any portion thereof. In some embodiments, the nuclear localization signal described herein comprises or consists essentially of a nuclear localisation signal which is SV40 NLS (e.g., comprised in SEQ ID NO: 1 or 7), GWG-SV40NLS (e.g., comprised in SEQ ID NO: 8), hnRNPA1 M9 NLS (e.g., comprised in SEQ ID NO: 9), hnRNP D NLS (e.g., comprised in SEQ ID NO: 10), hnRNP M NLS (e.g., comprised in SEQ ID NO: 11), PQBP-1 NLS (e.g., comprised in SEQ ID NO: 12), NLS2-RG Domain RPS17 (e.g., comprised in SEQ ID NO: 13), NLS1 RPS17 (e.g., comprised in SEQ ID NO: 14), NLS2 RPS17 (e.g., comprised in SEQ ID NO: 15), NLS3 RPS17 (e.g., comprised in SEQ ID NO: 16), cMyc NLS (e.g., comprised in SEQ ID NO: 17), HuR NLS (e.g., comprised in SEQ ID NO: 18), Tus NLS (e.g., comprised in SEQ ID NO: 19), or Nucleoplasmin NLS (e.g., comprised in SEQ ID NO: 20). In some instances, the SEQ ID NOs referred to above comprise an N-terminal cysteine residue that was used to facilitate conjugation to the polypeptide antigen (e.g., the thiol group of the N-terminal cysteine residue). Thus, in some embodiments, the NLS sequences referred to herein may exclude the N-terminal cysteine residue comprised in any one of SEQ ID NOs: 1 and 7-20. In some embodiments, other functional groups added or inserted (e.g., towards the N to C terminal portions of the peptides described herein) to facilitate steroid acid-peptide conjugation to a given polypeptide antigen are also envisaged (e.g., carboxyl groups, synthetic amino acids, etc.).

In some embodiments, the nuclear localization signals described herein may comprise the general consensus sequence: (i) K(K/R)X(K/R); (ii) (K/R)(K/R)$X_{10-12}$(K/R)$_{3/5}$, wherein (K/R)$_{3/5}$ represents three lysine or arginine residues out of five consecutive amino acids; (iii) KRX$_{10-12}$KRRK; (iv) KRX$_{10-12}$K(K/R)(K/R); or (v) KRX$_{10-12}$K(K/R)X(K/R), wherein X is any amino acid (Sun et al., 2016).

In some embodiments, modified polypeptide antigens described herein may exhibit increased cytosolic delivery, as compared to a corresponding unmodified polypeptide antigen. In some embodiments, modified polypeptide antigens described herein may exhibit increased total cellular delivery of the modified polypeptide antigen, as compared to a corresponding unmodified polypeptide antigen. In some embodiments, modified polypeptide antigens described herein may exhibit enhanced cellular immunity against the polypeptide antigen, as compared to a corresponding unmodified polypeptide antigen. In some embodiments, modified polypeptide antigens described herein exhibit increased IFN-gamma production by CD8+ T cells upon exposure to said polypeptide antigen, as compared to a corresponding unmodified polypeptide antigen. In some embodiments, modified polypeptide antigens described herein exhibit enhanced humoral immunity against said polypeptide antigen, as compared to a corresponding unmodified polypeptide antigen. In some embodiments, modified polypeptide antigens described herein trigger an increased variety (or biodiversity) of antibody species against the polypeptide antigen, as compared to a corresponding unmodified polypeptide antigen (e.g., including antibodies against epitopes that are poorly immunogenic).

In some aspects, described herein is a population of cells (e.g., in vitro or ex vivo) comprising or treated with the modified polypeptide antigens described herein. In some embodiments, the population of cells described herein may comprise immune cells (e.g., T cells), antigen-presenting cells (e.g., dendritic cells, macrophages, engineered antigen-presenting cells), MHC class I-expressing cells, MHC class II-expressing cells, or any combination thereof.

In some aspects, described herein is an immunogenic composition comprising: a modified polypeptide antigen described herein or produced by a method as described herein, or a population of cells as described herein, or any combination thereof; and a pharmaceutically acceptable excipient and/or adjuvant (e.g., vaccine adjuvant suitable for human or animal use). In some embodiments, the adjuvant may be an emulsion adjuvant, such as an oil-in-water emulsion adjuvant (e.g., a squalene-based oil-in-water emulsion adjuvant). In some embodiments, the immunogenic composition described herein may be a therapeutic or prophylactic vaccine (e.g., anti-cancer vaccine, anti-viral vaccine, or anti-bacterial vaccine). In some embodiments, modified polypeptide antigens described herein may enable a decrease in the quantity of antigen and/or antigen-presenting cells formulated in an immunogenic composition (e.g., vaccine) required to generate an immune response, as compared to the quantity when a corresponding unmodified polypeptide antigen lacking steroid-acid conjugation is used.

In some aspects, described herein is a method for triggering an enhanced adaptive immune response in a subject against a polypeptide antigen of interest, the method comprising administering an immunogenic composition as described herein to the subject.

In a further aspect, described herein is a method for treating or preventing a disease or disorder amenable to treatment by vaccination and/or immunotherapy, the method comprising administering an immunogenic composition as described herein to the subject.

In some aspects, described herein is a method for treating cancer in a subject, the method comprising administering an immunogenic composition as described herein to a subject in need thereof. In some embodiments, the method may be combined with immune-checkpoint inhibitor therapy or other anti-cancer treatment.

In some aspects, described herein is a modified polypeptide antigen as defined herein for use in generating an immune response in a subject. In some aspects, described herein is a modified polypeptide antigen as defined herein for use in the manufacture of an immunogenic composition (e.g., vaccine or immunotherapy) for generating an immune response in a subject. In some aspects, described herein is the use of the modified polypeptide antigen as defined herein, the modified polypeptide antigen produced by a method described herein, a population of cells as described herein, or the immunogenic composition as described herein, for generating an immune response in a subject. In some aspects, described herein is the use of the modified polypeptide antigen as defined herein, the modified polypeptide antigen produced by a method described herein, a population of cells as described herein, or the immunogenic composition as described herein, for the manufacture of a medicament (e.g., vaccine or immunotherapy) for generating an immune response in a subject. In some embodiments, the immune response may comprise enhanced cellular immunity against the polypeptide antigen, increased IFN-gamma production by CD8+ T cells upon exposure to the polypeptide antigen, enhanced humoral immunity against the polypeptide antigen, or any combination thereof, as compared to that generated from a corresponding unmodified polypeptide antigen.

In some aspects, described herein is a method for preparing a polypeptide antigen, the method comprising conjugating an unmodified polypeptide antigen to a sufficient number of steroid acid moieties to produce a modified polypeptide antigen that exhibits greater stability (e.g., thermal stability) than that of the polypeptide antigen prior to conjugation. In some embodiments, the number of steroid acid moieties conjugated to the polypeptide antigen is sufficient to increase endosomal escape of the modified polypeptide antigen upon intracellular delivery relative to a polypeptide antigen lacking said modification. In embodiments, the modified polypeptide antigen is a modified polypeptide antigen as defined herein.

Items

In various aspects, described herein are one or more of the following items:

1. A method of improving polypeptide antigen immunogenicity, the method comprising providing a polypeptide antigen to be modified, and covalently conjugating the polypeptide antigen to one or more steroid acid moieties to produce a modified polypeptide antigen, the modified polypeptide antigen being conjugated to a sufficient number of steroid acid moieties to increase endosomal escape of the modified polypeptide antigen upon intracellular delivery relative to a polypeptide antigen lacking said modification, wherein the modified polypeptide antigen triggers an improved adaptive immune response to said polypeptide antigen upon administration to a subject as compared to a corresponding unmodified polypeptide antigen.
2. The method of item 1, wherein the modified polypeptide antigen is conjugated to a sufficient number of steroid acid moieties such that the modified polypeptide antigen exhibits greater stability (e.g., thermal stability) than that of the polypeptide antigen prior to conjugation.
3. The method of item 1 or 2, wherein the polypeptide antigen is a protein antigen, and/or has a molecular weight of at least 10, 15, 20, 25, 30, 35, 40, 45, 50, 55, 60, 65, 70, 75, 80, 85, 90, 95, 100, 105, 110, 115, 120, 125, 130, 135, 140, 145, or 150 kDa.
4. The method of any one of items 1 to 3, wherein the polypeptide antigen comprises one or more MHC class I epitopes and/or MHC class II epitopes.
5. The method of any one of items 1 to 4, wherein the polypeptide antigen is or comprises a tumor-associated antigen (TAA), tumor-specific antigen (TSA), a neoantigen, a viral antigen, a bacterial antigen, a fungal antigen, an antigen associated with a disease or disorder amenable to treatment by vaccination and/or immunotherapy; or any antigenic fragment thereof.
6. The method of any one of items 1 to 5, wherein the polypeptide antigen is or comprises a corona viral antigen (e.g., SARS-CoV-2 Spike protein (SEQ ID NO: 3) or SARS-CoV Spike protein (SEQ ID NO: 4) or an antigenic fragment thereof; or a cancer antigen, such as a single-nucleotide variant antigen, a mutational frameshift antigen, splice variant antigen, a gene fusion antigen, an endogenous retroelement antigen, or another class of antigen, such as a human leukocyte antigen (HLA)-somatic mutation-derived antigen or a post-translational TSA, a viral-derived cancer antigen (e.g., from human papillomavirus (HPV), cytomegalovirus, or Epstein-Barr virus (EBV)), a cancer-testis antigen, HER2, PSA, TRP-1, TRP-2, EpCAM, GPC3, CEA, MUC1, MAGE-A1, NY-ESO-1, SSX-2, mesothelin (MSLN), EGFR, cell lysates or other material derived from a tumor (e.g., tumor-derived exosomes).

7. The method of any one of items 1 to 6, wherein the steroid acid triggers ceramide accumulation on the inner leaflet of endosomes, thereby destabilizing endosomal membranes and facilitating endosomal escape of the polypeptide antigen upon intracellular delivery.

8. The method of any one of items 1 to 7, wherein the steroid acid triggers increased acid sphingomyelinase (ASM)-mediated cleavage of sphingomyelin to form ceramide.

9. The method of any one of items 1 to 8, wherein the steroid acid is a bile acid.

10. The method of any one of items 1 to 9, wherein the steroid acid is a primary bile acid or a secondary bile acid.

11. The method of any one of items 1 to 10, wherein the steroid acid is or comprises: (a) a bile acid which is: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycodeoxycholic acid (CDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GCDCA); (b) an analog of the bile acid of (a) that: induces endocytosis; triggers ceramide accumulation on the inner leaflet of endosomes; triggers increased acid sphingomyelinase (ASM)-mediated cleavage of sphingomyelin to form ceramide; and/or has a hydrophobicity greater than that of cholic acid; (c) a bile acid or bile acid analog that is more hydrophobic than cholic acid (e.g. CDCA, DCA, LCA, TCA, TDCA, TCDCA, GCA, GDCA, or GCDCA); or (d) any combination of (a) to (c).

12. The method of any one of items 1 to 11, wherein each modified polypeptide antigen molecule is conjugated to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 steroid acid moieties.

13. The method of any one of items 1 to 12, wherein the modified polypeptide antigen molecule is conjugated to the steroid acid at solvent-accessible amine (e.g., primary amine) and/or sulfhydryl groups of the polypeptide antigen.

14. The method of any one of items 1 to 13, wherein the modified polypeptide antigen molecule is conjugated to the steroid acid via a linker (e.g., bifunctional, trifunctional linker, or multi-functional linker).

15. The method of any one of items 1 to 14, wherein the steroid acid is comprised in a steroid acid-peptide conjugate and the polypeptide antigen is conjugated to the steroid acid-peptide conjugate (e.g., via said peptide, such as at an N- or C-terminal residue).

16. The method of item 15, wherein the peptide: (i) comprises a protein transduction domain that stimulates endocytosis and/or endosomal formation; (ii) comprises a subcellular targeting signal; (iii) is a cationic peptide (e.g., a non-cell-penetrating cationic peptide); (iv) is a non-immunogenic peptide; or (v) any combination of (i) to (iv).

17. The method of item 16, wherein the subcellular targeting signal is a nuclear localization signal, such as a classical NLS (e.g., NLS from SV-40 large T-antigen (e.g., PKKKRKV; SEQ ID NO: 7) or from other classical NLSs) or a non-classical NLS (e.g., acidic M9 domain in the hnRNP A1 protein; the sequence KIPIK in yeast transcription repressor Matα2; PY-NLS; ribosomal NLS; and the complex signals of U snRNPs).

18. The method of item 16 or 17, wherein the nuclear localization signal is a/an: SV40 NLS (e.g., comprised in SEQ ID NO: 1 or 7), GWG-SV40NLS (e.g., comprised in SEQ ID NO: 8), hnRNPA1 M9 NLS (e.g., comprised in SEQ ID NO: 9), hnRNP D NLS (e.g., comprised in SEQ ID NO: 10), hnRNP M NLS (e.g., comprised in SEQ ID NO: 11), PQBP-1 NLS (e.g., comprised in SEQ ID NO: 12), NLS2-RG Domain RPS17 (e.g., comprised in SEQ ID NO: 13), NLS1 RPS17 (e.g., comprised in SEQ ID NO: 14), NLS2 RPS17 (e.g., comprised in SEQ ID NO: 15), NLS3 RPS17 (e.g., comprised in SEQ ID NO: 16), cMyc NLS (e.g., comprised in SEQ ID NO: 17), HuR NLS (e.g., comprised in SEQ ID NO: 18), Tus NLS (e.g., comprised in SEQ ID NO: 19), or Nucleoplasmin NLS (e.g., comprised in SEQ ID NO: 20) or is a variant of an NLS having nuclear localization activity, the NLS comprising or consisting of the amino acid sequence of any one of SEQ ID NOs: 7 to 20.

19. The method of any one of items 1 to 18, wherein the modified polypeptide antigen triggers: (i) increased cytosolic delivery of the modified polypeptide antigen, as compared to a corresponding unmodified polypeptide antigen; (ii) increased total cellular delivery of the modified polypeptide antigen, as compared to a corresponding unmodified polypeptide antigen; (iii) enhanced cellular immunity against said polypeptide antigen, as compared to a corresponding unmodified polypeptide antigen; (iv) increased IFN-gamma production by CD8+ T cells upon exposure to said polypeptide antigen, as compared to a corresponding unmodified polypeptide antigen; (v) enhanced humoral immunity against said polypeptide antigen, as compared to a corresponding unmodified polypeptide antigen; (vi) an increased variety of antibody species against the polypeptide antigen, as compared to a corresponding unmodified polypeptide antigen; or (vii) any combination of (i) to (vi).

20. A population of cells (e.g., in vitro or ex vivo) comprising the modified polypeptide antigen produced by the method of any one of items 1 to 19, or the modified polypeptide antigen as defined in any one of items 1 to 19.

21. The population of cells of item 20, which comprises immune cells (e.g., T cells), antigen-presenting cells (e.g., dendritic cells, macrophages, engineered antigen-presenting cells), MHC class I-expressing cells, MHC class II-expressing cells, or any combination thereof.

22. An immunogenic composition comprising: the modified polypeptide antigen produced by the method of any one of items 1 to 19, the modified polypeptide antigen as defined in any one of items 1 to 19, the population of cells of item 20 or 21, or any combination thereof; and a pharmaceutically acceptable excipient and/or adjuvant (e.g., an emulsion adjuvant, oil-in-water emulsion adjuvant, or a squalene-based oil-in-water emulsion adjuvant).
23. The immunogenic composition of item 22, which is a therapeutic or prophylactic vaccine (e.g., anti-cancer vaccine, anti-viral vaccine, or anti-bacterial vaccine).
24. A method for triggering an enhanced adaptive immune response in a subject against an unmodified polypeptide antigen of interest, the method comprising administering the immunogenic composition of item 22 or 23 to the subject.
25 A method for vaccinating a subject against an infectious disease, the method comprising administering the immunogenic composition of item 22 or 23 to the subject, wherein the polypeptide antigen comprises an antigenic fragment of a pathogen (e.g., virus, bacteria, fungus) causing the infectious disease.
26. A method for treating cancer in a subject, the method comprising administering the immunogenic composition of item 22 or 23 to the subject.
27. The method of item 26, wherein the method is combined with immune-checkpoint inhibitor therapy.
28. A modified polypeptide antigen as defined in any one of items 1 to 19, or produced by the method of any one of items 1 to 19, for use in generating an immune response in a subject or for the manufacture of an immunogenic composition for generating an immune response in a subject.
29. Use of the modified polypeptide antigen as defined in any one of items 1 to 19, the modified polypeptide antigen produced by the method of any one of items 1 to 19, the population of cells as defined in item 20 or 21, or the immunogenic composition as defined in item 22 or 23, for generating an immune response in a subject or for the manufacture of a medicament (e.g., vaccine) for generating an immune response in a subject.
30. The modified polypeptide antigen for the use of item 28, or the use of item 29, wherein the immune response comprises enhanced cellular immunity against said polypeptide antigen, increased IFN-gamma production by CD8+ T cells upon exposure to said polypeptide antigen, enhanced Immoral immunity against said polypeptide antigen, or any combination thereof, as compared to that generated from a corresponding unmodified polypeptide antigen.
31. A method for preparing a polypeptide antigen, the method comprising conjugating an unmodified polypeptide antigen to a sufficient number of steroid acid moieties to produce a modified polypeptide antigen that exhibits greater stability (e.g., thermal stability) than that of the polypeptide antigen prior to conjugation.
32. The method of item 31, wherein the number of steroid acid moieties conjugated to the polypeptide antigen is sufficient to increase endosomal escape of the modified polypeptide antigen upon intracellular delivery relative to a polypeptide antigen lacking said modification.
33. The method of item 31 or 32, wherein the modified polypeptide antigen is as defined in any one of items 3 to 19.
34. A method of improving polypeptide antigen immunogenicity, the method comprising providing a polypeptide antigen to be modified, and covalently conjugating the polypeptide antigen to one or more bile acid-peptide moieties to produce a modified polypeptide antigen, the modified polypeptide antigen being conjugated to a sufficient number of bile acid-peptide moieties to trigger an improved adaptive immune response to said polypeptide antigen upon administration to a subject as compared to a corresponding unmodified polypeptide antigen, wherein the peptide comprised in the bile acid-peptide moiety comprises a nuclear localization signal (NLS).
35. The method of item 34, wherein the modified polypeptide antigen is conjugated to a sufficient number of bile acid-peptide moieties to increase antigen presentation of the modified polypeptide antigen upon intracellular delivery relative to a corresponding unmodified polypeptide antigen.
36. The method of item 34 or 35, wherein the modified polypeptide antigen is conjugated to a sufficient number of bile acid-peptide moieties such that the modified polypeptide antigen exhibits greater thermal stability relative to a corresponding unmodified polypeptide antigen.
37. The method of any one of items 34 to 36, wherein covalently conjugating the polypeptide antigen to one or more bile acid-peptide moieties is performed by reacting the polypeptide antigen with a molar excess of the bile acid-peptide moiety.
38. The method of item 37, wherein the polypeptide antigen is reacted with between a 2-fold and 100-fold molar excess of the bile acid-peptide moiety.
39. The method of item 37, wherein the polypeptide antigen is reacted with between a 2-fold and 50-fold molar excess of the bile acid-peptide moiety.
40. The method of item 37, wherein the polypeptide antigen is reacted with between a 5-fold and 25-fold molar excess of the bile acid-peptide moiety.
41. The method of any one of items 34 to 40, wherein the mean number of bile acid-peptide moieties conjugated per modified polypeptide antigen is at least 1 about, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50; or is between about 1, 2, 3, 4, 5, 6, 7, 8, 9, or 10 and n, wherein n is the total number of accessible sites on the polypeptide antigen available for conjugation.
42. The method of any one of items 34 to 41, wherein the bile acid is: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycodeoxycholic acid (CDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GUDCA).
43. The method of any one of items 34 to 42, wherein the bile acid is an analog of CA, CDCA, DCA, LCA, GDCA, GCA, TCA, CDCA, GCDCA, TDCA, GLCA, TLCA, THDCA, TCDCA, UCA, TUDCA, UDCA, or GUDCA, wherein the analog: induces endocytosis; triggers ceramide accumulation on the inner leaflet of endosomes; or triggers increased acid sphingomyelinase (ASM)-mediated cleavage of sphingomyelin to form ceramide.
44. The method of any one of items 34 to 43, wherein the nuclear localization signal is a/an: SV40 NLS (SEQ ID NO: 1 or 7), GWG-SV40NLS (SEQ ID NO: 8), hnRNPA1 M9 NLS (SEQ ID NO: 9), hnRNP D NLS (SEQ ID NO: 10), hnRNP M NLS (SEQ ID NO: 11), PQBP-1 NLS (SEQ ID NO: 12), NLS2-RG Domain RPS17 (SEQ ID NO: 13), NLS1 RPS17 (SEQ ID NO: 14), NLS2 RPS17 (SEQ ID NO: 15), NLS3 RPS17 (SEQ ID NO: 16). cMyc NLS (SEQ ID NO: 17), HuR NLS (SEQ ID NO: 18). Tus NLS (SEQ ID NO: 19), or Nucleoplasmin NLS (SEQ ID NO: 20).

45. The method of any one of items 34 to 44, wherein the nuclear localization signal is a variant of an NLS having nuclear localization activity, the NLS comprising or consisting of the amino acid sequence of any one of SEQ ID NOs: 7 to 20.
46. The method of any one of item 34 to 45, wherein the polypeptide antigen is conjugated to the one or more bile acid-peptide moieties via a linker.
47. The method of item 46, wherein the linker is a bifunctional linker, trifunctional linker, or multi-functional linker.
48. The method of any one of items 34 to 47, wherein the modified polypeptide antigen molecule is conjugated to the one or more bile acid-peptide moieties via a solvent-accessible functional group of the polypeptide antigen.
49. The method of any one of item 34 to 48, wherein the polypeptide antigen is or comprises a tumor-associated antigen (TAA), tumor-specific antigen (TSA), cell lysate derived from a tumor, tumor-derived exosomes, a neoantigen, a viral antigen, a bacterial antigen, a fungal antigen, or other antigen associated with a disease or disorder amenable to treatment by vaccination and/or immunotherapy.
50. The method of any one of items 34 to 49, wherein the polypeptide antigen is or comprises a SARS-CoV Spike protein or an antigenic fragment thereof.
51. An immunogenic composition comprising: the modified polypeptide antigen produced by the method of any one of items 34 to 50 or a population of cells comprising the modified polypeptide antigen produced by the method of any one of items 34 to 50, and a pharmaceutically acceptable excipient and/or adjuvant.
52. The immunogenic composition of item 51, wherein the population of cells comprises dendritic cells, B cells, T cells, macrophages, engineered antigen-presenting cells, MHC class 1-expressing cells, MHC class II-expressing cells, or any combination thereof.
53. A method for triggering an enhanced adaptive immune response in a subject against an unmodified polypeptide antigen of interest, the method comprising administering the immunogenic composition of item 52 to the subject.

EXAMPLES

Example 1: General Materials and Methods

Animals and Ethics

Six to eight week-old BALB/c mice were purchased from Jackson Laboratories (Bar Harbor, ME, USA) whereas C57BL/6 mice of similar age were purchased from Charles River (Montreal, QC, Canada). Littermate mice were interbred and housed in a pathogen-free environment at the animal facility of the Institute for Research in Immunology and Cancer (IRIC). Animal protocols were approved by the Animal Care Committee of Université de Montréal.

Cell Lines and Reagents

All cell culture media and reagents were purchased from Wisent Bioproducts (St-Bruno, QC, Canada) unless otherwise indicated. All flow cytometry antibodies were purchased from BD Biosciences (San Jose, CA, USA) unless otherwise indicated. The albumin from chicken egg white (ovalbumin; OVA), the LPS and the Nunc MaxiSorp™ plates were purchased from Sigma-Aldrich (St-Louis, MI, USA). OVA-DQ™ was purchased from ThermoFisher (Waltham, MA, USA). The SIINFEKL peptide was synthesized by Genscript (Piscataway, NJ, USA). The Bradford reagent was purchased from Bio-Rad (Hercules, CA, USA). All cytokine ELISAs were purchased from R&D Systems (Minneapolis, MN, USA) unless otherwise indicated. Recombinant GM-CSF was purchased from Peprotech (Rocky Hill, NJ, USA). The CD8 and CD4 T-cell isolation kits were purchased from StemCell Technologies (Vancouver, BC, Canada). The PD-1 antibody (clone RMP1-14) used in in vivo studies was purchased from BioXCell (West Lebanon, NH, USA).

Generation of Bone Marrow Derived DCs

Mouse bone marrow derived DCs (BMDCs) were generated by flushing the whole marrow from mouse femurs using RPMI™ 1640 supplemented with 10% fetal bovine serum (FBS), 50 U/mL Penicillin-Streptomycin, 2 mM L-glutamine, 10 mM HEPES, 1% MEM Non-essential Amino Acids, 1 mM Sodium Pyruvate, 0.5 mM β-mercaptoethanol. Following red blood cell lysis, cells were then cultured in media supplemented with 50 ng/mL murine recombinant GM-CSF. The media was changed on days 2, 4, 6 and 8. On day 9, the media was replaced to include recombinant murine GM-CSF and LPS from *Escherichia coli* O111 (1 ng/mL) to stimulate DC maturation. Mature DCs were assessed by flow cytometry for their surface expression of CD3, CD19, NK1.1, CD11c, CD80, CD86, and I-A$^b$.

Modeling Accessible Lysine in Protein Antigen

Antigen 3D structure was modeled using the RCSB PDB and Swiss-Model Expasy™ free access software. Accessible amino acids representing the lysine residues were identified and highlighted according to their rate of accessibility (high; medium and poor).

Cancer Cell Lysate Preparation

To prepare cancer cell lysates, cultured EL4 cells were collected by centrifugation at 1500 rpm for 5 min followed by two washing steps with PBS to remove traces of FBS. The cells were then subjected to 5 rounds of freeze and thaw in liquid nitrogen/boiling water, respectively. To remove large particles, the lysate was shredded using a G26 needle, passed through a 70 µm cell strainer, then filtered through a 0.45 µm filter. The obtained lysate was then quantified using Bradford reagent, aliquoted and stored at −80° C. until use.

Generation of the ChAcNLS-Antigen Formulations

ChAcNLS was synthesized as previously described in Beaudoin et al., 2016 unless otherwise indicated. OVA, OVA-DQ, or cancer cell lysate were solubilized at 1-10 mg/mL in sterile PBS with or without other formulation components, but free of amine (NH$_3$) or sulfhydryl (SH) groups. The SM(PEG)$_4$ cross-linker was added to the reaction for 1 h using different molar excess ratios (5×, 10×, 25×, 50×). The free SM(PEG)$_4$ cross-linker was discarded by Centricon™ filtration and Sephadex™ column. ChAcNLS was added in the same molar excess ratios and incubated for 1 h to obtain different amounts of ChAcNLS moieties linked per antigen. Unless otherwise specified, the cOVA conjugates tested in the Examples were produced using 50× molar excess ratios. Free unlinked ChAcNLS was removed by centricon filtration and Sephadex column. ChAcNLS-modified antigens were concentrated in sterile PBS to obtain final concentration 5-10 mg/mL as determined by UV absorbance.

To evaluate ChAcNLS loading, 10 µg of OVA or ChAcNLS-OVA conjugates were separated under reducing conditions on a 12% polyacrylamide gel and stained with Coomassie brilliant blue R-250™ (Bio-Rad, Mississauga, ON, Canada). The migration distance in the gel relative to the blue dye front (Rf) was measured and the numbers of ChAcNLS moieties introduced into OVA were categorized into low, medium, and high ChAcNLS loads, estimated by reference to a logarithm plot of molecular weight versus 1/Rf for Kaleidoscope pre-stained standards (Bio-Rad) electrophoresed under identical conditions. In addition, western blot analysis against OVA was performed to confirm the Coomassie results.

Biochemical Characterization of ChAcNLS-OVA

A series of tests including: 1) Differential Scanning Calorimetry or Dynamic Light Scattering, 2) Circular Dichroism (CD) Far and Near UV Spectra Scans and Fourier Transform Infrared Spectroscopy (FTIR), 3) Size Exclusion Chromatography with Multi Angle Laser Light Scattering, 4) Intrinsic Tryptophan Fluorescence (ITF), 5) Peptide Mapping (Reference Standard Characterization by LC-MS/MS), and 6) Intact and Subunit Molecular Weight via LC-MS were conducted by Charles River (Wilmington, MA, USA) to characterize the ChAcNLS-OVA modified antigens.

Generation of the Bile Acid-NLS Moieties

Bile acid-NLS moieties were synthesized similar to the synthesis of cholic acid-NLS (ChAcNLS) as previously described in Beaudoin et al., 2016 unless otherwise specified. For example, for CA-SV40NLS, cholic acid was conjugated to the free amino group of the N-terminal cysteine residue of a 13-mer peptide (CGYGPKKKRKVGG; SEQ ID NO: 1) that comprises a nuclear localization signal from SV40 large T-antigen (SEQ ID NO: 7) flanked by linker amino acids.

Assessment of Intrinsic Tryptophan Fluorescence (ITF)

An Applied Photophysics (Leatherhead, Surrey, UK) Chirascan™ Q100 circular dichroism (CD) spectrometer was used for intrinsic tryptophan fluorescence (ITF) analysis and a VWR digital heatblock (Radnor, PA) was used for dry block temperature incubations. The Chirscan Q100 autosampler rack cooling system was used for all 4° C. incubations. Data was analyzed using MATLAB software (Natick, MA). Briefly, samples were removed from storage at −20° C. and allowed to equilibrate to room temperature. Samples were then diluted to 0.8 mg/mL in PBS from stock concentrations in the range of 4 to 5 mg/mL. Diluted samples were then analyzed for ITF without exposure to thermal stress (Native) or after ten minutes of thermal stress by dry block incubation. An aliquot of each diluted sample was incubated at 4° C., a second aliquot was incubated at 37° C., while a third aliquot was incubated at 80° C. BSA, diluted to 0.8 mg/mL, was included with the samples under each of the thermal conditions described above. All samples were re-equilibrated to room temperature after incubation. ITF Analysis was performed in 8 triplicates by excitation at 280 nm with an emission scan range of 200-600 nm with a bandwidth of 1.0 nm, a Time-per point of 1 s, and a Step of 0.5. The triplicate spectra were blank subtracted, averaged, and converted from units of mdeg to relative fluorescence intensity using MATLAB software. Diluted BSA solutions were assayed as controls preceding and following the sample sequence.

DC2.4 Transfection and Assessment of Damaged Endosomes by Microscopy

For this assay, 15×10$^3$ DC2.4 cells were seeded on a sterile cover slide in a 24-well plate. Two days following transfection of DC2.4 cells with the eGFP-hGal3 mammalian expression vector, 0.1 mg/mL of nOVA or cOVA was added to cells then incubated for 3 h at 37° C. The cells were then washed twice to remove excess protein prior to being mounted on a slide. The slides were viewed by fluorescent microscopy (Nikon, Eclipse™ Ti2-U) and the results analyzed using the ImageJ™ software.

Phenotypic Assessment of Generated BMDCs by Flow Cytometry

To assess the expression of cell surface markers, BMDCs were incubated with various antibodies diluted according to manufacturer's instructions using the staining buffer (PBS containing 2% FBS) for 30 min at 4° C. in the dark. After extensive washing using the staining buffer, the cells were re-suspended in 400 µL of staining buffer. The samples were acquired by BD FACSDiva™ on CANTOII™, then analyzed using FlowJo™ v10.

Monitoring Antigen Processing

To evaluate OVA processing, cells were incubated with 10 µg/mL OVA-DQ (with or without ChAcNLS modification) at 37° C. 30 minutes later, cells were washed, and regular media was added. At the end of the indicated incubation time, cells were collected and washed with cold PBS containing 2% FBS. Fluorescence was monitored by analyzing the cells by flow cytometry.

Antigen Presentation Assay

To evaluate antigen cross-presentation, cells were seeded at 25×10$^3$ cells per well in 24-well plate (Corning; Mass., United States), then pulsed with the antigens at different concentrations for 3 h. At the end of the pulsing period, the cells were washed to remove excess antigen and co-cultured with 10$^6$/mL CD4 or CD8 T-cells purified from the spleen of OT-II or OT-I mouse, respectively, using T-cell isolation kits according to the manufacturer's protocol. After 72 hours, supernatants were collected and used to quantify cytokine production by commercial enzyme-linked immunosorbent assays (ELISAs).

For the B3Z assay, 5×10$^4$ DCs were first pulsed with the selected proteins or cOVA variants for 3 h followed by washing prior to adding 5×10$^4$ B3Z cells. The cells were incubated for 17-19 h prior to their lysis and incubation for another 4-6 h at 37° C. with a Chlorophenol red-β-D-galactopyranoside (CPRG) solution. The optical density signal was detected using a SynergyH1™ microplate reader (Biotek, Winooski, VT, United States).

Quantification of Antibody Titer by ELISA

Nunc MaxiSorp™ plates were coated overnight with 1 µg OVA diluted in coating buffer at 4° C. The following day, the plates were washed then blocked with 3% skim milk for 1 h at room temperature. Following that step, the plates were washed prior to adding the diluted sera (two-fold dilutions were prepared). Following a 2-h incubation period, the plates were washed prior to adding the secondary HRP-linked anti-mouse IgG antibody at a dilution of 1:1000. Two hours later, the plates were washed then incubated at room temperature with HRP for 10-20 min. Following HRP quenching, the signal was detected using a Synergy™ H1 microplate reader (Biotek; Winooski, VT, United States).

Immunizations and Tumor Challenge

For prophylactic vaccinations, female C57BL/6 mice (n=10/group) were subcutaneously (SC)-injected at Day 0 and 14 with OVA/OVA-ChAcNLS (1 µg/dose), 10$^4$ BMDCs pulsed with the OVA formulations (0.1 mg/mL), or tumor lysate (0.1 mg/mL). Two weeks following the second vaccination, mice were subcutaneously (SC) challenged with 5×10$^5$ EG.7 or EL4 cells and tumor growth was assessed over time. To evaluate antigen-specific CD8 T-cell activation, splenocytes isolated from immunized mice were first stimulated in vitro with 1 µg/mL OVA then the supernatant collected three days later to assess cytokine/chemokine production by Luminex™.

For therapeutic vaccinations, female C57BL/6 mice (n=10/group) received a SC injection of $5\times10^5$ EL4 or EG.7 cells at Day 0. Five days later (appearance of palpable tumors~40-60 mm$^3$), mice were SC-injected with $3\times10^4$ OVA-/OVA-ChAcNLS or tumor lysate-/ChAcNLS-lysate-pulsed BMDCs (two injections; 1 week apart). Control animals received $5\times10^5$ tumor cells alone. Treated animals were followed thereafter for tumor growth. For therapeutic vaccination in combination with immune-checkpoint inhibitors (e.g., αPD-1), mice received SC-injections of the antibody or its isotype at 200 µg/per dose every 2 days for a total of 6 doses over two weeks. A similar approach was conducted for allogeneic dosing vaccination in BALB/c mice.

Analysis of Tumor-Infiltrating Immune Cells

Following their resection, tumor masses were first weighed then cut into smaller pieces_with surgical scissors in 4-5 ml of Master Mix containing 2 mg/ml of Collagenase D,_2 mg/mL of collagenase IV, and 100 µg/mL of DNase type IV mixed in DMEM_supplemented with 5% FBS. The mix was then stirred in a cell culture incubator at 37° C._After 30 min of incubation, 10 mL of DMEM was added to neutralize the enzymatic_reaction. The digested solution was filtered using a 70 µm cell strainer and all retained_ fragments at the top of the strainer were smashed with a plunger followed by addition of_1-2 DMEM to wash the strainer. Collected cells were then centrifuges for 5 min at 1200 rpm (4° C.), treated with a red blood cell lysis buffer for 1 min then resuspended in 3-4 mL of DMEM supplemented with 5% FBS. Following cell washing, the pellet was resuspended in DMEM supplemented with 5% FBS prior to initiate cell staining for flow cytometry analysis.

Antigen-Presentation Assay Using the B3Z Reporter System

Various bile acid-NLS conjugates were screened using the B3Z reporter system. The B3Z cell line is a T-cell hybridoma specific for the H2-Kb-SIINFEKL complex. Once activated via its TCR, the LacZ reporter gene (under the NFAT promoter control) is expressed. Briefly, $1.5\times10^5$ BMDCs or isolated B cells were co-cultured with $5\times10^4$ B3Z cells treated with ovalbumin (OVA)-bile acid-NLS conjugates for overnight at 37° C. with 5% $CO_2$. The following day, all cells were washed twice with PBS (pH 7.4), and the cell pellets were lysed by adding 100 µL of a lysis buffer containing 0.15 mM chlorophenol red-beta-D-galactopyranoside (CPRG) substrate (Calbiochem, La Jolla, CA), 0.125% NP40 (EMD Sciences, La Jolla, CA), 9 mM $MgCl_2$ (Aldrich, USA) and 100 mM 2-mercaptoethanol in PBS. After a 5- or 24-h incubation at 37° C., absorbance was taken at 570 nm with 636 nm as the reference wavelength. For these experiments, bile acid-NLS-OVA conjugates were re-suspended in PBS (pH 7.3) at 0.1 mg/mL (prepared with 10× molar ratio of bile acid-NLS moiety to OVA) and OVA alone was resuspended at 5 mg/mL.

Statistical Analysis p-values were calculated using the one-way analysis of variance (ANOVA). Results are represented as average mean with S.D. error bars, and statistical significance is represented with asterisks: $*P<0.05$, $P<0.01$, $*P<0.001$.

Example 2: Biochemical Characterization of the ChAcNLS-Antigen Formulation

The steroid acid-peptide conjugate, ChAcNLS, was synthesized as described in Example 1. Briefly, cholic acid was conjugated to the free amino group of the N-terminal cysteine residue of a 13-mer peptide. The peptide (CGYGPKKKKRKVGG; SEQ ID NO: 1) comprised a nuclear localization signal (underlined) from SV40 large T-antigen flanked by linker amino acids. Multiple ChAcNLS moieties were then conjugated to the epsilon-amino groups of accessible lysine residues of the prototypical polypeptide antigen OVA (SEQ ID NO: 2; FIG. 1C). A schematic diagram representing covalent binding of a given antigen to an ChAcNLS moiety is shown in FIG. 1A. ChAcNLS-OVA was then biochemically characterized, as described in Example 1, and binding was confirmed by Coomassie blue staining (FIG. 1B) and Western blot (FIG. 1E). Biochemical characterizations revealed that ChAcNLS-OVA conjugated at a ratio of 25× (FIG. 1B, line 2) had an average of about four ChAcNLS moieties conjugated per OVA corresponding to a MW increase of about 8.6 kDa. ChAcNLS-OVA conjugated at a ratio of 50× (FIG. 1B, line 3) had an average of about eight ChAcNLS moieties conjugated per OVA corresponding to a MW of about 19.2 kDa. A ribbon structure of the OVA protein with lysine residues that are predicted to be highly, moderate or poorly accessible lysine residues is shown in FIG. 1D.

Furthermore, to assess the overall stability of ChAcNLS-OVA (cOVA), ITF analysis was conducted to measure its unfolding following thermal stress. In this assay, changes in peak shifts or intensities are indicative of unfolding as polypeptide residues may become solvent-exposed and undergo change in orientation (FIG. 1F). When different cOVA ratios were assayed under native or thermally variable conditions, nOVA underwent complete denaturation at 80° C. along with partial reduction in peak intensity observed for the 50× cOVA (FIG. 1F). No changes in ITF spectral measures were observed for the other cOVA samples suggesting that conjugation with the ChAcNLS moieties greatly increased antigen stability.

An antigen presentation assay using the SIINFEKL-specific B3Z cell line was then conducted to compare different OVA conjugates. As shown schematically in FIG. 1G, the different conjugates tested included: cholic acid-NLS moiety ("ChAcNLS"); OVA conjugated to cholic acid moieties without an NLS peptide ("ChAc-OVA"); OVA conjugated to cholic acid-NLS moieties via a $PEG_4$ bifunctional linker ("ChAcNLS-$PEG_4$-OVA" or "cOVA"); and OVA conjugated to cholic acid-NLS moieties via a $PEG_6$ bifunctional linker ("ChAcNLS-$PEG_6$-OVA"). As shown in FIG. 1H, conjugating OVA to cholic acid moieties alone without an NLS peptide ("ChAc-OVA") did not lead to improved antigen presentation as compared to naked OVA ("nOVA") alone. Strikingly, OVA conjugated with 50× molar excess of ChAcNLS moieties via a $PEG_4$ bifunctional linker ("cOVA (50×)") exhibited the same level of antigen presentation as the SIINFEKL positive control peptide ("SIINFEKL"). Interestingly, comparable levels of antigen presentation were obtained by reducing the molar excess of ChAcNLS moieties to 5×, 10× and 25× ["cOVA (ChAcNLS-$PEG_4$-OVA)"], although this heightened antigen presentation was lost at a 2× molar excess of ChAcNLS moieties. Antigen presentation levels comparable to the SIINFEKL positive control were also observed for OVA conjugated with 2× to 25× molar excess of ChAcNLS moieties via a $PEG_6$ bifunctional linker ("ChAcNLS-$PEG_6$-OVA"). Lastly, antigen presentation levels higher than nOVA but below that of the SIINFEKL positive control peptide were observed using OVA conjugated with 5× and 10× molar excess of ChAcNLS moieties via a much longer $PEG_{24}$ bifunctional linker ("ChAcNLS-PEG$_{24}$-OVA"), but the increase in antigen presentation over the nOVA was lost at molar excesses of 2× and 25× (data not shown).

Example 3: In Vitro Cross Presentation of ChAcNLS-OVA

To generate BMDCs, femur and tibias of female C57BL/6 or BALB/c mice were flushed to collect total nucleated cells. Cells were then plated for 8 days with recombinant GM-CSF (10 ng/mL) and replaced every 2 days. LPS was added on day 9 to trigger DC maturation prior to antigen pulsing. Maturation of the BMDCs was confirmed by flow cytometry. No T cells, B cells or NK cells were detected at Day 9 and more than 80% of BMDCs expressed CD11c+, CD80+, CD86+, and I-Ab+. BMDCs were then incubated with either naked OVA (nOVA) or ChAcNLS-OVA (cOVA) at varying concentrations, and either CD4+ T cells from OT-II transgenic mice or CD8+ T cells from OT-I transgenic mice were added.

Figure 2A:
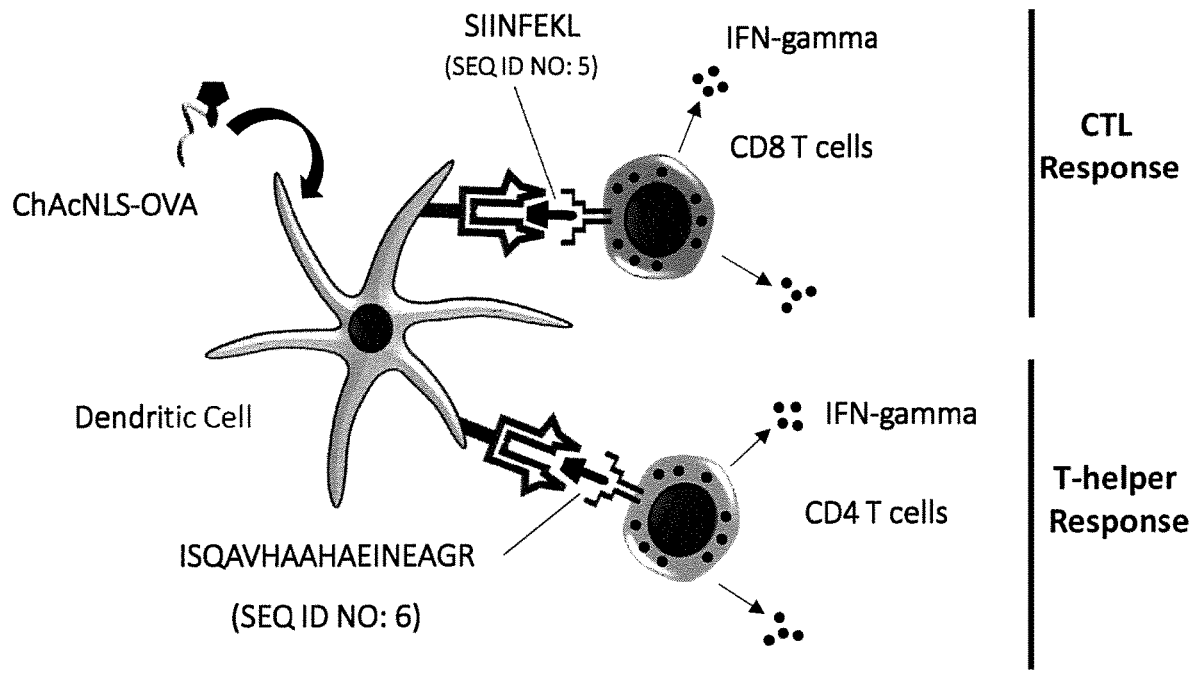
FIG. 2A-G shows the results of an antigen cross-presentation assay.

FIG. 2A is a schematic diagram showing the set-up of the antigen cross-presentation of OVA peptides (i.e., SIINFEKL [OT-I peptide for CD8+ T cell; SEQ ID NO: 5] or ISQAVHAAHAEINEAGR [OT-II peptide for CD4+ T cells; SEQ ID NO: 6]) used to assess OVA-responding OT-I (CD8) and OT-II (CD4) T cell activation.

Figure 2B:
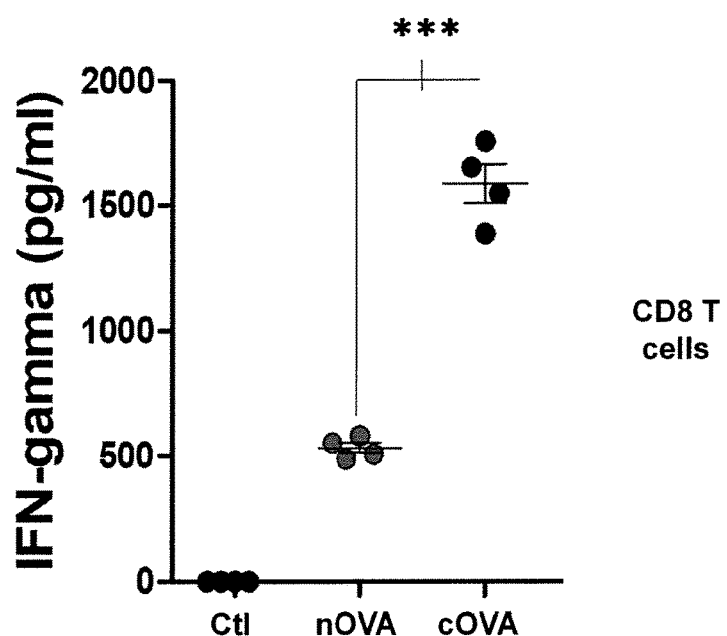
Figure 2C:
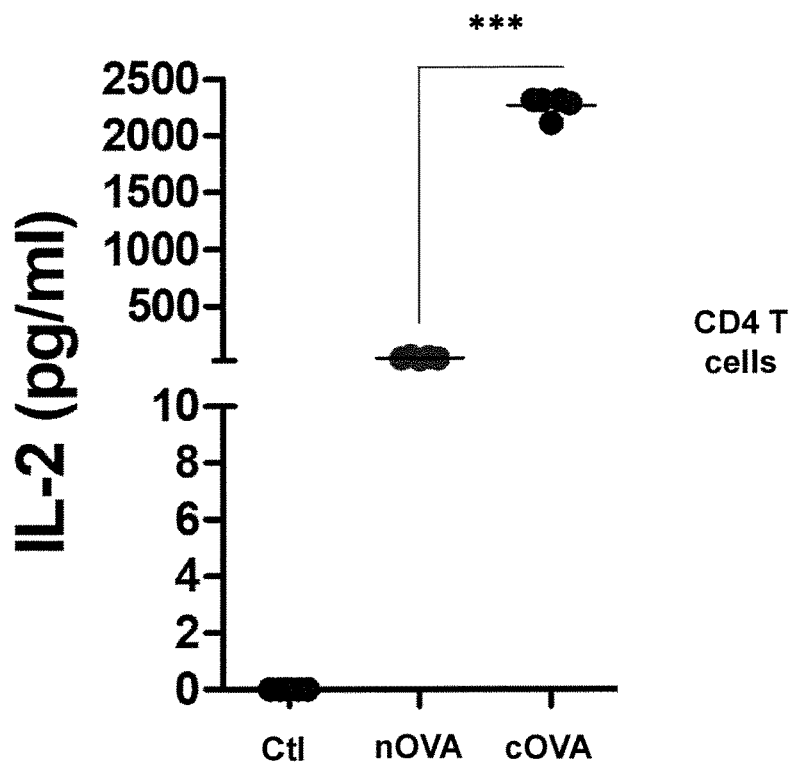
Figure 2D:
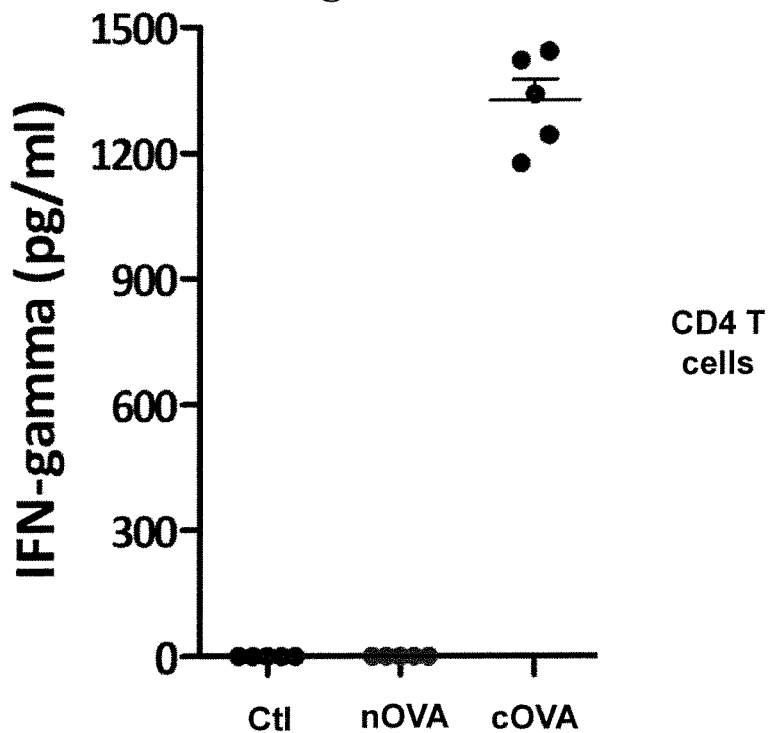
Figure 2E:
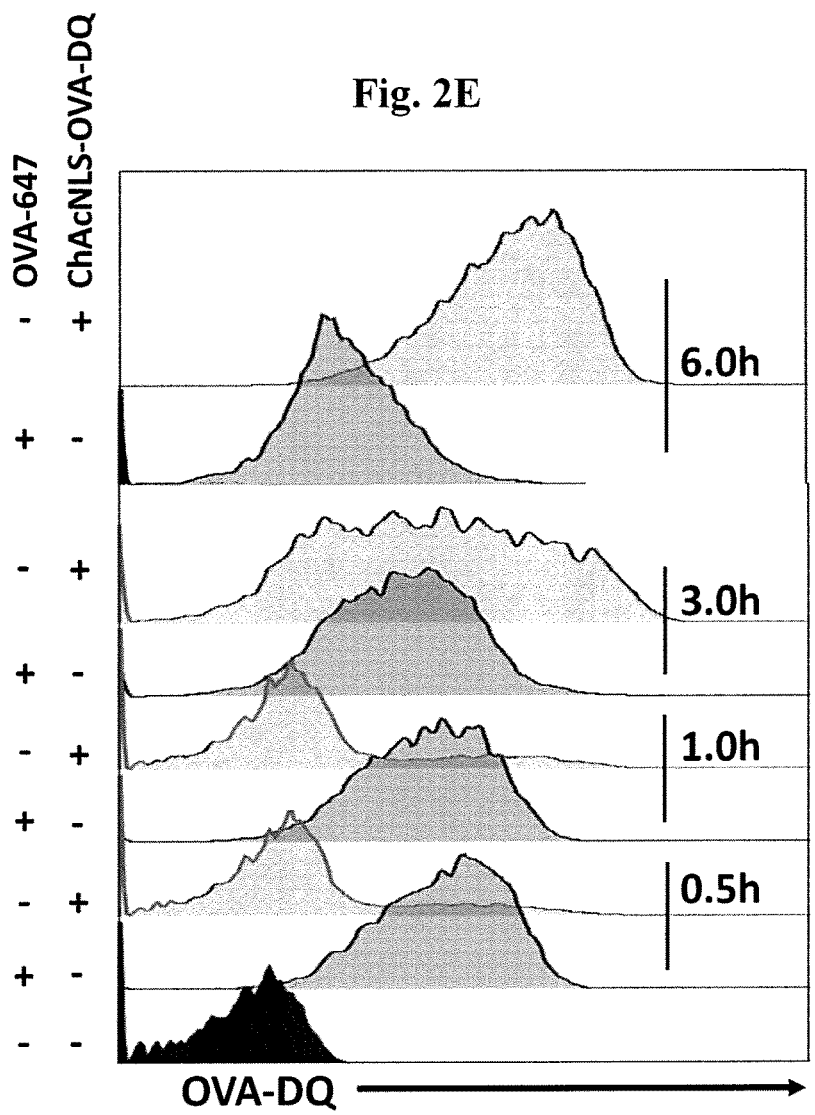
Figure 2F:
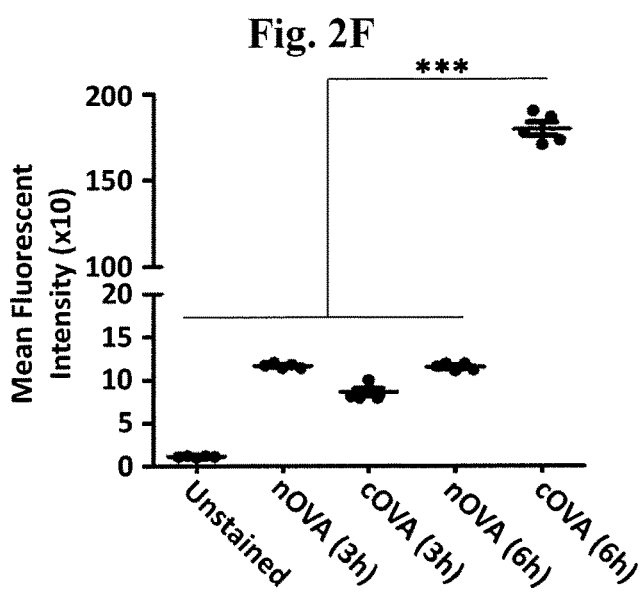

FIG. 2B shows the amount of IFN-gamma produced using OT-I-derived CD8 T cells, which is a measure of cross presentation activity. Strikingly, CD8+ T cells incubated with BMDCs and cOVA produced significantly more IFN-gamma than when incubated with the naked antigen (nOVA). FIGS. 2C and 2D shows the amount of IL-2 and IFN-gamma, respectively, produced using OT-II-derived CD4 T cells, which is a measure of classical MHC class II presentation activity. Strikingly, CD4+ T cells incubated with BMDCs and cOVA produced significantly more IFN-gamma than when incubated with the naked antigen (nOVA). In light of these observations, intracellular processing of captured OVA was then monitored. For this purpose, the ChAcNLS was cross-linked onto OVA-DQ prior to pulsing ex vivo generated primary bone marrow-derived DCs. Although an increase in differences could be depicted for both antigen conditions 3 h post-DC pulsing, the signal intensity in DCs treated with ChAcNLS-linked OVA-DQ was significantly higher 6 h post-pulsing compared to nOVA (FIGS. 2E and F). Interestingly, no differences in signal intensity could be detected between nOVA pulsing at 3 or 6 h suggesting a signal saturation (FIG. 2E). Nevertheless, these observations correlate with the antigen presentation assays using primary DCs co-cultured with OT-I (CD8) (FIG. 2B) or OT-II (CD4) T cells (FIGS. 2C and D).

Figure 2G:
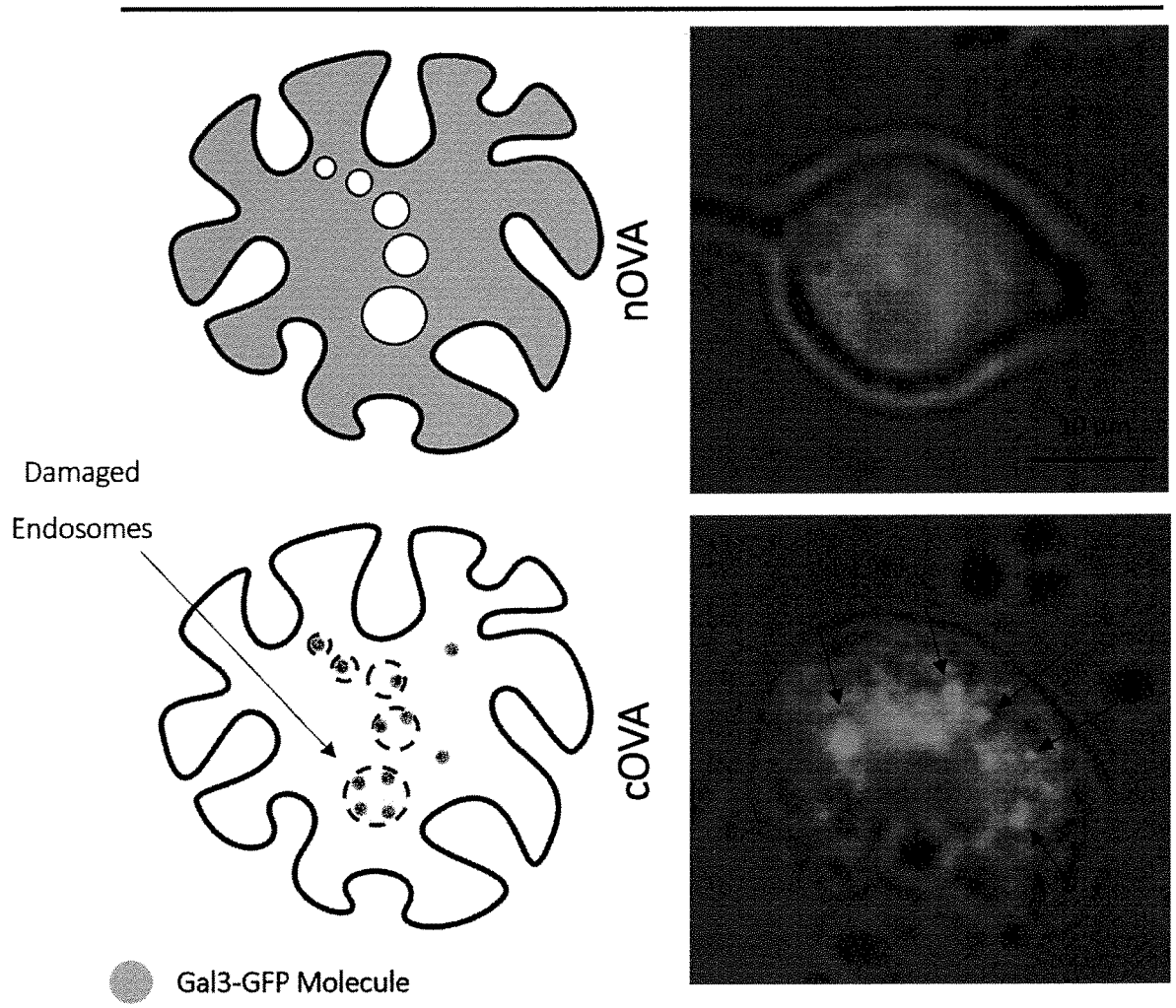

To determine if cOVA enhances endosome-to-cytosol escape, a Galectin-3 (Gal3) expression system was used as a marker of damaged endo-membranes. More specifically, Gal3 exhibits high affinity towards β-galactoside conjugates, which are normally present on the cell surface, Golgi apparatus and in the lumens of endocytic compartments. Therefore, when expressed under normal conditions, Gal3 is evenly distributed across the cytoplasm. Conversely, induction of endosomal membrane rupture allows Gal3 to access and bind luminal glycoproteins. We thus transiently transfected the DC2.4 cell line with a construct expressing the Gal3 as a fusion with the enhanced green fluorescent protein (eGFP-Gal3) to evaluate its distribution pattern. As anticipated, the GFP signal was diffusely distributed throughout the cytosol following treatment of eGFP-Gal3-expressing DC2.4 cells with nOVA (FIG. 2G-upper panel). In contrast, pulsing of DC2.4 with cOVA induces the appearance of several puncta clearly indicating signal re-localization to damages endosomes (FIG. 2G-lower panel).

Example 4: In Vivo Anti-Cancer Activity

Figure 3A:
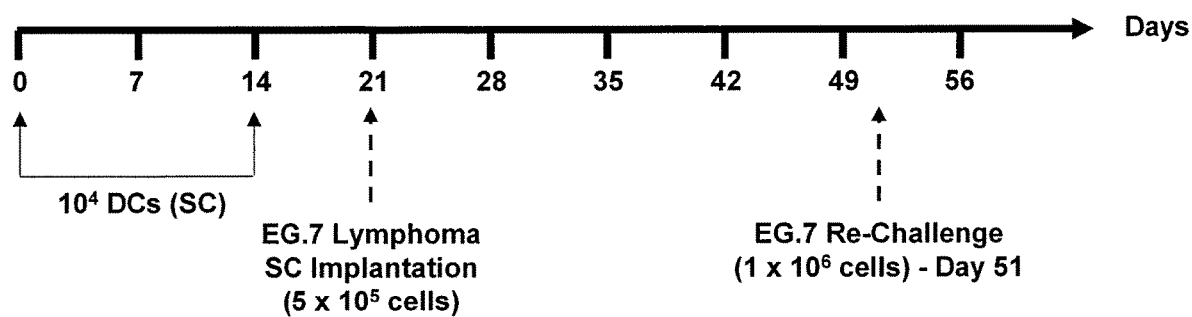
FIG. 3A-G shows the syngeneic prophylactic vaccination against T-cell lymphoma.

To determine the effectiveness of ChAcNLS-modified OVA as a prophylactic vaccine, mice were vaccinated with cOVA as either a cell-based or a stand-alone vaccine. For the cell-based vaccine, BMDCs pulsed with either nOVA or cOVA were subcutaneously injected into mice before implantation of EG.7 lymphoma cells, followed by a re-challenge. The immunization scheme is depicted in FIG. 3A.

Figure 3B:
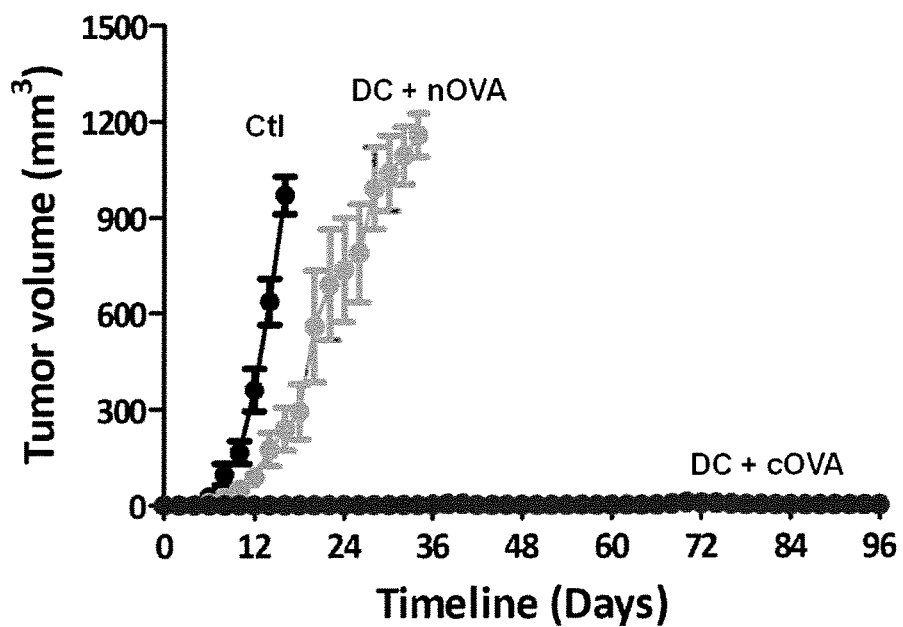
Figure 3C:
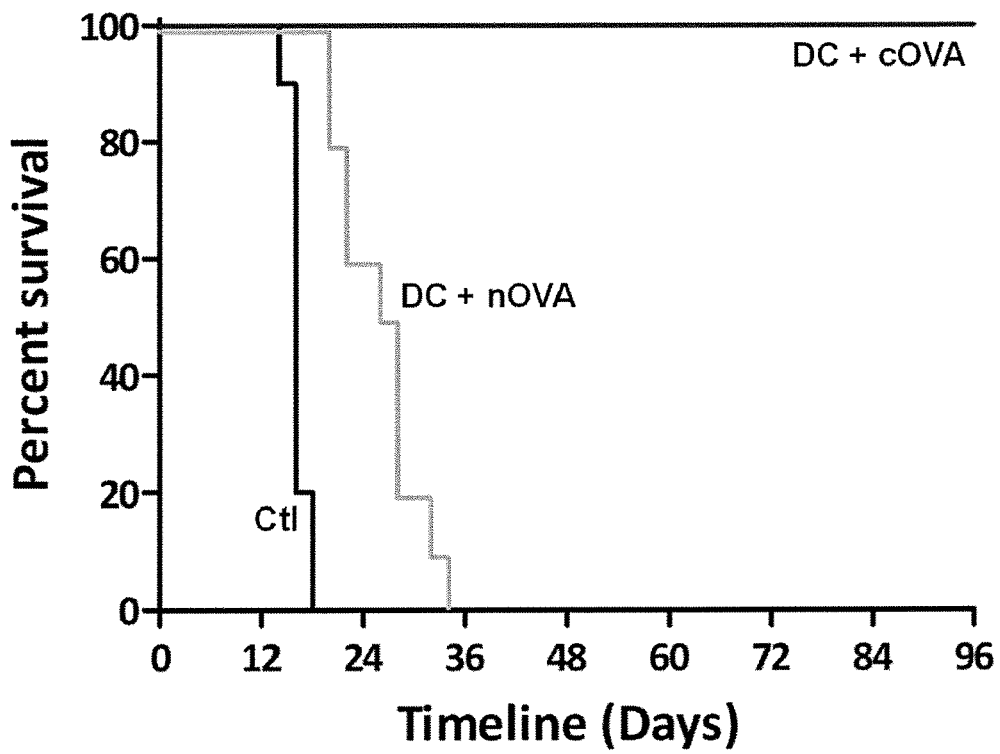
Figure 3D:
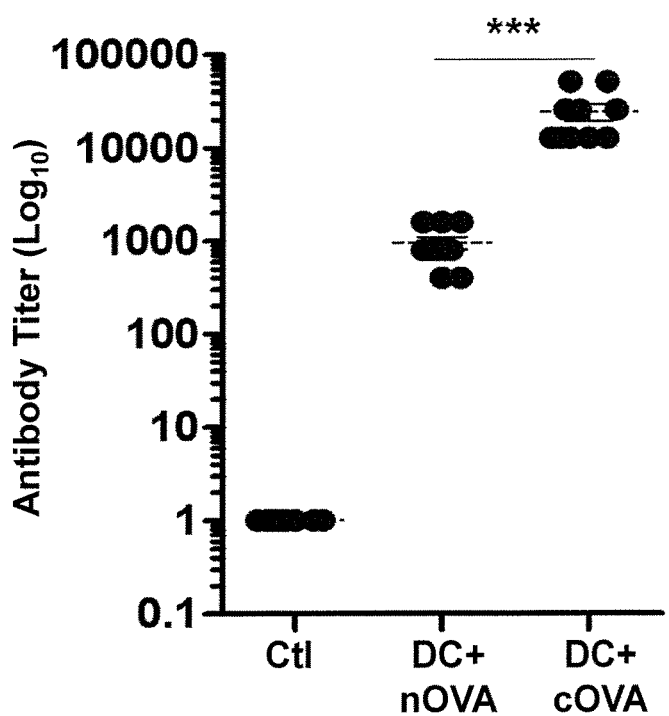
Figure 3E:
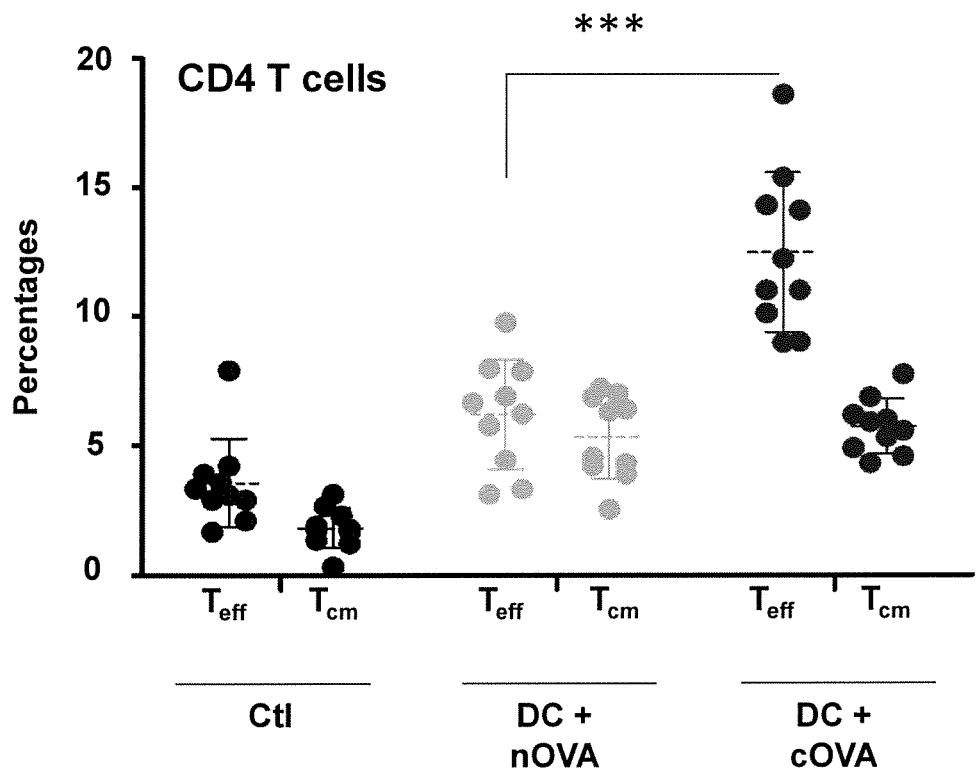
Figure 3F:
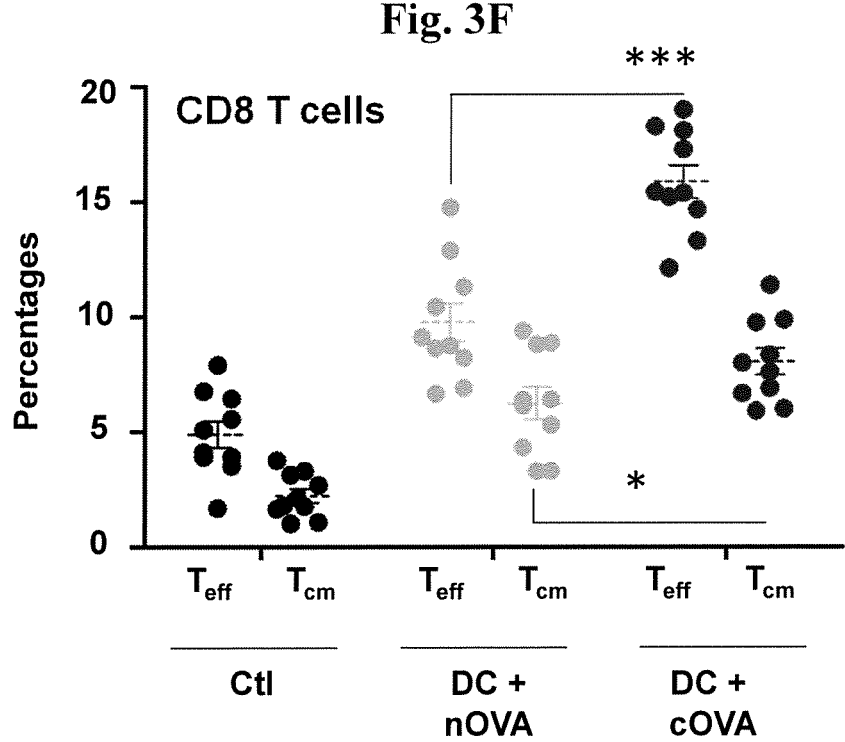
Figure 3G:
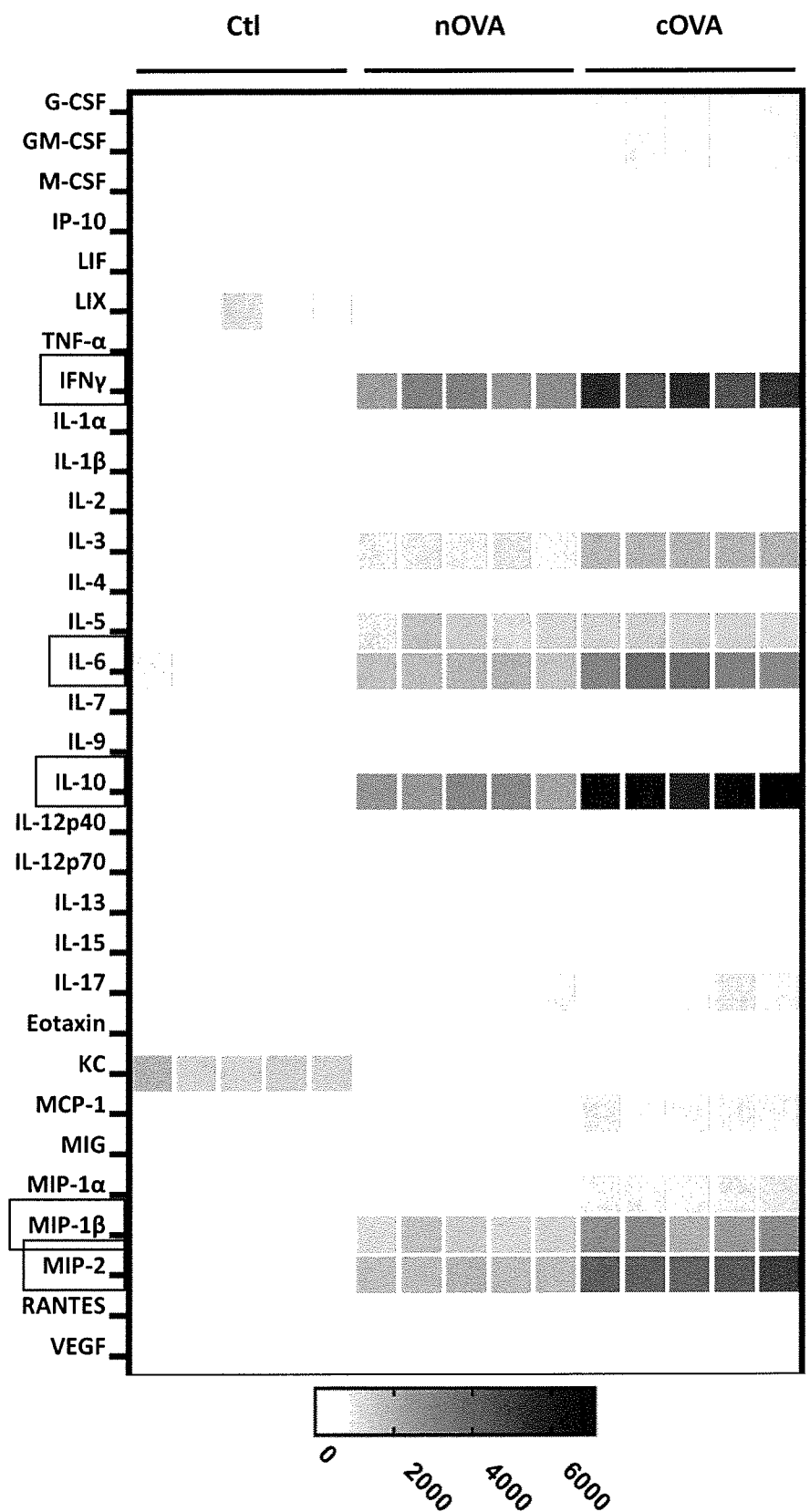

Strikingly, mice vaccinated with BMDCs pulsed with cOVA did not show any tumor growth and had a 100% survival rate, whereas control (unvaccinated) and mice vaccinated with BMDCs pulsed with nOVA developed large tumors and were more susceptible to death (FIGS. 3B and 3C). Furthermore, mice vaccinated with BMDCs pulsed with cOVA developed higher antibody titers (FIG. 3D). In addition, the level of CD4 effector (CD44hiCD62Llo) and CD8 central (CD44hiCD62Lhi) and effector memory T cells was substantially higher in the cOVA-DC group (FIGS. 3E and F). Finally, Luminex™ analysis of cytokines/chemokines derived from in vitro re-stimulated T cells show elevated levels of IFN-gamma in the cOVA group compared to nOVA-injected mice (FIG. 3G). Similar data were also observed for macrophage-inflammatory protein (MIP)-1β and MIP-2, two strong chemoattractants for monocytes/macrophages, NK cells and neutrophils, as well as interleukin (IL)-6 and IL-10, two cytokines known to support B-cell differentiation and antibody production (FIG. 3G). Altogether, the improved immune responses observed in animals vaccinated with cOVA-pulsed DCs is consistent with their acquired resistance to multiple EG.7 re-challenges and durable survival benefits.

Figure 4A:
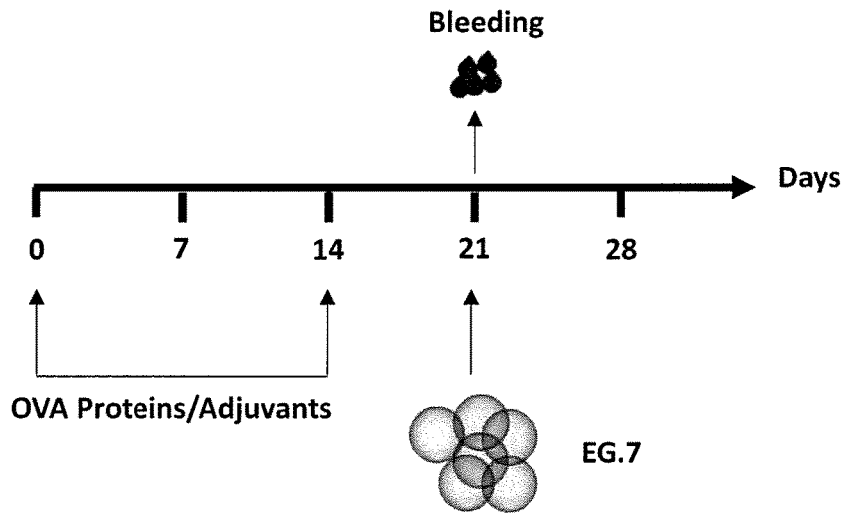
Figure 4B:
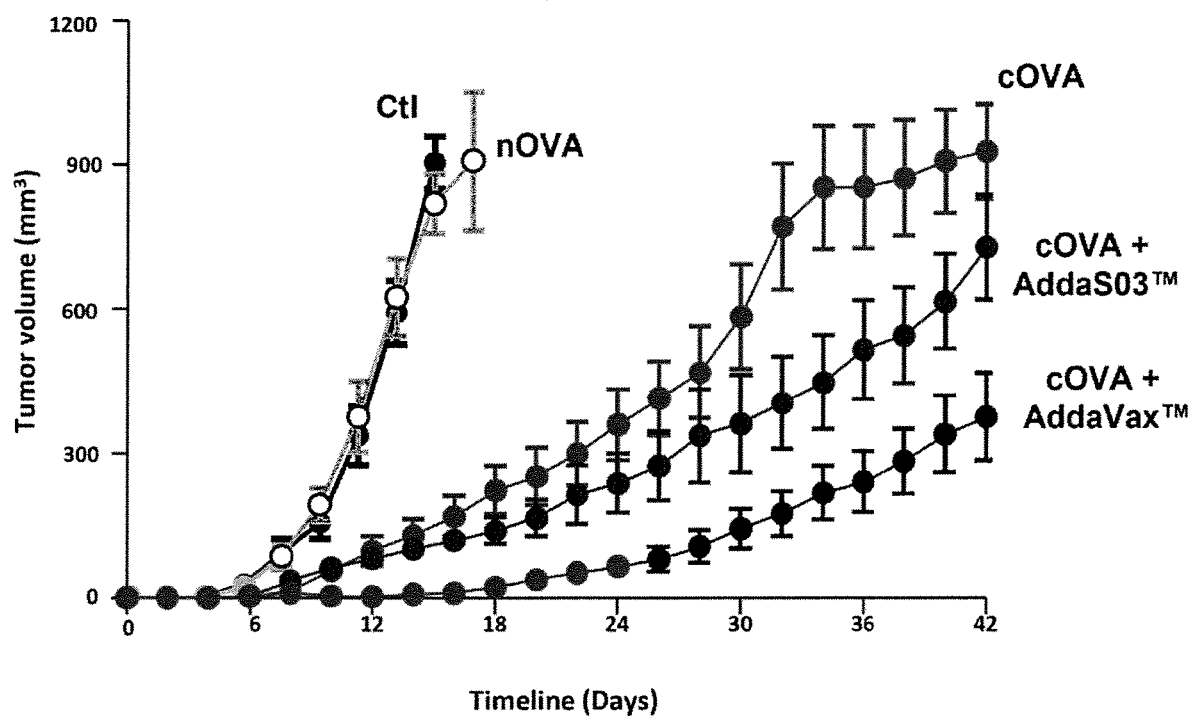

In a similar immunization scheme, mice were vaccinated with either cOVA or nOVA alone (not BMDC-pulsed) before implantation of EG.7 lymphoma cells (FIG. 4A). As shown in FIG. 4B, mice vaccinated with cOVA developed smaller tumors, had significantly increased survival rates (FIG. 4C) and antibody response (FIG. 4D) in comparison to mice vaccinated with nOVA or unvaccinated control mice. Vaccination using the two squalene-based oil-in-water emulsion adjuvants, AddaS03™ or AddaVax™, both improved the immune response potency with AddaVax triggering superior effect in cOVA-vaccinated mice.

Example 5: In Viva Therapeutic Vaccination Against T-Cell Lymphoma

Figure 5A:
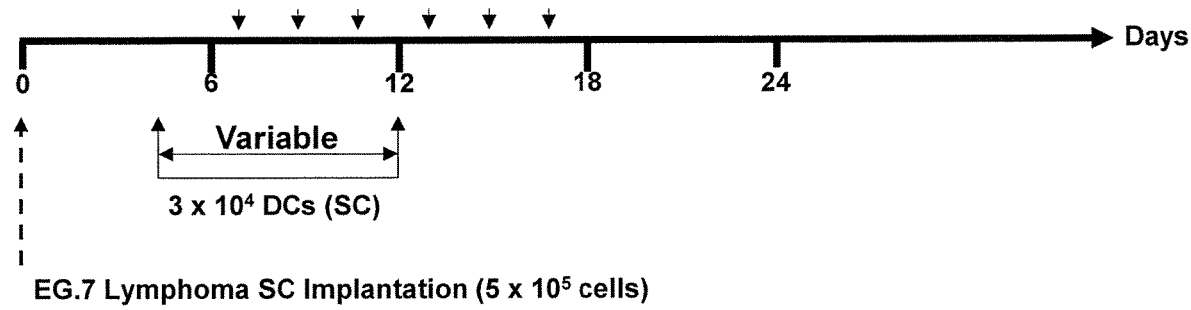
FIG. 5A-E shows the therapeutic vaccination against T-cell lymphoma.

To determine the effectiveness of bile acid-conjugated polypeptide antigens as therapeutic vaccines, mice were first implanted with EG.7 lymphoma cells then immunized with BMDCs pulsed with either nOVA or cOVA, in the presence or absence of an immune checkpoint inhibitor/anti-cancer agent anti-PD-1 antibody. The immunization scheme is shown in FIG. 5A.

Figure 5B:
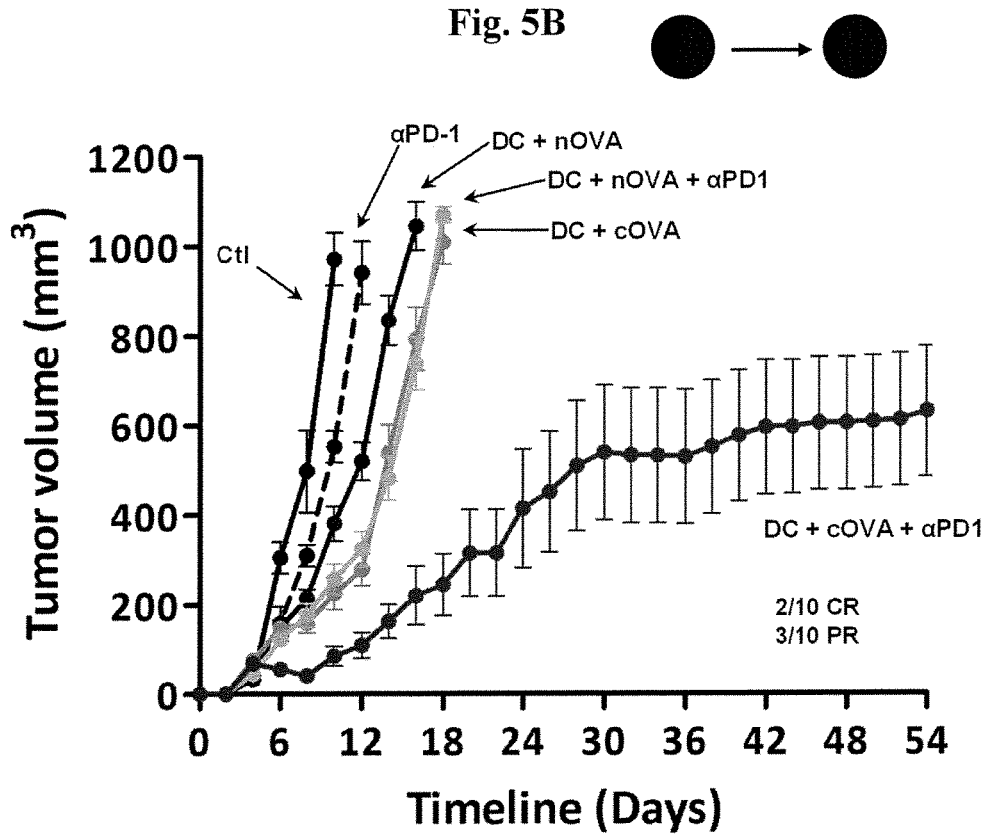
Figure 5C:
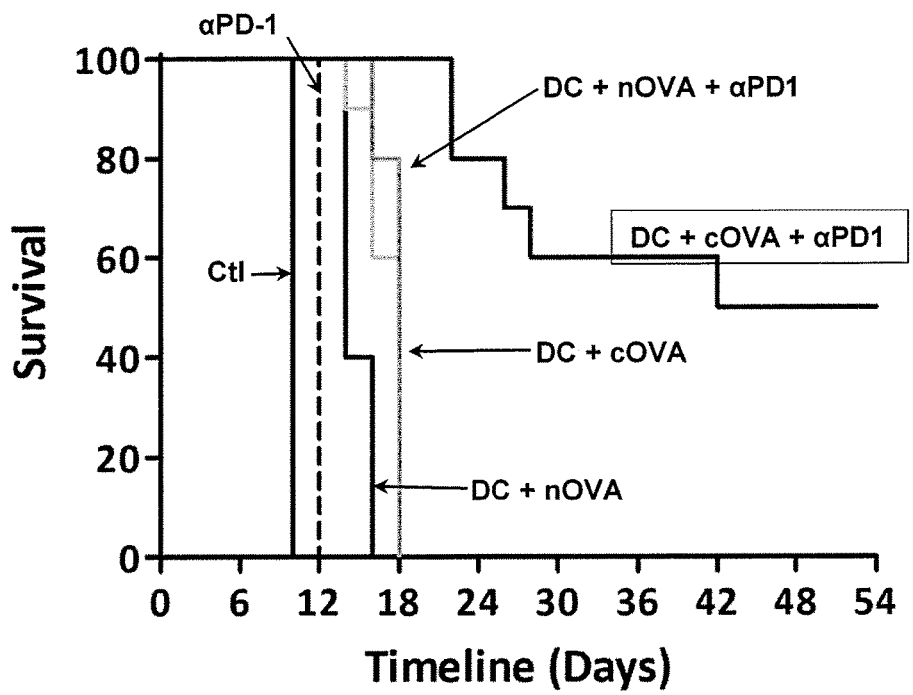
Figure 5D:
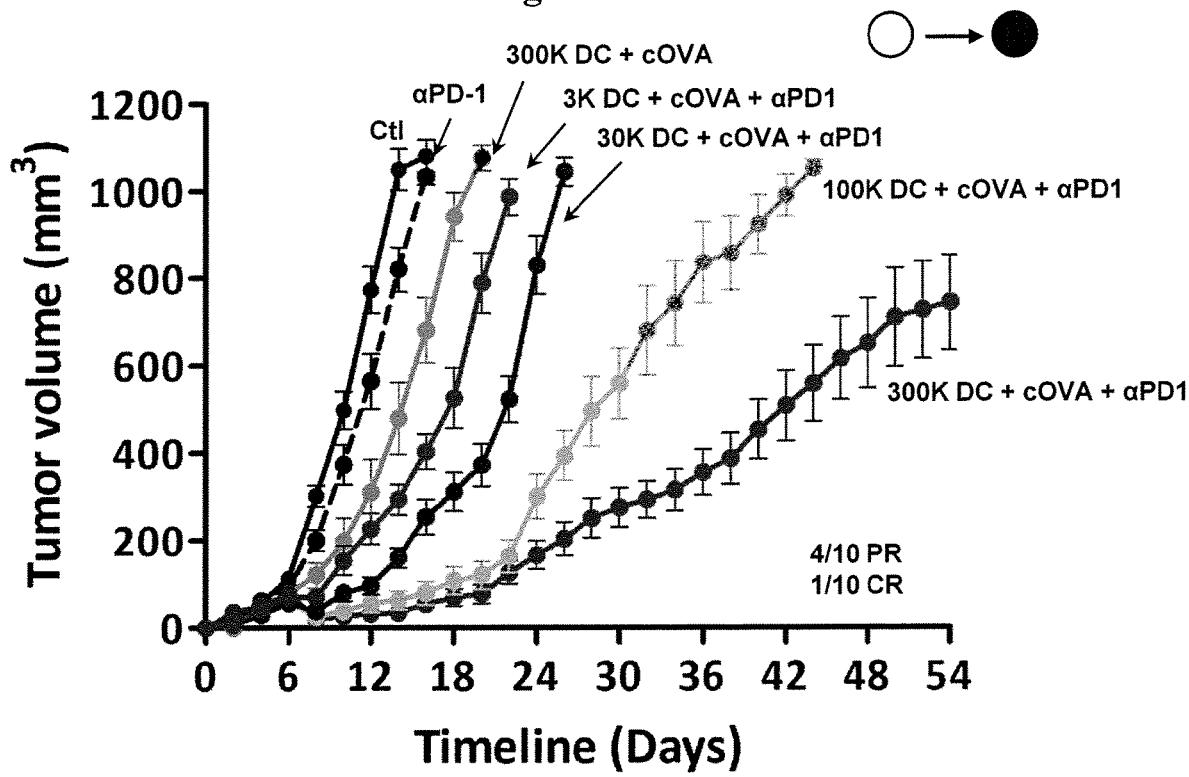
Figure 5E:
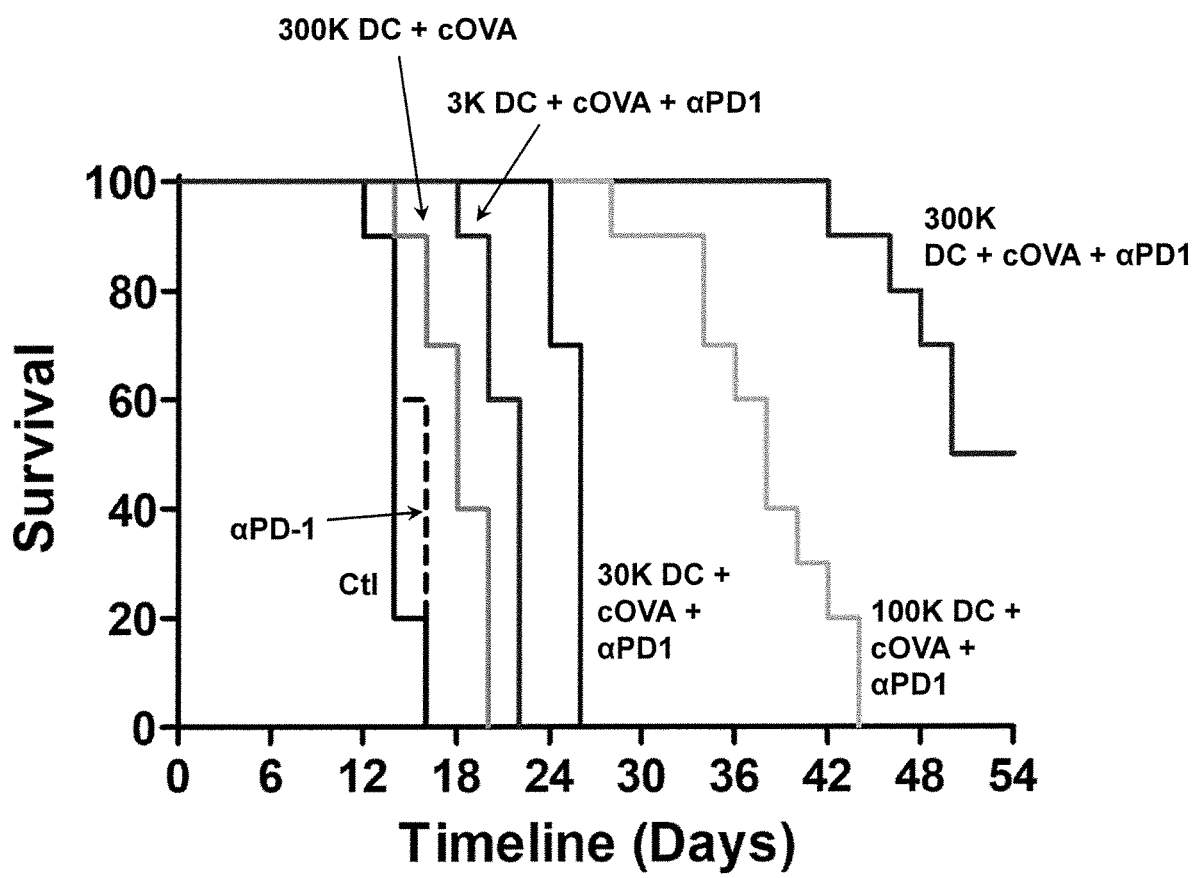

Mice immunized with BMDCs pulsed with cOVA had significantly smaller tumors (FIG. 5B) and increased survival rates (FIG. 5C) compared to mice immunized with anti-PD-1 antibody alone or BMDCs pulsed with nOVA. Strikingly, mice treated with a combination therapy of anti-PD-1 Ab and BMDCs pulsed with cOVA showed synergistic efficacy in treating T cell lymphoma in mice, as shown by the decrease in tumor volumes and increase in survival rates. This synergistic effect was directly correlated to the number of BMDCs pulsed with cOVA immunized in mice (FIGS. 5D and 5E).

Figure 6A:
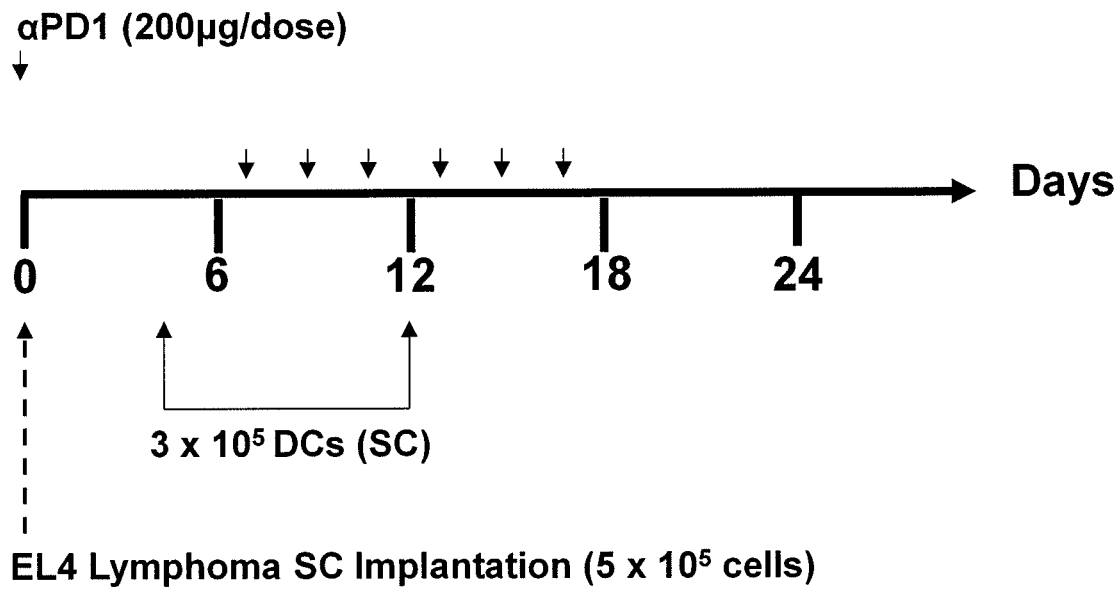
FIG. 6A-F shows the tumor lysate-based therapeutic vaccination against T-cell lymphoma.
Figure 6B:
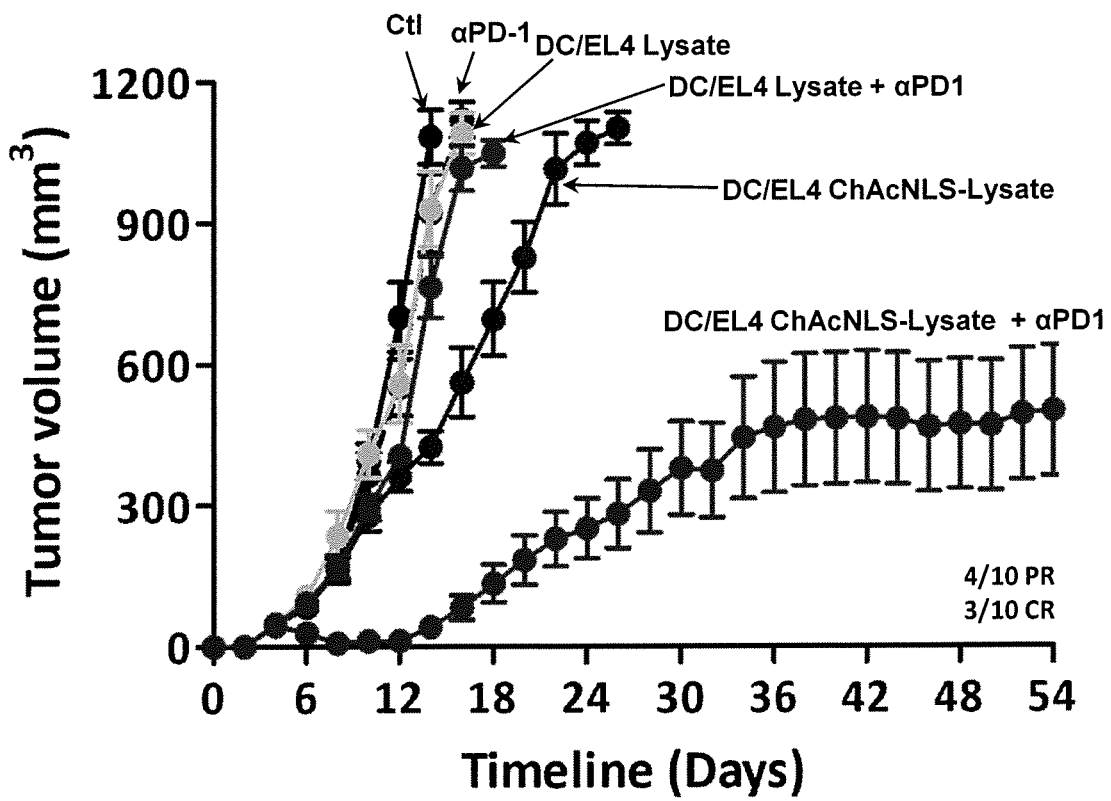
Figure 6C:
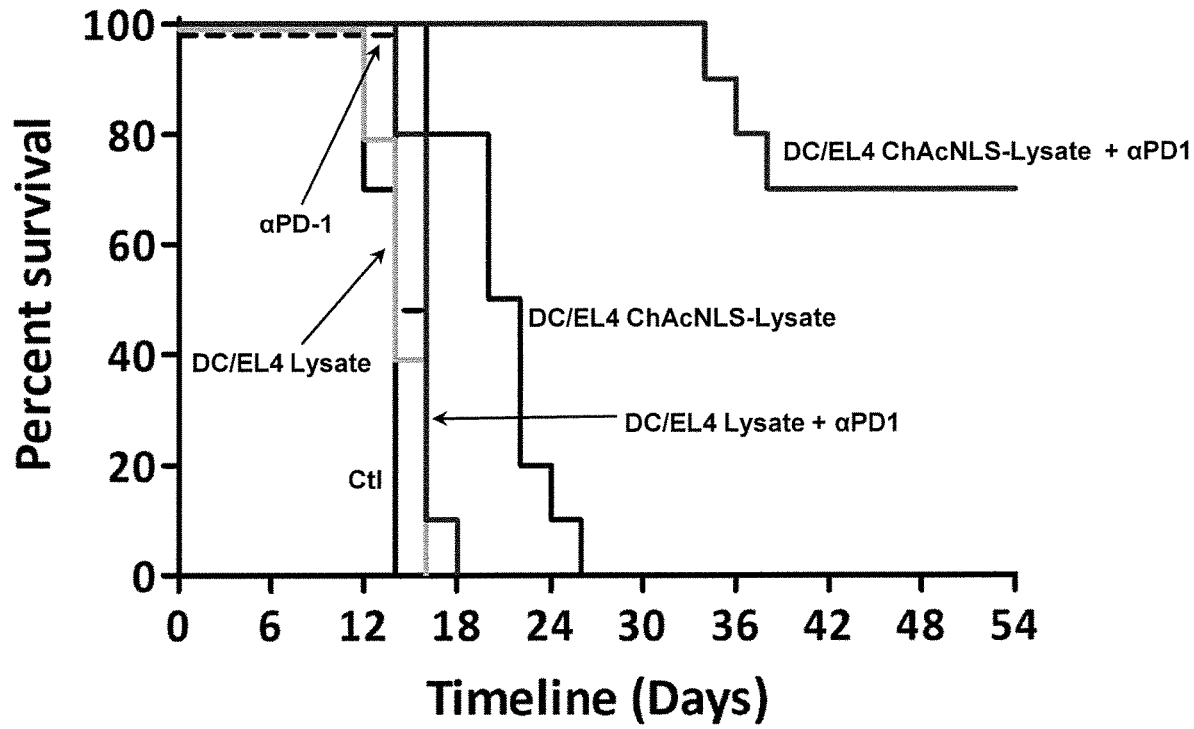
Figure 6D:
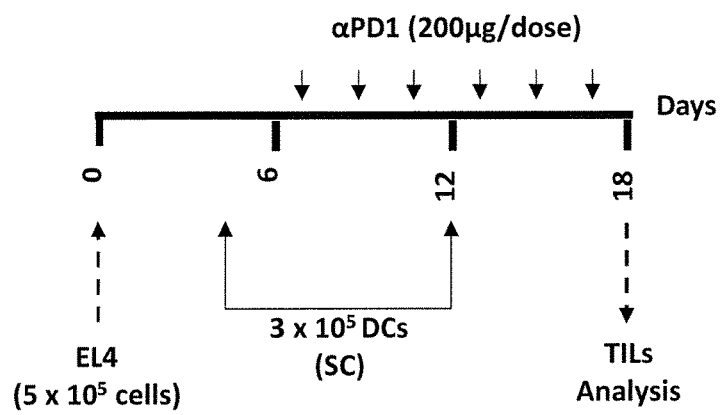
Figure 6E:
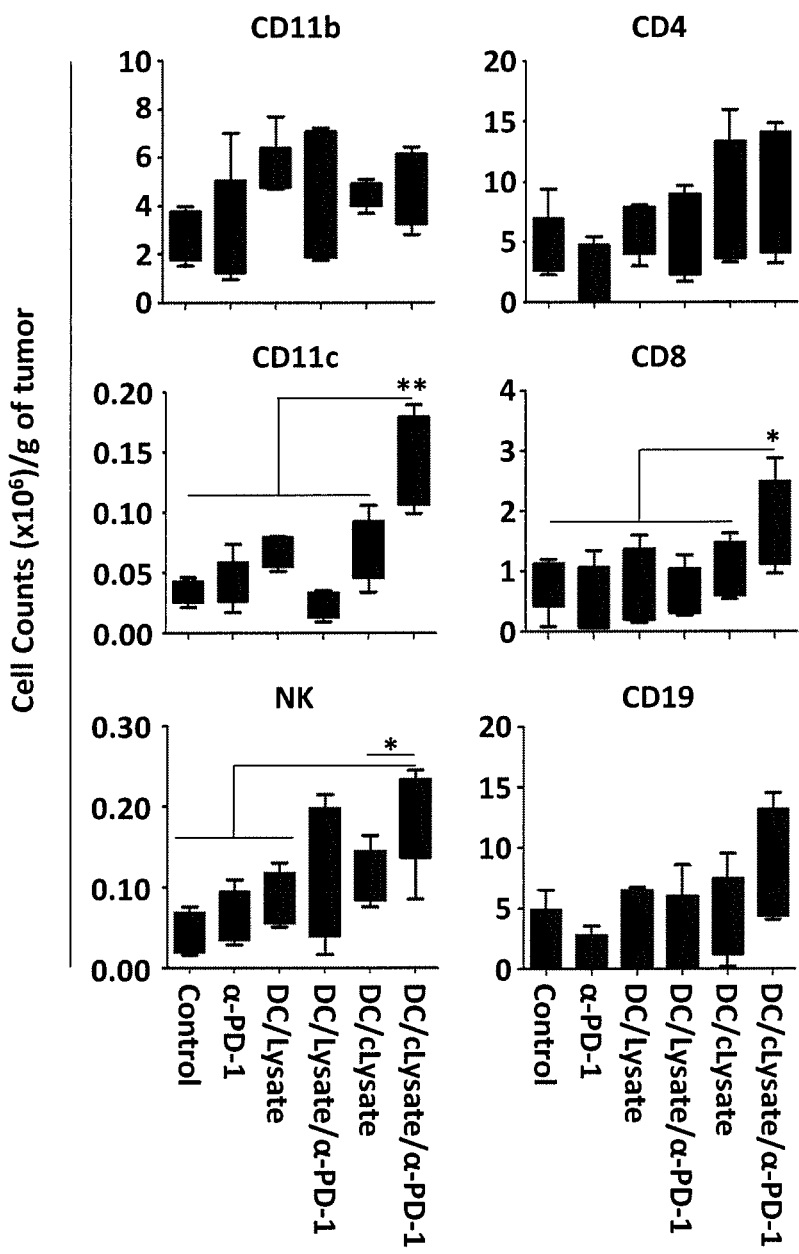
Figure 6F:
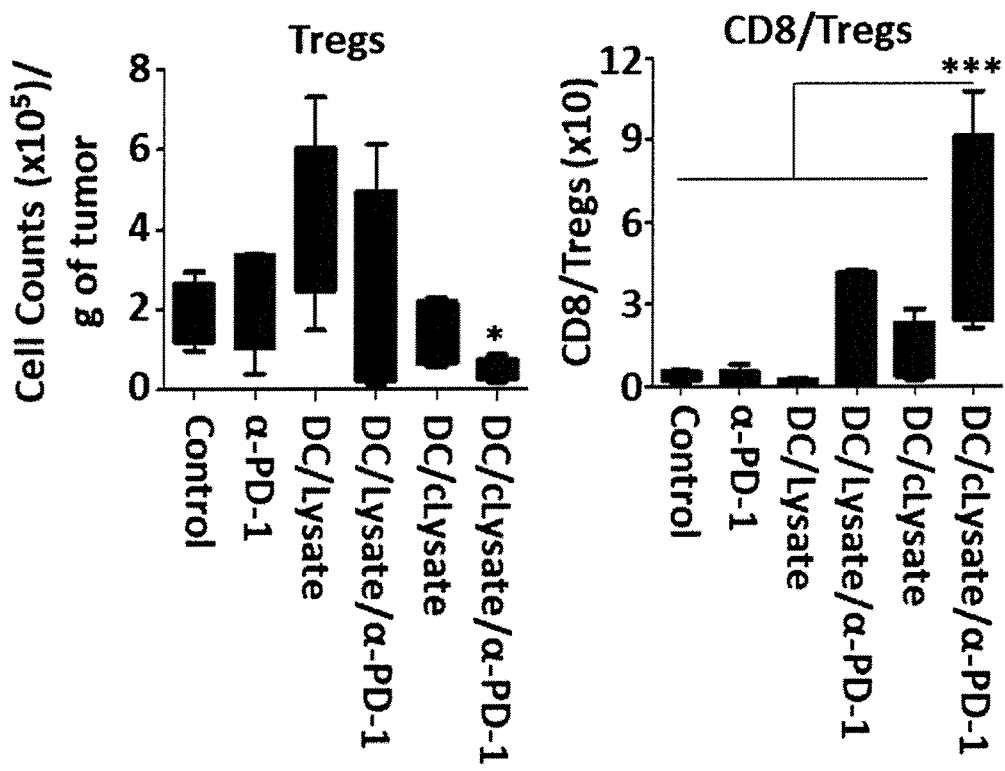

Finally, ChAcNLS was covalently linked to EL4 T cell lymphoma lysates to determine the effect of an antigen specific therapeutic vaccine. Mice implanted with EL4 T cell lymphoma cells were immunized with BMDCs pulsed with either EL4 lysates alone or ChAcNLS-EL4 lysates, in the presence or absence of anti-PD-1 antibody (FIG. 6A). Similar to with cOVA, mice immunized with BMDCs pulsed with ChAcNLS-EL4 lysates had significantly smaller tumors and increased survival rates compared to mice immunized with anti-PD-1 Ab alone or BMDCs pulsed with EL4 lysates independent of the presence of anti-PD-1 Ab (FIGS. 6B and 6C). Of note, a synergistic effect combining BMDCs pulsed with ChAcNLS-EL4 lysates and anti-PD1 Ab treatment was seen, as tumor growth in the mice plateaued at around 36 days and the mice had a 70% survival rate at the conclusion of the study (54 days). These observations were further supported by tumor-infiltrating lymphocyte (TIL) analysis (FIG. 6E), which revealed enhanced recruitment of CD8, NK and CD11c immune effector cells in the ChAcNLS-EL4 lysate ("cLysate")-pulsed DCs/PD-1 (FIG. 6E). In sharp contrast, the level of regulatory CD4 T cells (Tregs) was greatly diminished in the same group (FIG. 6E), bolstering the idea that combining cLysate-pulsed DCs to PD-1 favors inflammation by tipping the balance in favour of CD8 T cells versus suppressive Tregs infiltration (FIG. 6F). Overall, these findings indicate that "off-the-shelf" allogeneic DCs treated with the ChAcNLS-EL4 lysate formulation can be effectively exploited as universal vaccines to trigger potent anti-tumoral responses.

Example 6: In Vivo Therapeutic Vaccination Against SARS-CoV-2

To determine the effectiveness of bile acid-conjugated polypeptide antigens as therapeutic vaccines for microbial infections, particularly viral infections such as with SARS-CoV-2, a vaccine composed of ChAcNLS covalently linked to SARS-CoV-2 Spike protein was constructed, similar to the construction of the cOVA vaccine as described in Examples 1, 2, and 4.

FIGS. 7A and 7B shows the SARS-CoV-2 Spike protein used for the formulation of ChAcNLS-Spike-CoV-2, and a schematic diagram of the ribbon structure of SARS-CoV-2 Spike protein (Wuhan strain D6140) with lysine residues that are predicted to be highly, moderate or poorly accessible lysine residues, similarly to OVA. As better depicted by the amino acid sequence of SARS-CoV-2 Spike protein (SEQ ID NO: 3; FIG. 7B), over 50% of the lysine residues are predicted to be accessible (highlighted in black) for ChAcNLS conjugation.

Figure 8A:
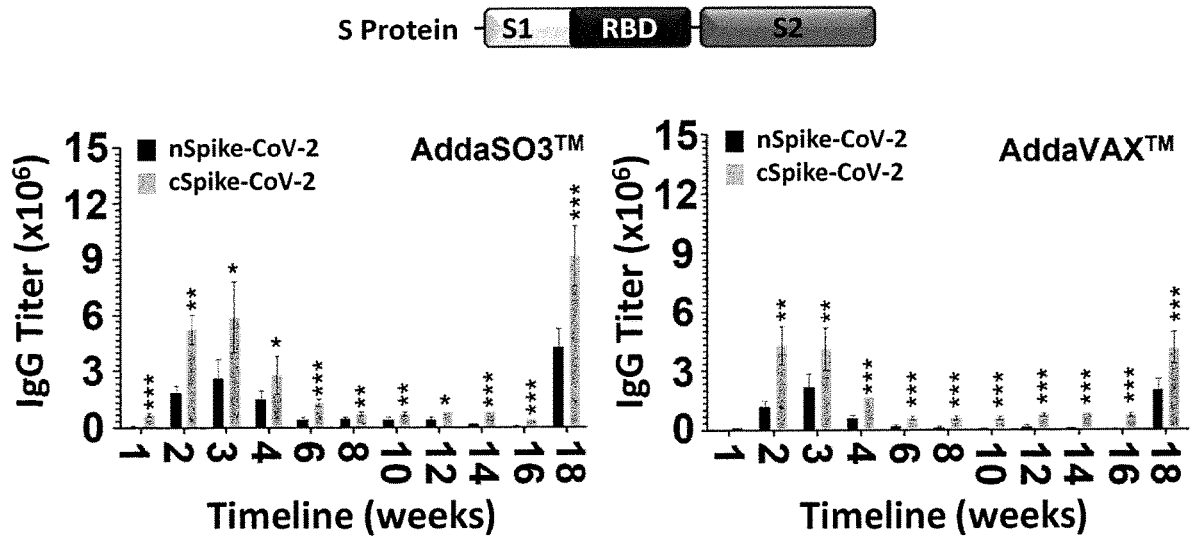
Figure 8B:
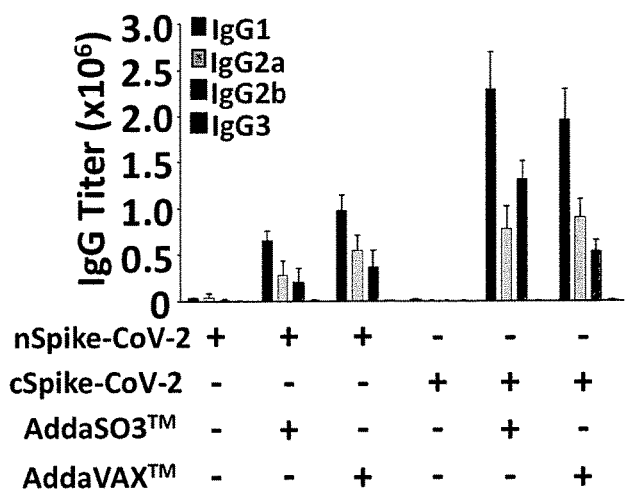

Mice were vaccinated with the full-length "naked" Spike-CoV-2 (unconjugated; nSpike-CoV-2; black bars) or with ChAcNLS-Spike-CoV-2 ("cSpike-CoV-2"; grey bars) in the presence of AddaS03 or AddaVax adjuvants (FIG. 8A). Elevated IgG titers against the Spike protein were observed in mice vaccinated with cSpike-CoV-2, in comparison to unconjugated nSpike-CoV-2, in the presence of either adjuvant. These IgG antibodies were mostly of IgG1 isotype, however, significant levels of IgG2a and IgG2b were observed (FIG. 8B).

Figure 8C:
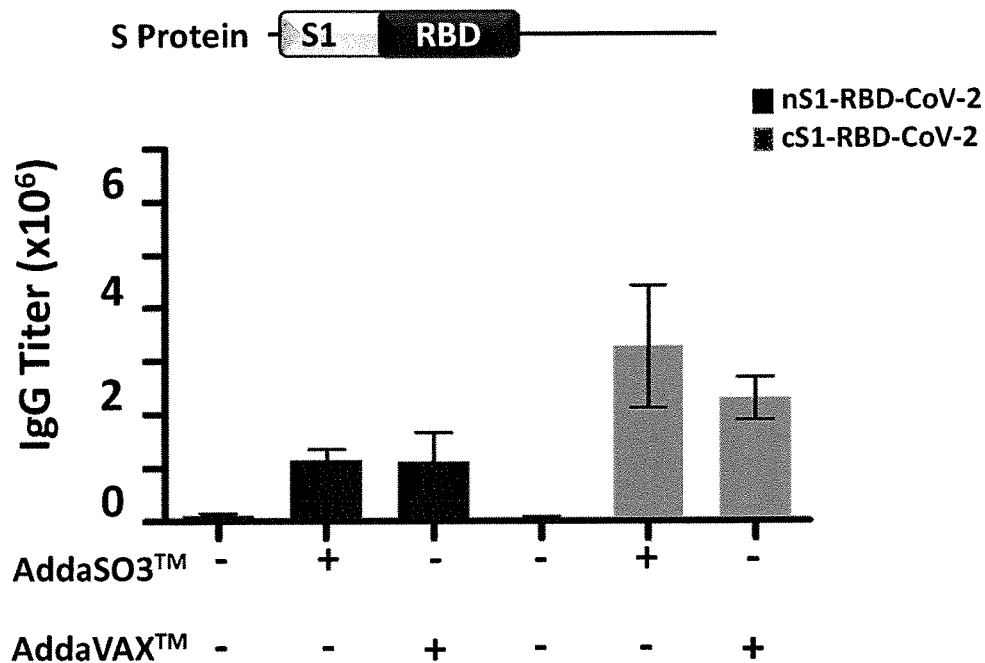
Figure 8D:
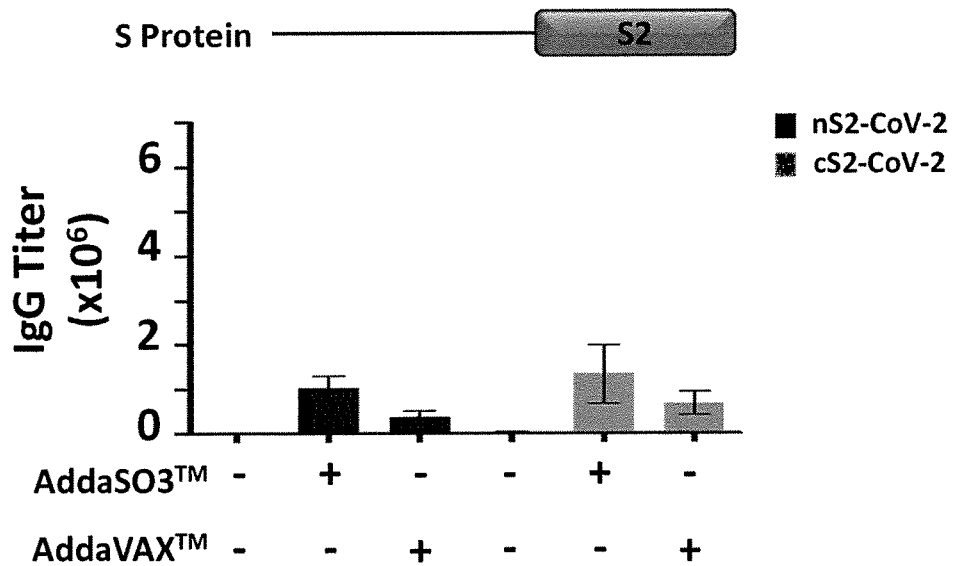

To evaluate the immunogenicities of the different domains of SARS-CoV-2 Spike protein, mice were also vaccinated with the unconjugated or conjugated vaccines containing S1-RBD or S2 portions. Antibody titers from mice vaccinated with the S1-RBD and S2 portions of the CoV-2 Spike protein, in the presence of AddaS03 or AddaVax adjuvants were significantly elevated, as shown in FIGS. 8C and 8D.

Figure 8E:
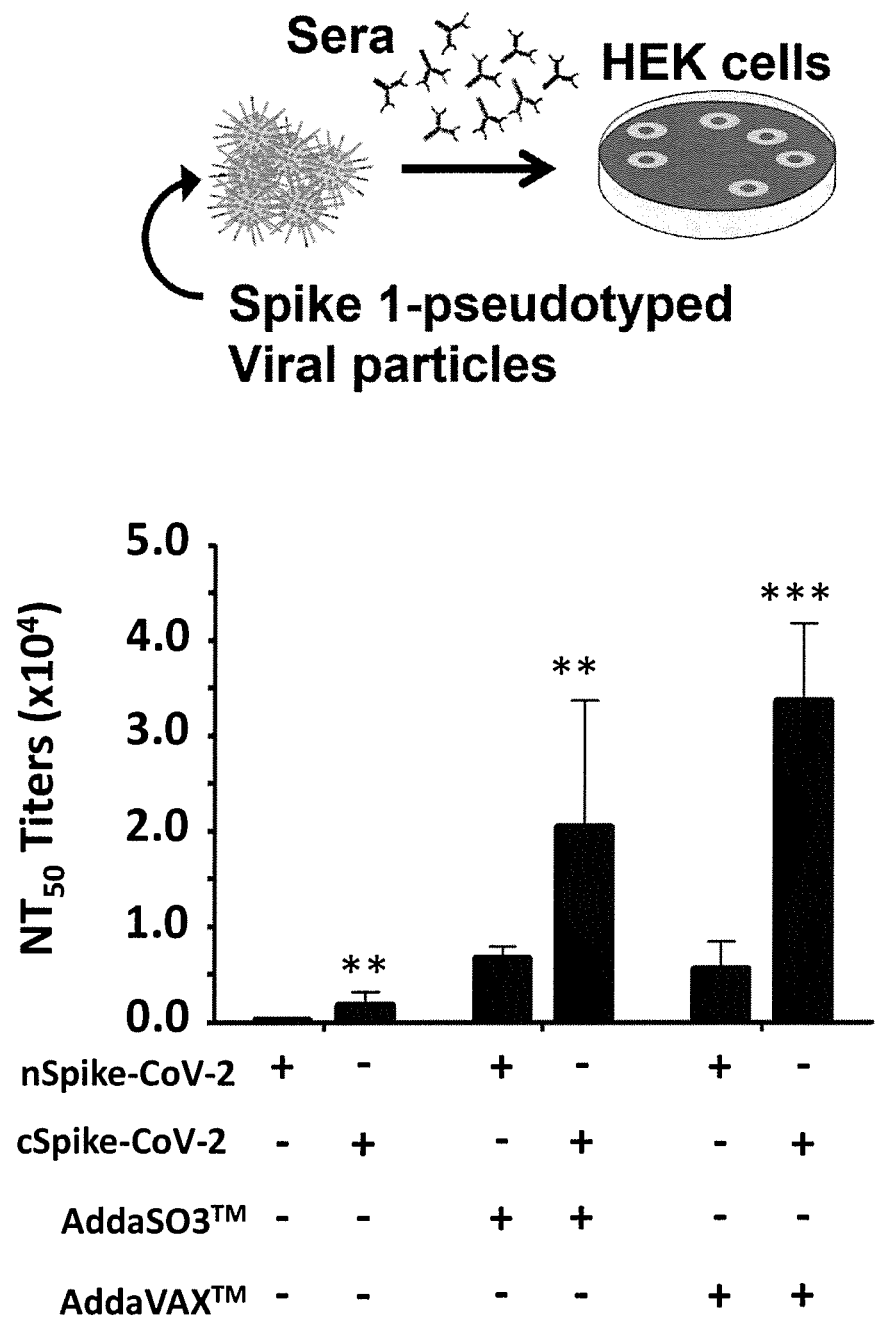

To evaluate whether the anti-Spike IgG antibodies from vaccinated mice possessed neutralizing activity, an in vitro infectivity neutralization assay was developed using Spike 1-pseudotyped viral-like particles and HEK cells. As show in FIG. 8E, sera from mice vaccinated with cSpike-CoV-2 were more efficient at inhibiting viral infection of HEK cells, and therefore had stronger neutralizing activity, as compared to nSpike-CoV-2, as shown with by $NT_{50}$ titers.

Figure 9A:
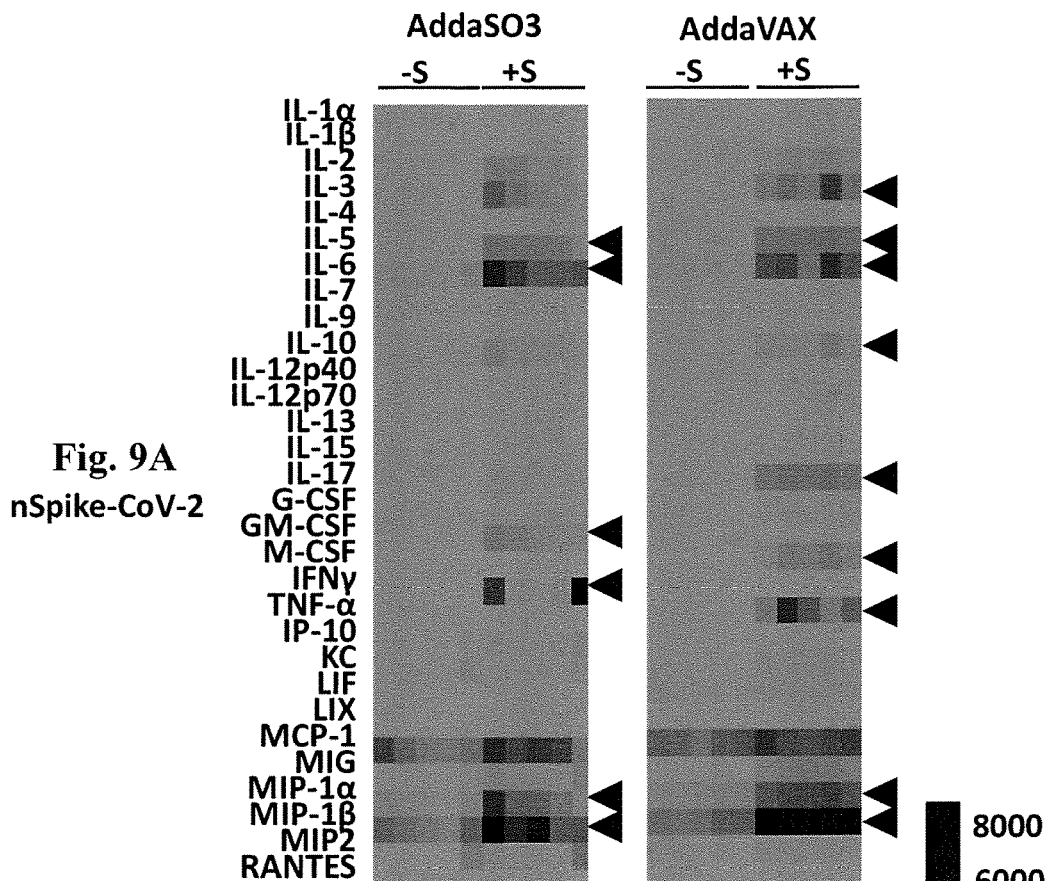
Figure 9B:
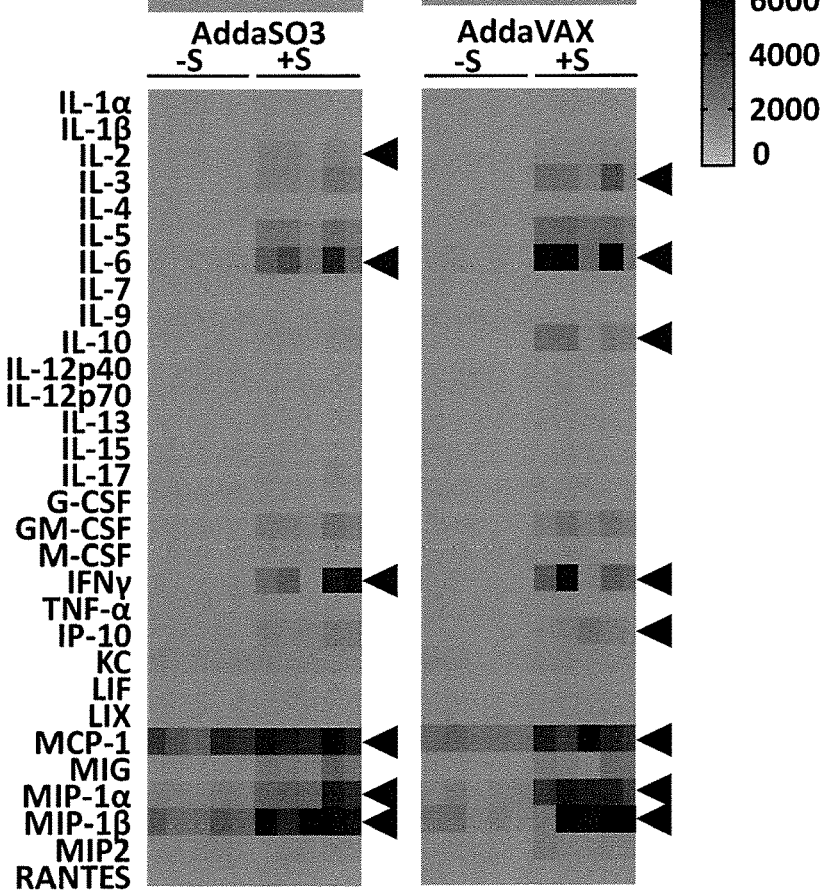

Vaccines composed of Spike protein conjugated to ChAcNLS were shown to be efficient in generating a strong humoral response. To determine whether the same vaccines were efficient at generating a cellular response, cytokine profiling following T-cell re-stimulation in vitro was assessed in mice vaccinated with nSpike-CoV-2 or cSpike-CoV-2 in the presence of two different of adjuvants. Results are shown in FIGS. 9A and 9B. In mice vaccinated with cSpike-CoV-2, a strong IFN-γ response was observed with either adjuvant, as compared to vaccination with nSpike-CoV-2, which is indicative of a strong and consistent Th1 response required for control of viral infections.

Figure 10A:
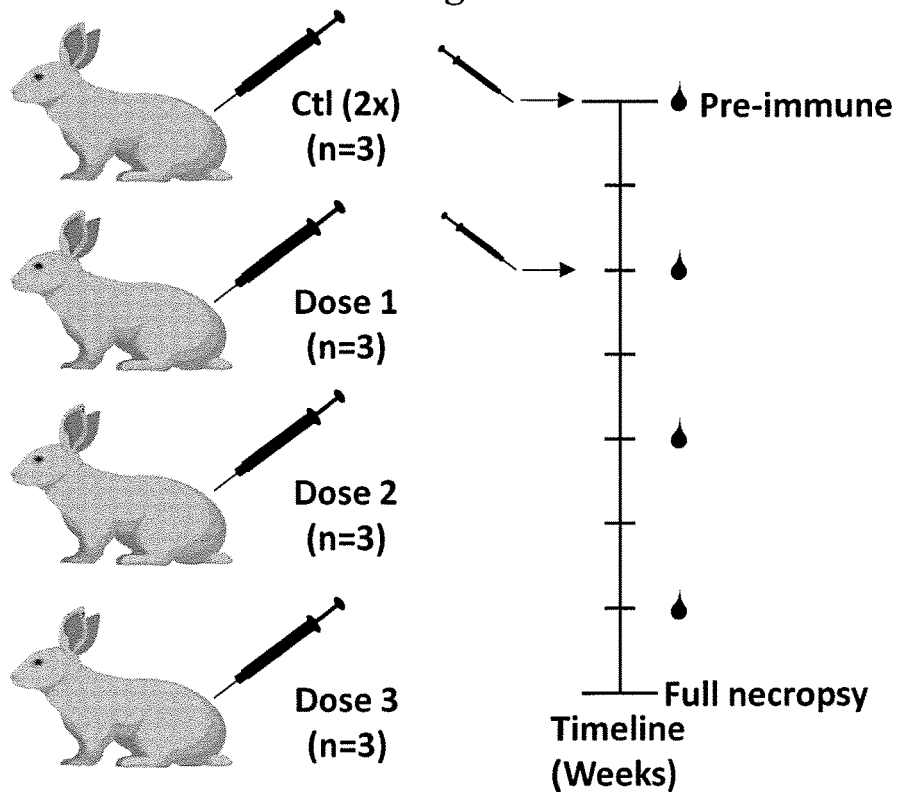
Figure 10B:
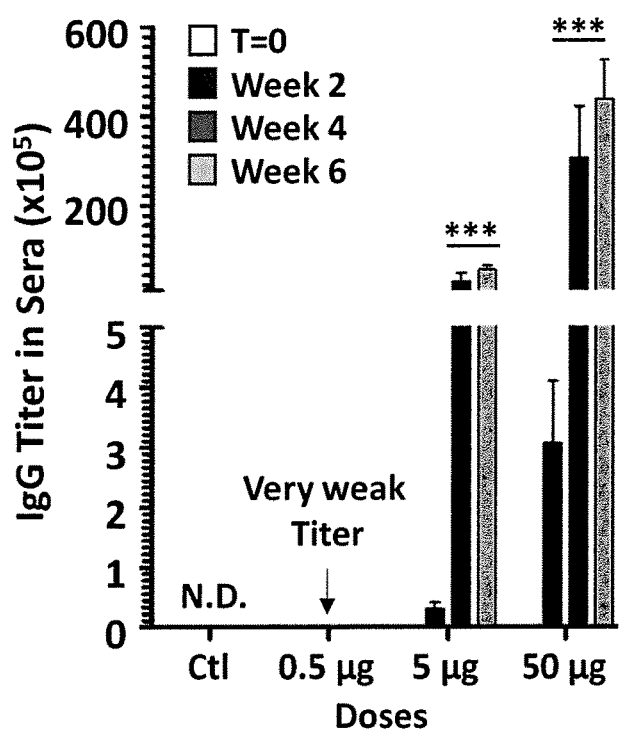
Figure 11A:
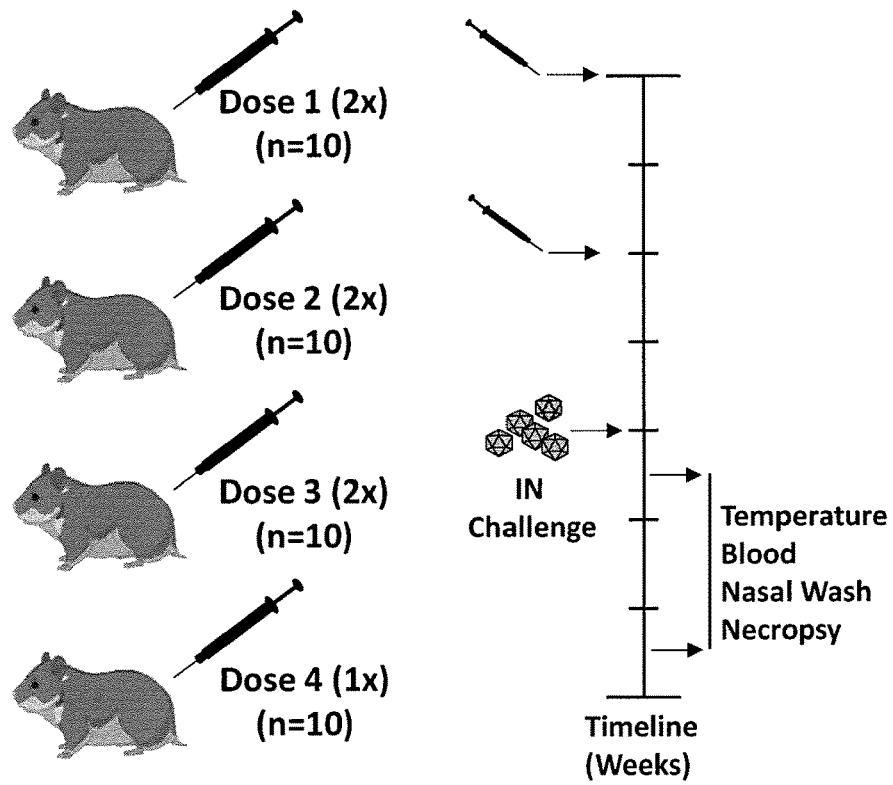
Figure 11B:
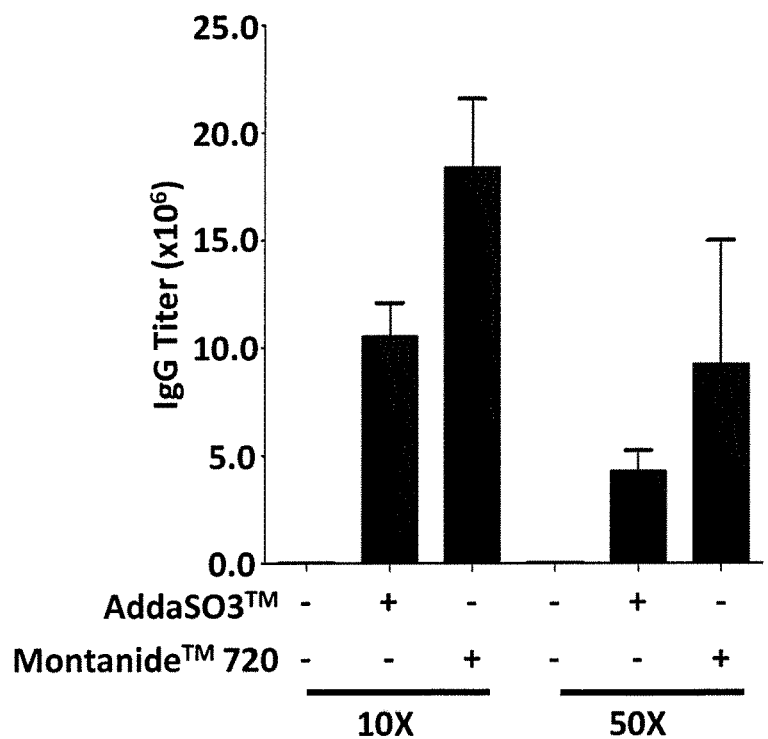

To further evaluate the immunogenicity of the SARS-CoV-2 vaccines, rabbits and hamsters were vaccinated with different doses of cSpike-CoV-2 in the presence of different adjuvants. FIG. 10A-B shows a schematic diagram (FIG. 10A) of the vaccination design in rabbits with cSpike-CoV-2 and IgG titers (FIG. 10B) at different timepoints and doses. FIG. 11A-B shows the evaluation of the therapeutic efficacy of cSpike-CoV-2 in a challenge model. FIG. 11A-B shows a schematic diagram (FIG. 11A) of the experimental design for the vaccine efficacy study in hamsters and IgG antibody titers (FIG. 11B) in response to the cSpike-CoV-2 vaccine mixed with the FDA-approved (GMP grade) MONTANIDE™ ISA 720 VG adjuvant or AddaS03. Here, the vaccines were tested using excess molar ratios of ChAcNLS to Spike-CoV-2 protein, 10× and 50×. Prior to the third dose, hamsters were challenged intranasally with the SARS-CoV-2 Delta variant. In general, the vaccines at all doses were well tolerated by rabbits and hamsters and generated strong humoral responses.

Figure 12A:
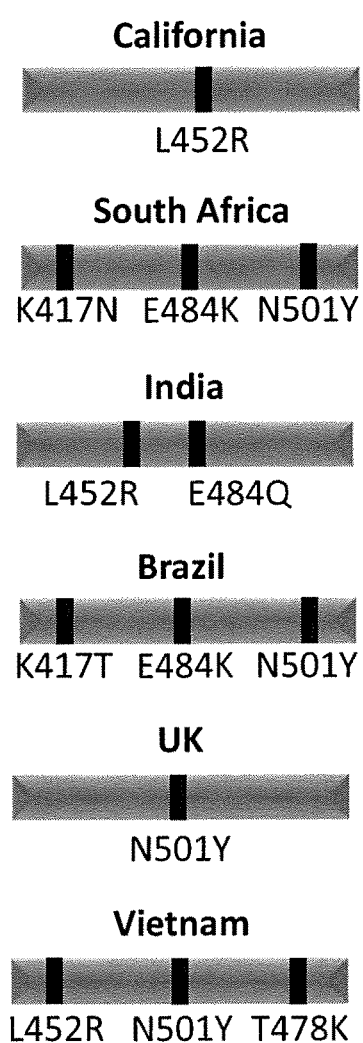
Figure 12B:
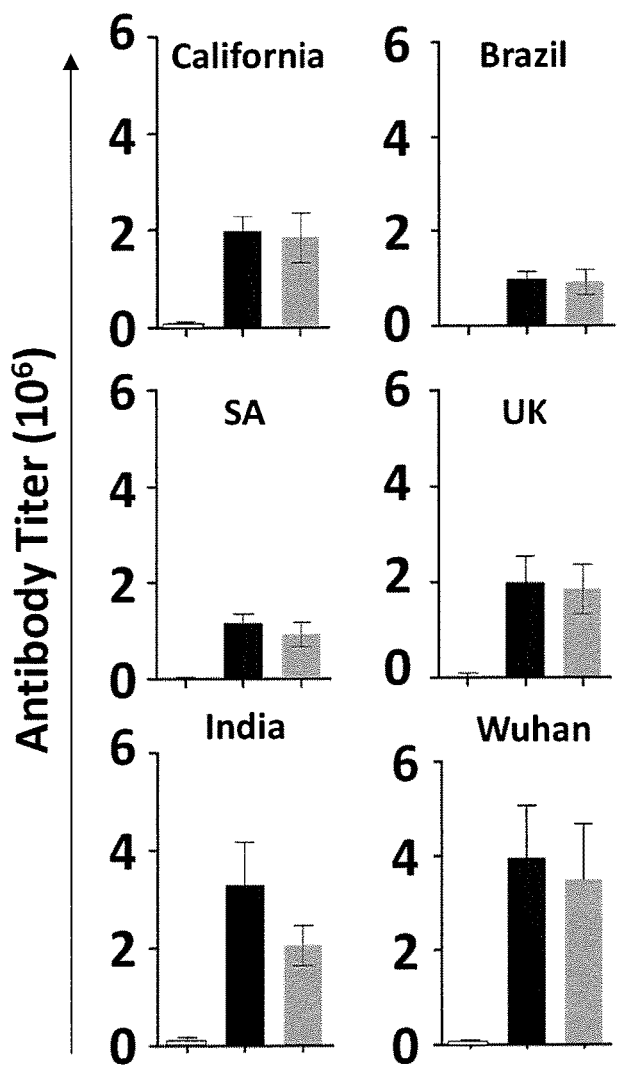
Figure 12C:
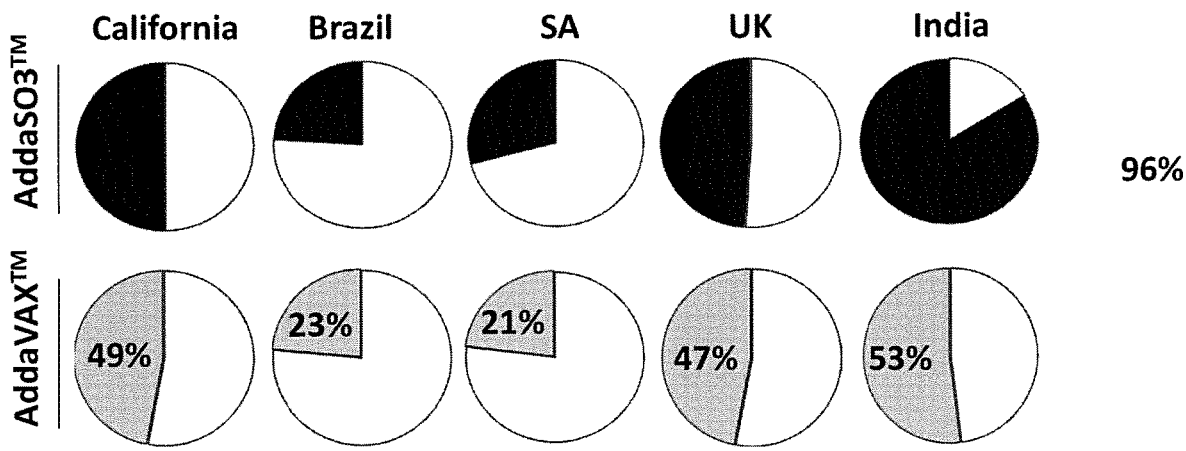
Figure 12D:
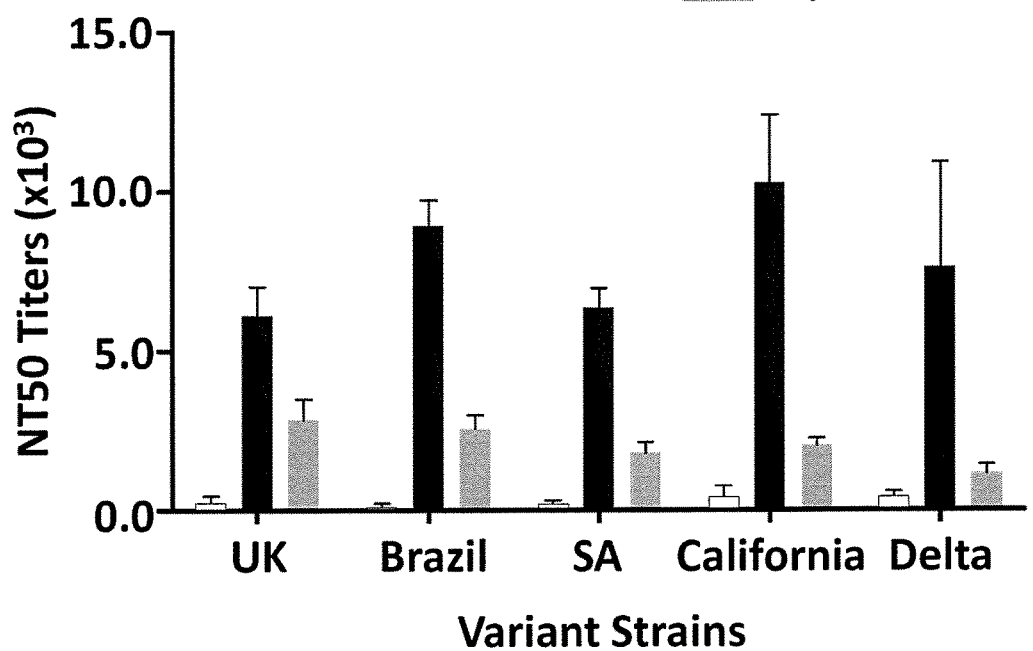
Figure 13A:
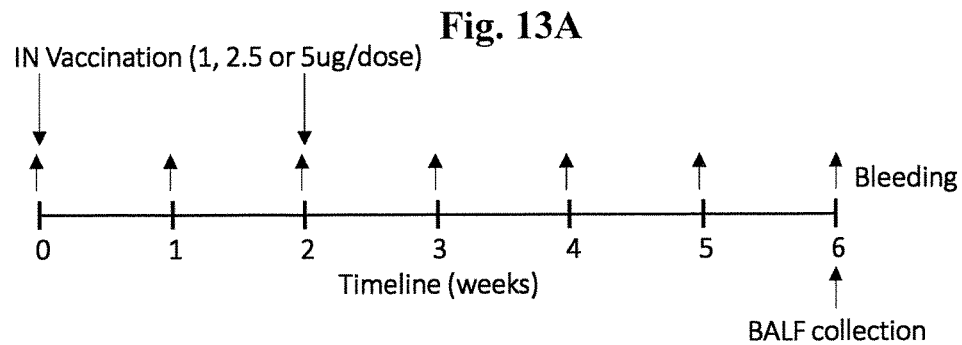
Figure 13B:
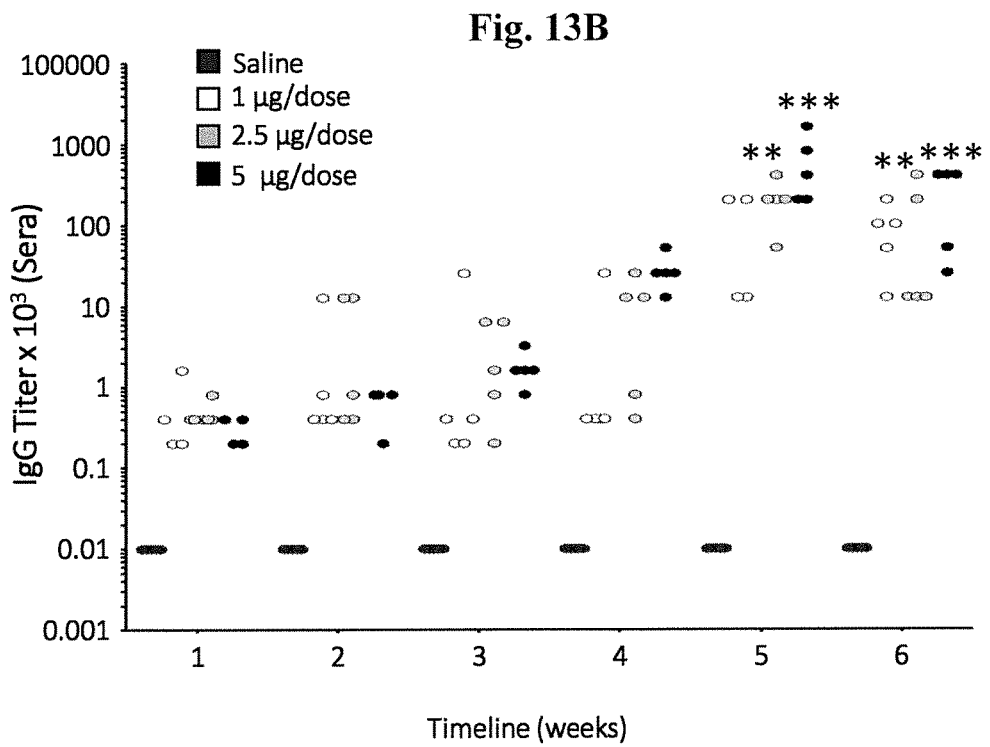
Figures 13C, 13D, 13E:
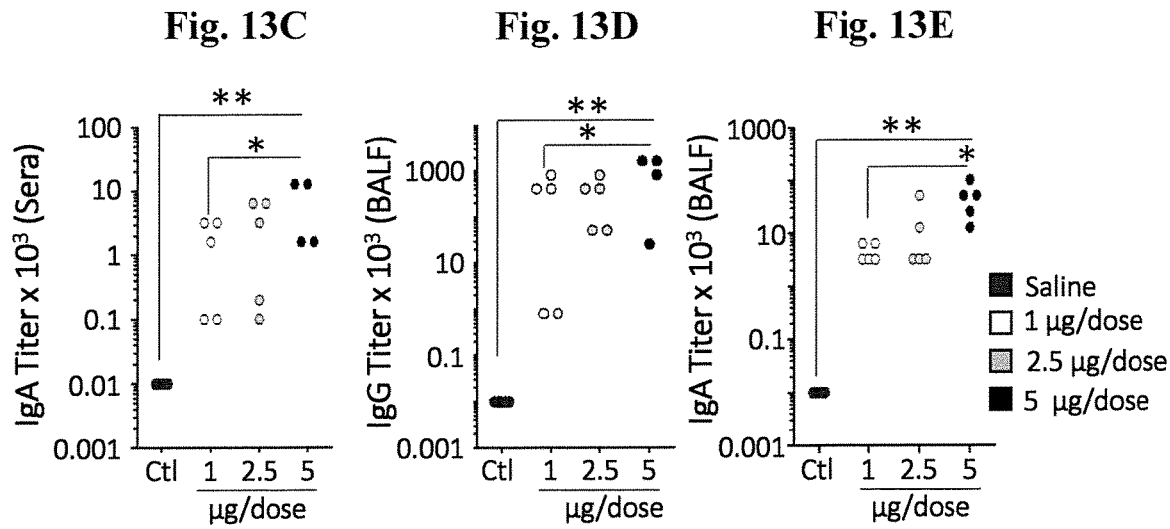

Finally, to evaluate whether vaccination with cSpike-CoV-2 is protective against different SARS-CoV-2 variant infections, sera from vaccinated mice were tested for cross-reactivity against Spike protein from the California, Brazil, South Africa, UK, Indian, and Delta strains, which possess specific mutations in the RBD (FIG. 12A) with respect to the "wild-type" Wuhan strain. As shown in FIGS. 12B and 12C, sera from mice immunized with cSpike-CoV-2 were significantly cross-reactive with the Spike protein from every SARS-CoV-2 variant tested. Furthermore, antibodies from sera of vaccinated mice were protective and had strong neutralization activity against UK, Brazil, South Africa, Delta, and California SARS-CoV-2 strains, as shown by the in vitro neutralization assay (FIG. 12D)

Overall, these findings indicate that the ChAcNLS-CoV-2-Spike protein formulations can be effectively exploited as universal vaccines to trigger potent antiviral responses.

Example 7: In Vivo Therapeutic Vaccination Against Different SARS-CoV-2 Variants To determine whether SARS-CoV-2 vaccines using Spike protein derived from different variants would be effective using the same formulation, cSpike-CoV-2-IN vaccine was produced using the Spike protein from the Indian variant.

Figure 14A:
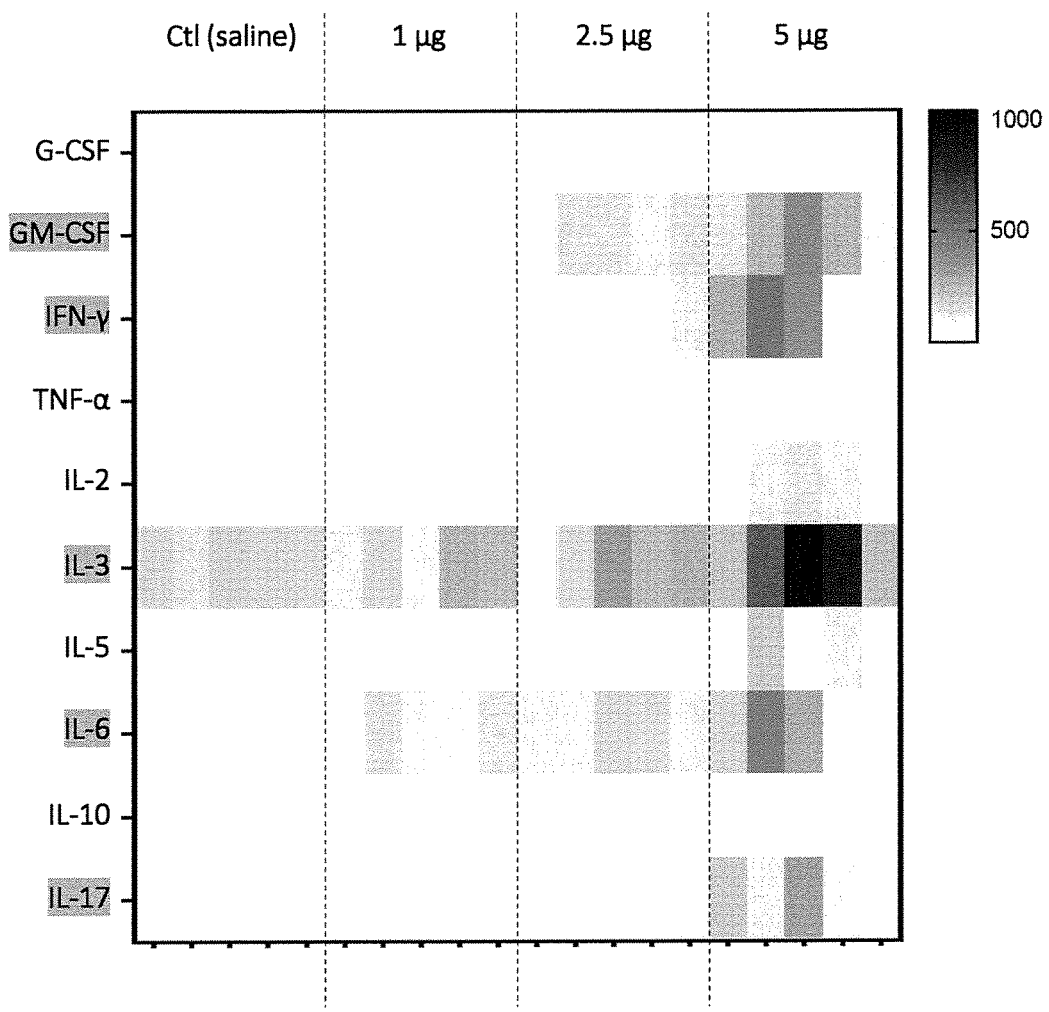
Figure 14B:
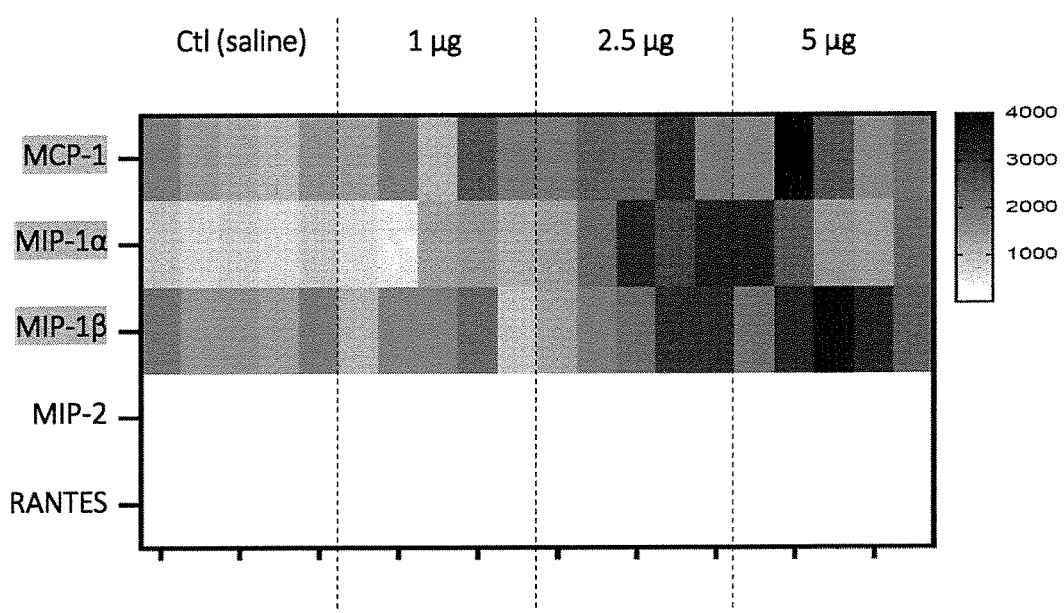

Mice were vaccinated with different doses of the cSpike-CoV-2-IN vaccine or with saline (control), and elevated IgG titers in the sera and BALF were observed at different time points (FIG. 13A-E). Furthermore, a strong cellular response was also observed by the detection of different cytokine and chemokine levels in T cells from mice vaccinated with cSpike-CoV-2-IN (FIG. 14A-B).

Figure 15:
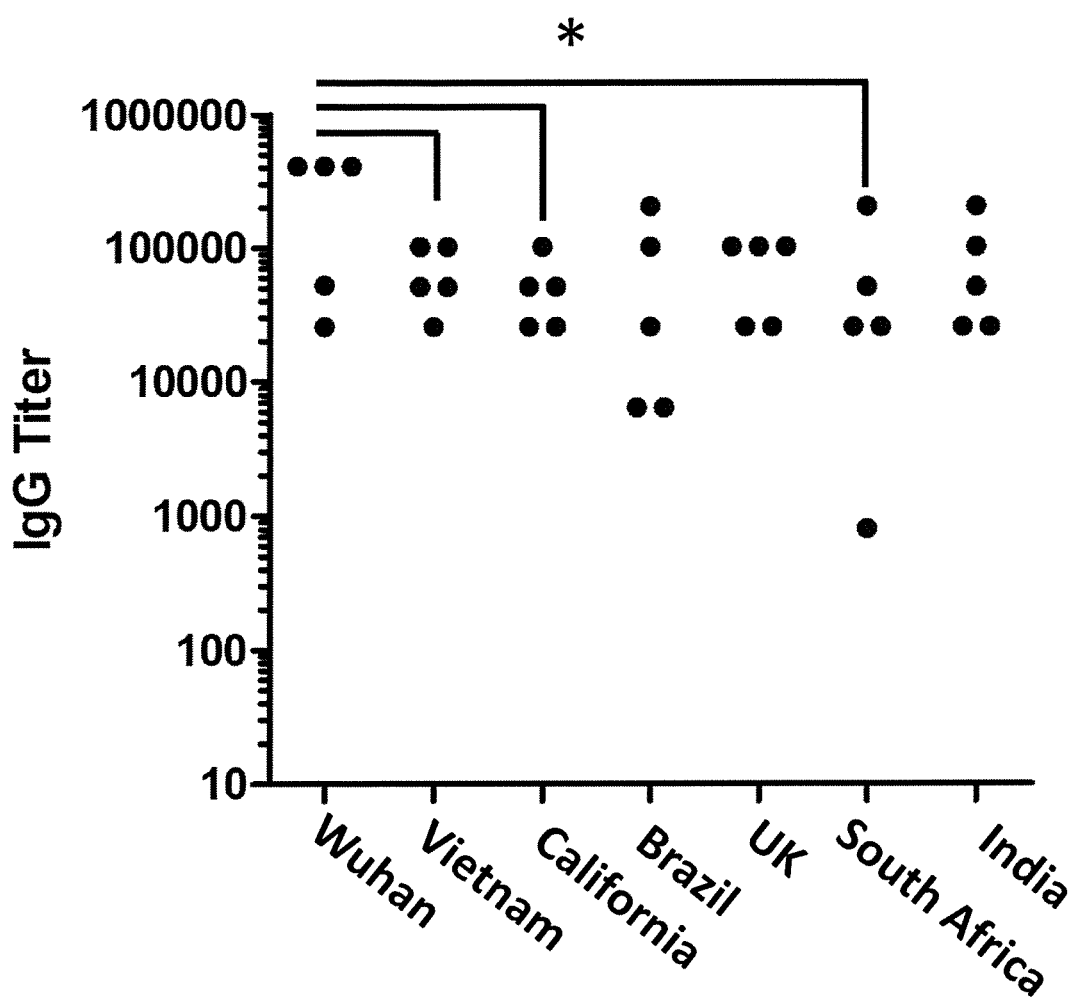
Figure 16A:
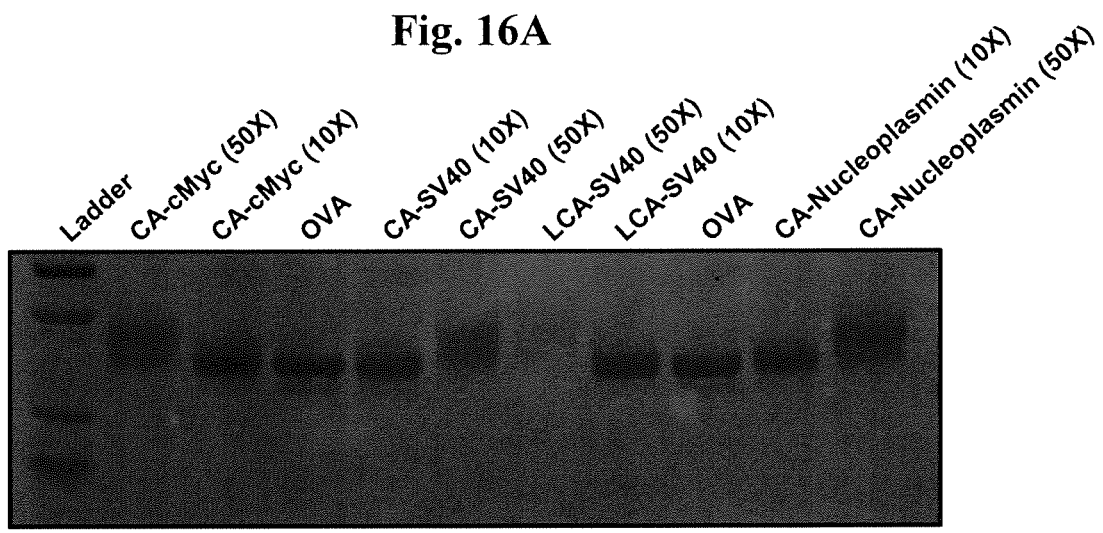
Figure 16B:
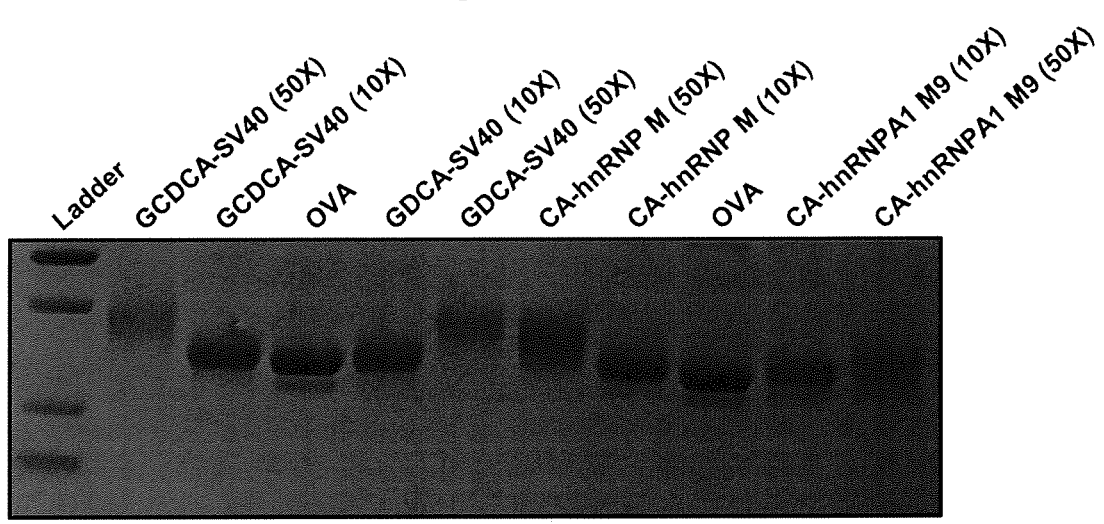
Figure 16C:
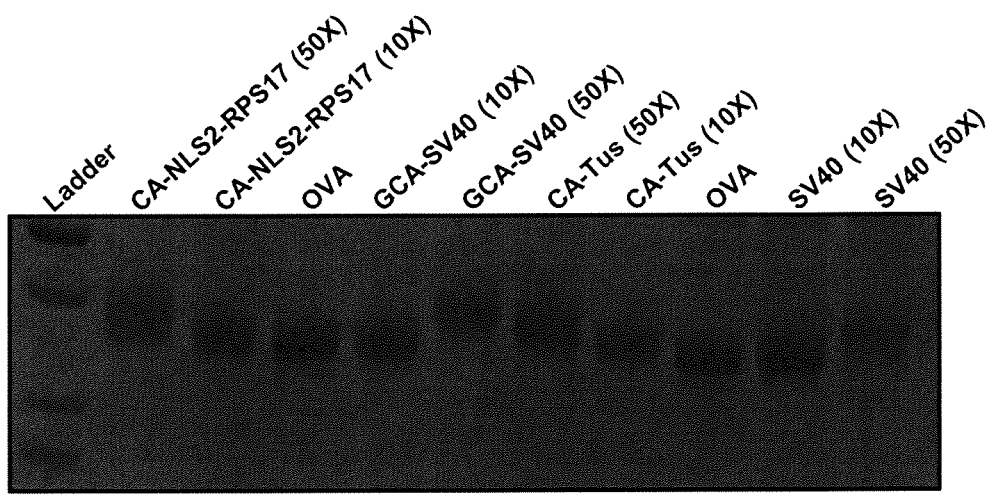
Figure 16D:
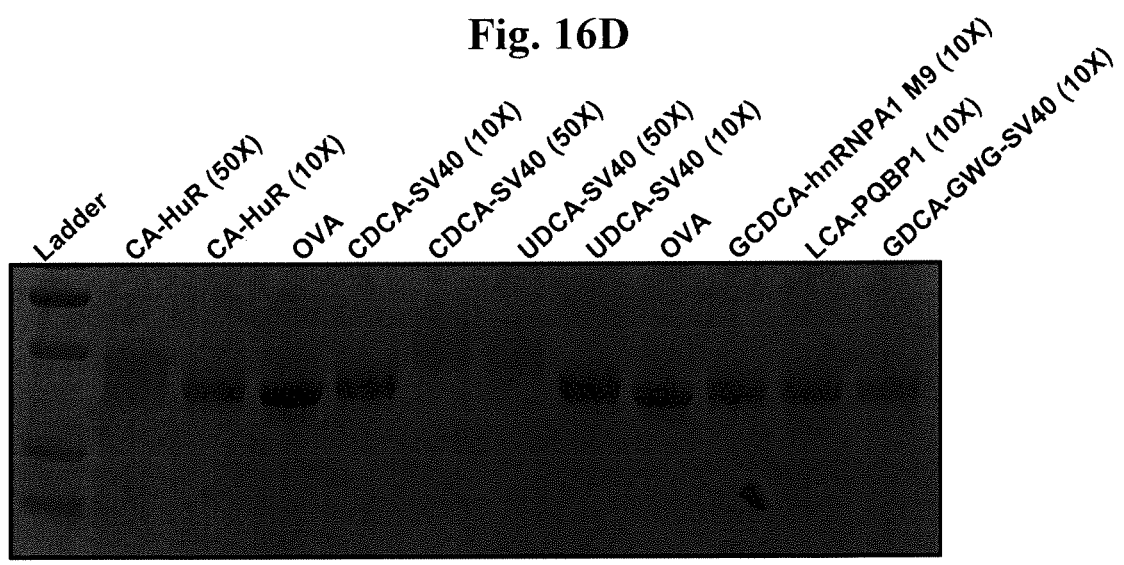
Figure 17:
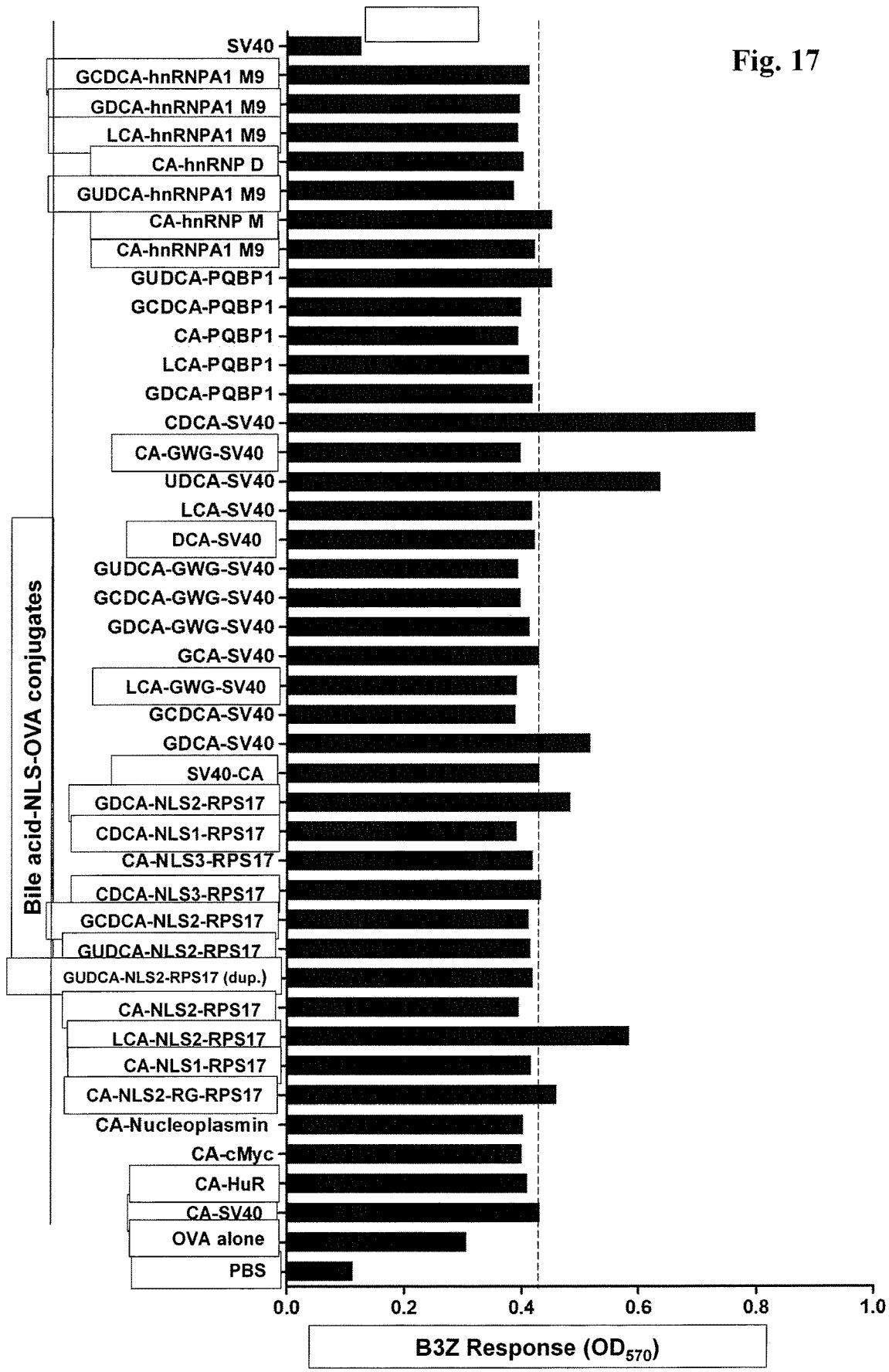
Figure 18:
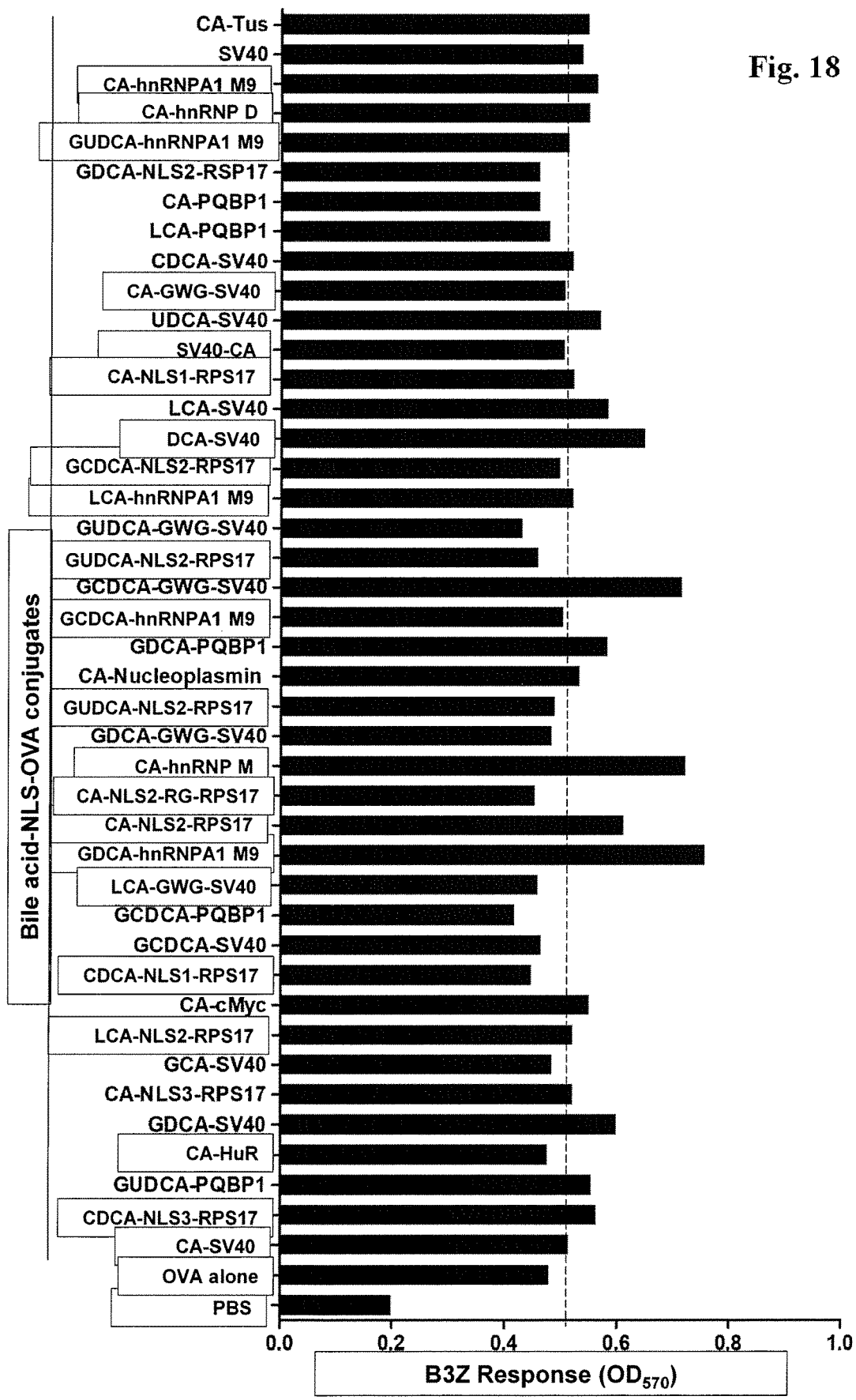

Finally, sera from mice vaccinated with cSpike-CoV-2-IN vaccine were cross-reactive with Spike proteins from all of the different SARS-CoV-2 variants tested (FIG. 15).

Overall, these findings indicate that the ChAcNLS can be adapted to Spike proteins from different SARS-CoV-2 variants to formulate an effective vaccine that triggers a broad, protective, and potent antiviral response.

Example 8: Enhanced Antigen Presentation of Antigen Conjugated to Different Bile Acid-NLS Conjugates Different bile acid-NLS conjugates conjugated to OVA were produced and evaluated for their ability to enhance DC or B cell antigen presentation of OVA in a B3Z reporter assay. Bile acid-NLS-OVA conjugates were produced at 10× or 50× molar excess ratios of bile acid-NLS to OVA, as shown by SDS-PAGE in FIG. 16A-D, but only the results with conjugates produced at a 10× molar excess ratio are shown in the antigen presentation assays of FIG. 17 (dendritic cells) and FIG. 18 (B cells). From the relative migration distances (Rf) calculated from the SDS-PAGE results (e.g., FIG. 16A-D): 10× molar excess of bile acid-NLS reactant resulted in about 1-4 bile acid-NLS moieties conjugated per OVA molecule; 25× molar excess of bile acid-NLS reactant resulted in about 5-9 bile acid-NLS moieties conjugated per OVA molecule; and 50× molar excess of bile acid-NLS reactant resulted in about 12-20 bile acid-NLS moieties conjugated per OVA molecule.

Dendritic Cells as Antigen Presenting Cells

As shown in FIG. 17, all of the different bile acid-NLS conjugates tested enhanced the presentation by BMDCs of OVA at a level similar to or greater than that of CA-SV40 (i.e., ChAcNLS; indicated as a broken line in FIG. 17). Strikingly, the increase in antigen presentation observed for all the bile acid-NLS conjugates tested in FIG. 17 was superior to that of the "OVA alone" control despite the fact that a fifty fold higher concentration of OVA antigen was used (5 mg/mL) as compared to for the OVA conjugates (0.1 mg/mL). Interestingly, several bile-acid-NLS conjugates such as CDCA-SV40, UDCA-SV40, GDCA-SV40, GDCA-NLS2-RPS17, and LCA-NLS2-RPS17 markedly enhanced OVA presentation compared to CA-SV40 (FIG. 17). Furthermore, a negative control in which OVA was conjugated to SV40 peptide alone (without a bile acid) and used at a more comparable concentration of 0.1 mg/mL ("SV40" in FIG. 17) produced a similar result to the "PBS" negative control. The bile acid-NLS conjugate "SV40-CA" differs from the conjugate "CA-SV40" mainly in the placement of the cholic acid group. That is, in the "SV40-CA" conjugate, the cholic acid group is conjugated to the C terminus of the SV40 NLS peptide via a C-terminal lysine residue added to t4he SV40 NLS peptide. As shown in FIG. 17, both the conjugates "SV40-CA" and "CA-SV40" yielded similar B3Z responses, which suggests that the placement of the cholic acid group with respect to the peptide moiety does not affect the immunostimulatory effect of the bile acid-NLS moieties.

B Cells as Antigen Presenting Cells

As shown in FIG. 18, the majority of the different bile acid-NLS conjugates tested yielded comparable or enhanced antigen presentation by B cells as compared to a fifty fold higher dose of the OVA alone (5 mg/mL) control or as compared to CA-SV40 (i.e., ChAcNLS). Interestingly, several bile-acid-NLS conjugates such as DCA-SV40, UDCA-SV40, LCA-SV40, GDCA-GWG-SV40, GDCA-PQBP1, CA-hnRNP M, CA-NLS2-RPS17, GDCA-hnRNPA1 M9, CA-cMyc, GDCA-SV40, GUDCA-PQBP1, and CDCA-NLS3-RPS17 markedly enhanced OVA presentation as compared to CA-SV40.

Overall, these findings support the versatility of a variety of bile acid-NLS conjugates to improve the immunogenicity of a given polypeptide antigen (e.g., resulting from enhanced antigen presentation), potentially enabling the use of lower doses of the polypeptide antigens, which can be the mostly costly ingredient of a subunit vaccine to manufacture.

REFERENCES

Anding A L, Baehrecke E H. Cleaning House: Selective Autophagy of Organelles. *Dev Cell* 2017; 41(1):10-22.

Anguille S, Smits E L, Lion E, et al. Clinical use of dendritic cells for cancer therapy. *Lancet Oncol* 2014; 15(7):e257-67.

Azuar et al., (2019). Cholic Acid-based Delivery System for Vaccine Candidates against Group A *Streptococcus*. *ACS Medicinal Chemistry Letters,* 10: 1253-1529.

Beaudoin et al., (2016). ChAcNLS, a novel modification to antibody-conjugates permitting target cell-specific endosomal escape, localization to the nucleus and enhanced total intracellular accumulation. *Molecular Pharmaceutics,* 13(6): 1915-26.

Hanafi et al., (2018). Overview of Bile Acids Signaling and Perspective on the Signal of Ursodeoxycholic Acid, the Most Hydrophilic Bile Acid, in the Heart. *Biomolecules,* 8(4): 159.

Murakami et al., (2020). Bile acids and ceramide overcome the entry restriction for GII.3 human norovirus replication in human intestinal enteroids. *Proceedings of the National Academy of Sciences USA.* 117(3):1700-1710.

Patel et al., (2017). Next generation approaches for tumor vaccination. *Chinese Clinical Oncology.* 6(2):19.

Shivanna et al., (2014) The crucial role of bile acids in the entry of porcine enteric calicivirus. *Virology* 456-457, 268-278.

Shivanna et al., (2015). Ceramide formation mediated by acid sphingomyelinase facilitates endosomal escape of caliciviruses. *Virology,* 483, 218-228.

Smith et al., (2019). Alternative tumour-specific antigens. *Nature Review Cancer.* 19(8): 465-478.

Sun et al., (2016). Factors influencing the nuclear targeting ability of nuclear localization signals. *Journal of Drug Targeting,* 24(10): 927-933.

Tagliamonte et al., (2014). Antigen-specific vaccines for cancer treatment. *Human Vaccines & Immunotherapeutics,* 10(11): 3332-3346.

The invention claimed is:

1. A method of improving polypeptide antigen immunogenicity, the method comprising providing a polypeptide antigen to be modified, and covalently conjugating the polypeptide antigen to one or more steroid acid-peptide moieties to produce a modified polypeptide antigen, the modified polypeptide antigen being conjugated to a sufficient number of steroid acid-peptide moieties to trigger an improved adaptive immune response to said polypeptide antigen upon administration to a subject as compared to a corresponding unmodified polypeptide antigen, wherein the peptide comprised in the steroid acid-peptide moiety comprises a nuclear localization signal (NLS), and wherein the steroid acid mediates endosomal escape of the modified polypeptide antigen.

2. The method of claim 1, wherein the modified polypeptide antigen is conjugated to a sufficient number of steroid acid-peptide moieties:

to increase antigen presentation of the modified polypeptide antigen upon intracellular delivery relative to a corresponding unmodified polypeptide antigen;

to increase endosomal escape of the modified polypeptide antigen upon intracellular delivery relative to a corresponding unmodified polypeptide antigen; and/or such that the modified polypeptide antigen exhibits greater thermal stability relative to a corresponding unmodified polypeptide antigen.

3. The method of claim 1, wherein covalently conjugating the polypeptide antigen to one or more steroid acid-peptide moieties is performed by reacting the polypeptide antigen with a molar excess of the steroid acid-peptide moiety.

4. The method of claim 3, wherein the polypeptide antigen is reacted with between a 2-fold and 100-fold, a 2-fold and 50-fold, or a 5-fold and 25-fold molar excess of the steroid acid-peptide moiety.

5. The method of claim 1, wherein the mean number of steroid acid-peptide moieties conjugated per modified polypeptide antigen is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50; or is between 1, 2, 3, 4, 5, 6, 7, 8, 9, or 10 and n, wherein n is the total number of accessible sites on the polypeptide antigen available for conjugation.

6. The method of claim 1, wherein the nuclear localization signal is or comprises SV40 NLS (SEQ ID NO: 1 or 7), GWG-SV40NLS (SEQ ID NO: 8), hnRNPA1 M9 NLS (SEQ ID NO: 9), hnRNP D NLS (SEQ ID NO: 10), hnRNP M NLS (SEQ ID NO: 11), PQBP-1 NLS (SEQ ID NO: 12), NLS2-RG Domain RPS17 (SEQ ID NO: 13), NLS1 RPS17 (SEQ ID NO: 14), NLS2 RPS17 (SEQ ID NO: 15), NLS3 RPS17 (SEQ ID NO: 16), cMyc NLS (SEQ ID NO: 17), HuR NLS (SEQ ID NO: 18), Tus NLS (SEQ ID NO: 19), or Nucleoplasmin NLS (SEQ ID NO: 20).

7. The method of claim 1, wherein the polypeptide antigen is conjugated to the steroid acid-peptide moieties via a linker.

8. The method of claim 7, wherein the linker is a bifunctional linker, trifunctional linker, or multi-functional linker.

9. The method of claim 1, wherein the modified polypeptide antigen molecule is conjugated to the one or more steroid acid-peptide moieties via a solvent-accessible amine and/or sulfhydryl group of the polypeptide antigen.

10. The method of claim 1, wherein the polypeptide antigen is or comprises a tumor-associated antigen (TAA), tumor-specific antigen (TSA), a neoantigen, a viral antigen, a bacterial antigen, a fungal antigen, or other antigen associated with a disease or disorder amenable to treatment by vaccination and/or immunotherapy.

11. The method of claim 1, wherein the polypeptide antigen is or comprises a SARS-COV Spike protein or an antigenic fragment thereof.

12. An immunogenic composition comprising: the modified polypeptide antigen produced by the method of claim 1 or a population of cells comprising the modified polypeptide antigen produced by the method of claim 1, and a pharmaceutically acceptable excipient and/or adjuvant.

13. A method for triggering an enhanced adaptive immune response in a subject against an unmodified polypeptide antigen of interest, the method comprising administering the immunogenic composition of claim 12 to the subject.

14. A method for vaccinating a subject against an infectious disease, the method comprising administering the immunogenic composition of claim 12 to the subject, wherein the polypeptide antigen comprises an antigenic fragment of a pathogen causing the infectious disease.

15. A method for treating cancer in a subject, the method comprising administering the immunogenic composition of claim 12 to the subject.

* * * * *

SEQUENCE LISTING

<160> NUMBER OF SEQ ID NOS: 20

<210> SEQ ID NO 1
<211> LENGTH: 13
<212> TYPE: PRT
<213> ORGANISM: Artificial Sequence
<220> FEATURE:
<223> OTHER INFORMATION: ChAcNLS
<220> FEATURE:
<221> NAME/KEY: MOD_RES
<222> LOCATION: (1)..(1)
<223> OTHER INFORMATION: Cholic Acid (ChAc)

<400> SEQUENCE: 1

Cys Gly Tyr Gly Pro Lys Lys Lys Arg Lys Val Gly Gly
1               5                   10

<210> SEQ ID NO 2
<211> LENGTH: 385
<212> TYPE: PRT
<213> ORGANISM: Artificial Sequence
<220> FEATURE:
<223> OTHER INFORMATION: Chicken Ovalbumin (OVA)

<400> SEQUENCE: 2

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
                20                  25                  30

Ala Ile Met Ser Ala Leu Ala Met Val Tyr Leu Gly Ala Lys Asp Ser
            35                  40                  45

Thr Arg Thr Gln Ile Asn Lys Val Val Arg Phe Asp Lys Leu Pro Gly
        50                  55                  60

Phe Gly Asp Ser Ile Glu Ala Gln Cys Gly Thr Ser Val Asn Val His
65                  70                  75                  80

Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
            100                 105                 110

Ile Leu Pro Glu Tyr Leu Gln Cys Val Lys Glu Leu Tyr Arg Gly Gly
        115                 120                 125

Leu Glu Pro Ile Asn Phe Gln Thr Ala Ala Asp Gln Ala Arg Glu Leu
    130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Ala Phe Lys Asp Glu Asp
            180                 185                 190

Thr Gln Ala Met Pro Phe Arg Val Thr Glu Gln Glu Ser Lys Pro Val
        195                 200                 205

Gln Met Met Tyr Gln Ile Gly Leu Phe Arg Val Ala Ser Met Ala Ser
    210                 215                 220

Glu Lys Met Lys Ile Leu Glu Leu Pro Phe Ala Ser Gly Thr Met Ser
225                 230                 235                 240

Met Leu Val Leu Leu Pro Asp Glu Val Ser Gly Leu Glu Gln Leu Glu
                245                 250                 255

Ser Ile Ile Asn Phe Glu Lys Leu Thr Glu Trp Thr Ser Ser Asn Val
            260                 265                 270

```
Met Glu Glu Arg Lys Ile Lys Val Tyr Leu Pro Arg Met Lys Met Glu
            275                 280                 285

Glu Lys Tyr Asn Leu Thr Ser Val Leu Met Ala Met Gly Ile Thr Asp
290                 295                 300

Val Phe Ser Ser Ala Asn Leu Ser Gly Ile Ser Ser Ala Glu Ser
305                 310                 315                 320

Leu Lys Ile Ser Gln Ala Val His Ala Ala His Ala Glu Ile Asn Glu
            325                 330                 335

Ala Gly Arg Glu Val Val Gly Ser Ala Glu Ala Gly Val Asp Ala Ala
            340                 345                 350

Ser Val Ser Glu Glu Phe Arg Ala Asp His Pro Phe Leu Phe Cys Ile
            355                 360                 365

Lys His Ile Ala Thr Asn Ala Val Leu Phe Phe Gly Arg Cys Val Ser
            370                 375                 380

Pro
385

<210> SEQ ID NO 3
<211> LENGTH: 1310
<212> TYPE: PRT
<213> ORGANISM: Artificial Sequence
<220> FEATURE:
<223> OTHER INFORMATION: SARS-CoV-2 Spike protein

<400> SEQUENCE: 3

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240
```

-continued

Leu Leu Ala Leu His Arg Ser Tyr Leu Thr Pro Gly Asp Ser Ser Ser
            245                 250                 255

Gly Trp Thr Ala Gly Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

```
Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
        1010                1015                1020

Leu Ala Ala Thr Lys Met Ser Glu Cys Val Leu Gly Gln Ser Lys
        1025                1030                1035

Arg Val Asp Phe Cys Gly Lys Gly Tyr His Leu Met Ser Phe Pro
        1040                1045                1050

Gln Ser Ala Pro His Gly Val Val Phe Leu His Val Thr Tyr Val
        1055                1060                1065

Pro Ala Gln Glu Lys Asn Phe Thr Thr Ala Pro Ala Ile Cys His
```

```
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr Leu Glu  Ser Gly Gly
    1265                1270                1275

Gly Ser  Ala Trp Ser His Pro  Gln Phe Glu Lys Gly  Gly Gly Ser
    1280                1285                1290

Gly Gly  Gly Ser Gly Gly Ser  Ser Ala Trp Ser His  Pro Gln Phe
    1295                1300                1305

Glu Lys
    1310

<210> SEQ ID NO 4
<211> LENGTH: 1255
<212> TYPE: PRT
<213> ORGANISM: Artificial Sequence
<220> FEATURE:
<223> OTHER INFORMATION: SARS-CoV Spike protein

<400> SEQUENCE: 4

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
```

```
            100                 105                 110
Ser Val Ile Ile Ile Asn Asn Ser Thr Asn Val Ile Arg Ala Cys
            115                 120                 125
Asn Phe Glu Leu Cys Asp Asn Pro Phe Phe Ala Val Ser Lys Pro Met
            130                 135                 140
Gly Thr Gln Thr His Thr Met Ile Phe Asp Asn Ala Phe Asn Cys Thr
145                 150                 155                 160
Phe Glu Tyr Ile Ser Asp Ala Phe Ser Leu Asp Val Ser Glu Lys Ser
                165                 170                 175
Gly Asn Phe Lys His Leu Arg Glu Phe Val Phe Lys Asn Lys Asp Gly
            180                 185                 190
Phe Leu Tyr Val Tyr Lys Gly Tyr Gln Pro Ile Asp Val Val Arg Asp
            195                 200                 205
Leu Pro Ser Gly Phe Asn Thr Leu Lys Pro Ile Phe Lys Leu Pro Leu
210                 215                 220
Gly Ile Asn Ile Thr Asn Phe Arg Ala Ile Leu Thr Ala Phe Ser Pro
225                 230                 235                 240
Ala Gln Asp Ile Trp Gly Thr Ser Ala Ala Tyr Phe Val Gly Tyr
                245                 250                 255
Leu Lys Pro Thr Thr Phe Met Leu Lys Tyr Asp Glu Asn Gly Thr Ile
            260                 265                 270
Thr Asp Ala Val Asp Cys Ser Gln Asn Pro Leu Ala Glu Leu Lys Cys
            275                 280                 285
Ser Val Lys Ser Phe Glu Ile Asp Lys Gly Ile Tyr Gln Thr Ser Asn
            290                 295                 300
Phe Arg Val Val Pro Ser Gly Asp Val Val Arg Phe Pro Asn Ile Thr
305                 310                 315                 320
Asn Leu Cys Pro Phe Gly Glu Val Phe Asn Ala Thr Lys Phe Pro Ser
                325                 330                 335
Val Tyr Ala Trp Glu Arg Lys Lys Ile Ser Asn Cys Val Ala Asp Tyr
            340                 345                 350
Ser Val Leu Tyr Asn Ser Thr Phe Phe Ser Thr Phe Lys Cys Tyr Gly
            355                 360                 365
Val Ser Ala Thr Lys Leu Asn Asp Leu Cys Phe Ser Asn Val Tyr Ala
370                 375                 380
Asp Ser Phe Val Val Lys Gly Asp Asp Val Arg Gln Ile Ala Pro Gly
385                 390                 395                 400
Gln Thr Gly Val Ile Ala Asp Tyr Asn Tyr Lys Leu Pro Asp Asp Phe
                405                 410                 415
Met Gly Cys Val Leu Ala Trp Asn Thr Arg Asn Ile Asp Ala Thr Ser
            420                 425                 430
Thr Gly Asn Tyr Asn Tyr Lys Tyr Arg Tyr Leu Arg His Gly Lys Leu
            435                 440                 445
Arg Pro Phe Glu Arg Asp Ile Ser Asn Val Pro Phe Ser Pro Asp Gly
450                 455                 460
Lys Pro Cys Thr Pro Pro Ala Leu Asn Cys Tyr Trp Pro Leu Asn Asp
465                 470                 475                 480
Tyr Gly Phe Tyr Thr Thr Thr Gly Ile Gly Tyr Gln Pro Tyr Arg Val
                485                 490                 495
Val Val Leu Ser Phe Glu Leu Leu Asn Ala Pro Ala Thr Val Cys Gly
            500                 505                 510
Pro Lys Leu Ser Thr Asp Leu Ile Lys Asn Gln Cys Val Asn Phe Asn
            515                 520                 525
```

```
Phe Asn Gly Leu Thr Gly Thr Gly Val Leu Thr Pro Ser Ser Lys Arg
        530                 535                 540
Phe Gln Pro Phe Gln Gln Phe Gly Arg Asp Val Ser Asp Phe Thr Asp
545                 550                 555                 560
Ser Val Arg Asp Pro Lys Thr Ser Glu Ile Leu Asp Ile Ser Pro Cys
                565                 570                 575
Ser Phe Gly Gly Val Ser Val Ile Thr Pro Gly Thr Asn Ala Ser Ser
                580                 585                 590
Glu Val Ala Val Leu Tyr Gln Asp Val Asn Cys Thr Asp Val Ser Thr
        595                 600                 605
Ala Ile His Ala Asp Gln Leu Thr Pro Ala Trp Arg Ile Tyr Ser Thr
        610                 615                 620
Gly Asn Asn Val Phe Gln Thr Gln Ala Gly Cys Leu Ile Gly Ala Glu
625                 630                 635                 640
His Val Asp Thr Ser Tyr Glu Cys Asp Ile Pro Ile Gly Ala Gly Ile
                645                 650                 655
Cys Ala Ser Tyr His Thr Val Ser Leu Leu Arg Ser Thr Ser Gln Lys
                660                 665                 670
Ser Ile Val Ala Tyr Thr Met Ser Leu Gly Ala Asp Ser Ser Ile Ala
        675                 680                 685
Tyr Ser Asn Asn Thr Ile Ala Ile Pro Thr Asn Phe Ser Ile Ser Ile
        690                 695                 700
Thr Thr Glu Val Met Pro Val Ser Met Ala Lys Thr Ser Val Asp Cys
705                 710                 715                 720
Asn Met Tyr Ile Cys Gly Asp Ser Thr Glu Cys Ala Asn Leu Leu Leu
                725                 730                 735
Gln Tyr Gly Ser Phe Cys Thr Gln Leu Asn Arg Ala Leu Ser Gly Ile
                740                 745                 750
Ala Ala Glu Gln Asp Arg Asn Thr Arg Glu Val Phe Ala Gln Val Lys
        755                 760                 765
Gln Met Tyr Lys Thr Pro Thr Leu Lys Tyr Phe Gly Gly Phe Asn Phe
        770                 775                 780
Ser Gln Ile Leu Pro Asp Pro Leu Lys Pro Thr Lys Arg Ser Phe Ile
785                 790                 795                 800
Glu Asp Leu Leu Phe Asn Lys Val Thr Leu Ala Asp Ala Gly Phe Met
                805                 810                 815
Lys Gln Tyr Gly Glu Cys Leu Gly Asp Ile Asn Ala Arg Asp Leu Ile
                820                 825                 830
Cys Ala Gln Lys Phe Asn Gly Leu Thr Val Leu Pro Pro Leu Leu Thr
        835                 840                 845
Asp Asp Met Ile Ala Ala Tyr Thr Ala Ala Leu Val Ser Gly Thr Ala
850                 855                 860
Thr Ala Gly Trp Thr Phe Gly Ala Gly Ala Ala Leu Gln Ile Pro Phe
865                 870                 875                 880
Ala Met Gln Met Ala Tyr Arg Phe Asn Gly Ile Gly Val Thr Gln Asn
                885                 890                 895
Val Leu Tyr Glu Asn Gln Lys Gln Ile Ala Asn Gln Phe Asn Lys Ala
                900                 905                 910
Ile Ser Gln Ile Gln Glu Ser Leu Thr Thr Thr Ser Thr Ala Leu Gly
        915                 920                 925
Lys Leu Gln Asp Val Val Asn Gln Asn Ala Gln Ala Leu Asn Thr Leu
        930                 935                 940
```

-continued

```
Val Lys Gln Leu Ser Ser Asn Phe Gly Ala Ile Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255
```

<210> SEQ ID NO 5
<211> LENGTH: 8
<212> TYPE: PRT
<213> ORGANISM: Artificial Sequence
<220> FEATURE:
<223> OTHER INFORMATION: OT-I OVA peptide

<400> SEQUENCE: 5

```
Ser Ile Ile Asn Phe Glu Lys Leu
1               5
```

<210> SEQ ID NO 6
<211> LENGTH: 17

-continued

```
<212> TYPE: PRT
<213> ORGANISM: Artificial Sequence
<220> FEATURE:
<223> OTHER INFORMATION: OT-II OVA peptide

<400> SEQUENCE: 6

Ile Ser Gln Ala Val His Ala Ala His Ala Glu Ile Asn Glu Ala Gly
1               5                   10                  15

Arg

<210> SEQ ID NO 7
<211> LENGTH: 7
<212> TYPE: PRT
<213> ORGANISM: Artificial Sequence
<220> FEATURE:
<223> OTHER INFORMATION: NLS from SV-40 large T-antigen

<400> SEQUENCE: 7

Pro Lys Lys Lys Arg Lys Val
1               5

<210> SEQ ID NO 8
<211> LENGTH: 19
<212> TYPE: PRT
<213> ORGANISM: Artificial Sequence
<220> FEATURE:
<223> OTHER INFORMATION: GWG-SV40NLS

<400> SEQUENCE: 8

Cys Gly Trp Trp Gly Tyr Gly Pro Lys Lys Lys Arg Lys Val Gly Gly
1               5                   10                  15

Trp Trp Gly

<210> SEQ ID NO 9
<211> LENGTH: 20
<212> TYPE: PRT
<213> ORGANISM: Artificial Sequence
<220> FEATURE:
<223> OTHER INFORMATION: hnRNPA1 M9 NLS

<400> SEQUENCE: 9

Cys Ser Asn Phe Gly Pro Met Lys Gly Gly Asn Phe Gly Gly Arg Ser
1               5                   10                  15

Ser Gly Pro Tyr
            20

<210> SEQ ID NO 10
<211> LENGTH: 20
<212> TYPE: PRT
<213> ORGANISM: Artificial Sequence
<220> FEATURE:
<223> OTHER INFORMATION: hnRNP D NLS

<400> SEQUENCE: 10

Cys Ser Gly Tyr Gly Lys Val Ser Arg Arg Gly Gly His Gln Asn Ser
1               5                   10                  15

Tyr Lys Pro Tyr
            20

<210> SEQ ID NO 11
<211> LENGTH: 20
<212> TYPE: PRT
<213> ORGANISM: Artificial Sequence
<220> FEATURE:
<223> OTHER INFORMATION: hnRNP M NLS
```

```
<400> SEQUENCE: 11

Cys Asn Glu Lys Arg Lys Glu Lys Asn Ile Lys Arg Gly Gly Asn Arg
1               5                   10                  15

Phe Glu Pro Tyr
            20

<210> SEQ ID NO 12
<211> LENGTH: 21
<212> TYPE: PRT
<213> ORGANISM: Artificial Sequence
<220> FEATURE:
<223> OTHER INFORMATION: PQBP-1 NLS

<400> SEQUENCE: 12

Cys Ala Asp Arg Glu Glu Gly Lys Glu Arg Arg His His Arg Arg Glu
1               5                   10                  15

Glu Leu Ala Pro Tyr
            20

<210> SEQ ID NO 13
<211> LENGTH: 34
<212> TYPE: PRT
<213> ORGANISM: Artificial Sequence
<220> FEATURE:
<223> OTHER INFORMATION: NLS2-RG Domain RPS17

<400> SEQUENCE: 13

Cys Asn Lys Arg Val Cys Glu Glu Ile Ala Ile Ile Pro Ser Lys Lys
1               5                   10                  15

Leu Arg Asn Lys Gly Ser Gly Arg Ile Gln Arg Gly Pro Val Arg Gly
            20                  25                  30

Ile Ser

<210> SEQ ID NO 14
<211> LENGTH: 16
<212> TYPE: PRT
<213> ORGANISM: Artificial Sequence
<220> FEATURE:
<223> OTHER INFORMATION: NLS1 RPS17

<400> SEQUENCE: 14

Cys Met Gly Arg Val Arg Thr Lys Thr Val Lys Lys Ala Ala Gly Gly
1               5                   10                  15

<210> SEQ ID NO 15
<211> LENGTH: 20
<212> TYPE: PRT
<213> ORGANISM: Artificial Sequence
<220> FEATURE:
<223> OTHER INFORMATION: NLS2 RPS17

<400> SEQUENCE: 15

Cys Asn Lys Arg Val Cys Glu Glu Ile Ala Ile Ile Pro Ser Lys Lys
1               5                   10                  15

Leu Arg Asn Lys
            20

<210> SEQ ID NO 16
<211> LENGTH: 20
<212> TYPE: PRT
<213> ORGANISM: Artificial Sequence
<220> FEATURE:
<223> OTHER INFORMATION: NLS3 RPS17
```

```
<400> SEQUENCE: 16

Cys Ser Lys Lys Leu Arg Asn Lys Ile Ala Gly Tyr Val Thr His Leu
1               5                   10                  15

Met Lys Arg Ile
            20

<210> SEQ ID NO 17
<211> LENGTH: 15
<212> TYPE: PRT
<213> ORGANISM: Artificial Sequence
<220> FEATURE:
<223> OTHER INFORMATION: cMyc NLS

<400> SEQUENCE: 17

Cys Gly Tyr Gly Pro Ala Ala Lys Arg Val Lys Leu Asp Gly Gly
1               5                   10                  15

<210> SEQ ID NO 18
<211> LENGTH: 22
<212> TYPE: PRT
<213> ORGANISM: Artificial Sequence
<220> FEATURE:
<223> OTHER INFORMATION: HuR NLS

<400> SEQUENCE: 18

Cys Gly Arg Phe Ser Pro Met Gly Val Asp His Met Ser Gly Leu Ser
1               5                   10                  15

Gly Val Asn Val Pro Gly
            20

<210> SEQ ID NO 19
<211> LENGTH: 15
<212> TYPE: PRT
<213> ORGANISM: Artificial Sequence
<220> FEATURE:
<223> OTHER INFORMATION: Tus NLS

<400> SEQUENCE: 19

Cys Gly Tyr Gly Lys Leu Lys Ile Lys Arg Pro Val Lys Gly Gly
1               5                   10                  15

<210> SEQ ID NO 20
<211> LENGTH: 21
<212> TYPE: PRT
<213> ORGANISM: Artificial Sequence
<220> FEATURE:
<223> OTHER INFORMATION: Nucleoplasmin NLS

<400> SEQUENCE: 20

Cys Ala Val Lys Arg Pro Ala Ala Thr Lys Lys Ala Gly Gln Ala Lys
1               5                   10                  15

Lys Lys Lys Leu Asp
            20
```